US008524234B2

(12) United States Patent
Getts et al.

(10) Patent No.: US 8,524,234 B2
(45) Date of Patent: Sep. 3, 2013

(54) ANTIBODY FOR SELECTIVE INHIBITION OF T-CELL RESPONSES

(71) Applicant: Tolera Therapeutics, Inc., Kalamazoo, MI (US)

(72) Inventors: Daniel R. Getts, Alexandria, VA (US); James J. Herrmann, Elmhurst, IL (US); John J. Puisis, Glenview, IL (US); Frank J. Fokta, West Chicago, IL (US)

(73) Assignee: Tolera Therapeutics, Inc, Kalamazoo, MI (US)

( * ) Notice: Subject to any disclaimer, the term of this patent is extended or adjusted under 35 U.S.C. 154(b) by 0 days.

(21) Appl. No.: 13/669,221

(22) Filed: Nov. 5, 2012

(65) Prior Publication Data
US 2013/0122015 A1 May 16, 2013

Related U.S. Application Data

(60) Provisional application No. 61/555,344, filed on Nov. 3, 2011, provisional application No. 61/555,335, filed on Nov. 3, 2011, provisional application No. 61/589,715, filed on Jan. 23, 2012, provisional application No. 61/610,348, filed on Mar. 13, 2012, provisional application No. 61/654,631, filed on Jun. 1, 2012.

(51) Int. Cl.
C07K 16/28 (2006.01)

(52) U.S. Cl.
USPC ................ 424/144.1; 530/388.75; 530/391.3; 435/188

(58) Field of Classification Search
None
See application file for complete search history.

(56) References Cited

U.S. PATENT DOCUMENTS

| 7,560,425 | B2 | 7/2009 | Brand et al. |
| 8,138,314 | B2 | 3/2012 | Exley et al. |
| 8,178,098 | B2 | 5/2012 | Lahn et al. |
| 2007/0160600 | A1 | 7/2007 | Exley et al. |
| 2009/0035359 | A1 | 2/2009 | Cohen et al. |
| 2009/0269337 | A1 | 10/2009 | Brand et al. |
| 2010/0068193 | A1 | 3/2010 | Brunsvig et al. |
| 2010/0129340 | A1 | 5/2010 | Rasmussen et al. |
| 2010/0150947 | A1 | 6/2010 | Siemionow |
| 2010/0310588 | A1 | 12/2010 | Bluestone et al. |
| 2011/0123590 | A1 | 5/2011 | Iwashima et al. |
| 2011/0124017 | A1 | 5/2011 | Baniyash et al. |
| 2011/0217302 | A1 | 9/2011 | Odegard et al. |
| 2011/0287533 | A1 | 11/2011 | Chang |
| 2011/0293607 | A1 | 12/2011 | Labrijn et al. |
| 2012/0034249 | A1 | 2/2012 | June et al. |
| 2012/0148605 | A1 | 6/2012 | Hansson |
| 2012/0190828 | A1 | 7/2012 | Jakobsen et al. |

FOREIGN PATENT DOCUMENTS

| EP | 0 403 156 B1 | 9/1997 |
| EP | 2336187 | 6/2011 |
| WO | WO2007107764 | 9/2007 |
| WO | WO2008039818 | 4/2008 |
| WO | WO2008087219 | 4/2008 |
| WO | WO2008089053 | 4/2008 |
| WO | WO2010022198 | 2/2010 |
| WO | WO2010042904 | 4/2010 |
| WO | WO2010063785 | 6/2010 |
| WO | WO2010075417 | 7/2010 |
| WO | WO2010088522 | 8/2010 |
| WO | WO2010099205 | 9/2010 |
| WO | WO2010107380 | 9/2010 |
| WO | WO2010141658 | 12/2010 |
| WO | WO2011090754 | 7/2011 |
| WO | WO2011090762 | 7/2011 |
| WO | WO2012012737 | 1/2012 |
| WO | WO2012018687 | 2/2012 |
| WO | WO2012038922 | 3/2012 |
| WO | WO2012040012 | 3/2012 |
| WO | WO2012054825 | 4/2012 |

OTHER PUBLICATIONS

Roederer et al., "Heterogenous calcium flux in peripheral T cell subsets revealed by five-color flow cytometry using log-ratio circuitry." Cytometry 21: pp. 187-196, Apr. 1995.
International Search Report and Written Opinion, PCT US2012/063583, mailed Feb. 8, 2013. 14 pages.
Brown, S. A., B. A. Lucas, T. H. Waid, J. W. McKeown, S. Barve, L. R. Jackson & J. S. Thompson (1996) T10B9 (MEDI-500) mediated immunosuppression: studies on the mechanism of action. Clin Transplant, 10, 607-13.
Kawaguchi, M. & D. D. Eckels (1995) Differential activation through the TCR-CD3 complex affects the requirement for costimulation of human T cells. Hum Immunol, 43, 136-48.
Keever-Taylor, C. A., A. Craig, M. Molter, P. Fu, A. Loebel, J. Skonecki, H. Zeng & B. Giesen (2001) Complement-mediated T-cell depletion of bone marrow: comparison of T10B9.1A-31 and Muromonab-Orthoclone OKT3. Cytotherapy, 3, 467-81.
Lamb, L. S., Jr., P. J. Henslee-Downey, R. S. Parrish, K. Godder, J. Thompson, C. Lee & A. P. Gee (1996) Increased frequency of TCR gamma delta + T cells in disease-free survivors following T cell-depleted, partially mismatched, related donor bone marrow transplantation for leukemia. J Hematother, 5, 503-9.
Lucas, B. A., T. H. Waid, J. S. Thompson, S. A. Brown, L. C. Munch, J. W. McKeown, R. J. Kryscio & R. J. Prebeck (1993) Comparison of T10Bg.1A-31 and OKT3 in treating acute renal allograft rejection. Transplant Proc, 25, 543-5.

(Continued)

Primary Examiner — Robert A Zeman
(74) Attorney, Agent, or Firm — Cooley LLP

(57) ABSTRACT

The present invention provides compositions, methods, and assays for treating an inflammatory and/or autoimmune disease, and/or transplanted tissue rejection using anti-αβ TCR antibodies and antibody fragments. Anti-αβ TCR antibodies are antibodies which bind to a αβ TCR. Anti-αβ TCR antibodies produced by the hybridoma TOL101 MCB are also provided. Methods for treatment of an inflammatory disease, an autoimmune disease and for tissue transplant rejection using therapeutic dosing regimen of anti-αβ TCR antibodies and antibody fragments and for upregulating the numbers of Treg T-cells are also provided.

2 Claims, 36 Drawing Sheets

(56) References Cited

OTHER PUBLICATIONS

Waid, T. H., B. A. Lucas, J. S. Thompson, J. W. McKeown, S. Brown, R. Kryscio & L. J. Skeeters (1997) Treatment of renal allograft rejection with T10B9.1A31 or OKT3: final analysis of a phase II clinical trial. Transplantation, 64, 274-81.

Waid, T. H., B. A. Lucas, J. S. Thompson, L. C. Munch, S. Brown, R. Kryscio, R. Prebeck, M. A. VanHoy & D. Jezek (1991) Treatment of acute rejection with anti-T-cell antigen receptor complex alpha beta (T10B9.1A-31) or anti-CD3 (OKT3) monoclonal antibody: results of a prospective randomized double-blind trial. Transplant Proc, 23, 1062-5.

Waid, T. H., B. A. Lucas, J. S. Thompson, S. A. Brown, L. Munch, R. J. Prebeck & D. Jezek (1992) Treatment of acute cellular rejection with T10B9.1A-31 or OKT3 in renal allograft recipients. Transplantation, 53, 80-6.

Waid, T. H., B. A. Lucas, J. S. Thompson, S. Brown, D. Moore, P. Amlot & G. Janossy (1989) Treatment of acute cellular kidney allograft rejection with T10B9.1A-31A anti T-cell monoclonal antibody. Transplant Proc, 21, 1778-84.

Waid, T. H., B. A. Lucas, P. Amlot, G. Janossy, M. Yacoub, S. Cammisuli, D. Jezek, J. Rhoades, S. Brown & J. S. Thompson (1989) T10B9.1A-31 anti-T-cell monoclonal antibody: preclinical studies and clinical treatment of solid organ allograft rejection. Am J Kidney Dis, 14, 61-70.

Lavasani, S., Dzhambazov, B. & Andersson, M. 2007. Monoclonal antibody against T-cell receptor alphabeta induces self-tolerance in chronic experimental autoimmune encephalomyelitis. Scand J Immunol, 65, 39-47.

Matsumoto,Y., Tsuchida, M., Hanawa, H. & Abo,T. 1994. Successful prevention and treatment of autoimmune encephalomyelitis by short-term administration of anti-T-cell receptor alpha beta antibody. Immunology, 81, 1-7.

Conrad, M.L., Davis, W.C. & Koop, B.F. TCR and CD3 antibody cross-reactivity in 44 species. Cytometry A 71, 925-33 (2007).

Sempé P, Bédossa P, Richard MF, Villà MC, Bach JF, Boitard C. Anti-alpha/beta T cell receptor monoclonal antibody provides an efficient therapy for autoimmune diabetes in nonobese diabetic (NOD) mice. Eur J Immunol. May 1991;21(5):1163-9.

Knight RJ, Kurrle R, McClain J, Racenberg J, Baghdahsarian V, Kerman R, Lewis R, van Buren CT, Kahan BD. Clinical evaluation of induction immunosuppression with a murine IgG2b monoclonal antibody (BMA 031) directed toward the human alpha/beta-T cell receptor. Transplantation Jun. 1994 57(11): 1581-1588.

Pfeffer PF, Ohlman S, Jakobsen A, Fauchald P, Leivestad T, Tydén G, Flatmark A. A Scandinavian two-center study of BMA 031 in steroid-resistant rejection of renal grafts. Transplantation. Aug. 1993;56(2):304-7.

Zlabinger GJ, Stuhlmeier KM, Eher R, Schmaldienst S, Klauser R, Vychytil A, Watschinger B, Traindl O, Kovarik J, Pohanka E. Cytokine release and dynamics of leukocyte populations after CD3/TCR monoclonal antibody treatment 1992. Journal of Clinical Immunology 12(3) 170-177.

Schwinzer R, Schlitt HJ, Wonigeit K. Monoclonal antibodies to common epitopes of the human alpha/beta T-cell receptor preferentially activate CD45RA+ T-cells J Immunol. Mar. 1, 1992;148(5):1322-8.

Schwinzer R, Franklin RA, Domenico J, Renz H, Gelfand EW Monoclonal antibodies directed to different epitopes in the CD3-TCR complex induce different states of competence in resting human T cells.. Cell Immunol. Mar. 1992;140(1):31-41.

Shearman CW, Kanzy EJ, Lawrie DK, Li YW, Thammana P, Moore GP, Kurrle R. Construction, expression, and biologic activity of murine/human chimeric antibodies with specificity for the human alpha/beta T cell receptor. J Immunol. Feb. 1, 1991;146(3):928-35.

Szamel M, Kracht M, Krebs B, Hübner U, Resch K. Activation signals in human lymphocytes: interleukin 2 synthesis and expression of high affinity interleukin 2 receptors require differential signaling for the activation of protein kinase C. Cell Immunol. Mar. 1990;126(1):117-28.

Miyahara Y, Khattar M, Schroder PM, Mierzejewska B, Deng R, Han R, Hancock WW, Chen W, Stepkowski SM. Anti-TCRβ mAb induces long-term allograft survival by reducing antigen-reactive T cells and sparing regulatory T cells. Am J Transplant. Jun. 2012;12(6):1409-18. doi: 10.1111/j.1600-6143.2012.04006.x. Epub Mar. 15, 2012.

Getts DR, Shankar S, Chastain EM, Martin A, Getts MT, Wood K, Miller SD. Current landscape for T-cell targeting in autoimmunity and transplantation. Immunotherapy. Jul. 2011;3(7):853-70. doi: 10.2217/imt.11.61. Review.

Getts DR, Getts MT, McCarthy DP, Chastain EM, Miller SD. Have we overestimated the benefit of human(ized) antibodies? MAbs. Nov.-Dec. 2010;2(6):682-94. Epub Nov. 1, 2010. Review.

Getts DR, Brown S, Siemionow M, Miller SD. Abstract. TOL101; a New Aid to Prevent Allograft Rejection vol. 9, Issue s2, May 2009, pp. 728-729, Article first published online : Apr. 10, 2009, DOI: 10.1111/j.1600 6143.2009.02659.x.

Siemenow M, Brown SA, Thompson JS, Miller SD, Getts DR.. Abstract. TOL101; a Novel αβ TCR Targeting Monoclonal Antibody vol. 10, Issue s2, Jan. 2010, pp. 36., Article first published online : Jan. 14, 2010, DOI: 10.1111/j.1600-6143.2010.03024.x.

Getts DR, Martin A, Siemionow M, Miller SD. Abstract. Operational Tolerance vs Immune Suppression, Targeting the αβ TCR with TOL101. vol. 10, Issue s4, Apr. 2010, p. 210, Article first published online : Mar. 23, 2010, DOI: 10.1111/j.1600-6143.2010.03107.x.

Fung JJ, Bollinger JE, Miller M and Eghtesad B., Future prospects in immunosuppression for liver transplantation. 2011 Liver Transplantation 17 S54-S59.

Flechner, SM, S. Mulgaonkar, L. Melton, A. Wiseman, R. Sung, T. Waid, . Shihab, M. T. Getts, D. R. Getts. First in Man Evaluation of the Safety and Potential Efficacy of TOL101 Induction to Prevent Kidney Transplant Rejection. vol. 12, Issue s3, May 2012, Abstract 99, Article first published online : Apr. 26, 2012, DOI: 10.1111/j.1600-6143.2012.04112.

Flechner, SM, S. Mulgaonkar, L. Melton, T. Waid, JS Thompson, SA Brown, MT Getts, TJ Frederick, RS Sung, AC Wiseman, F Shihab, DR Getts. First in Man Evaluation of the Safety and Potential Efficacy of TOL101 Induction to Prevent Kidney Transplant Rejection. American Transplant Congress Jun. 2-6, 2012; Boston, MA.

Flechner, SM, S. Mulgaonkar, L. Melton, T. Waid, JS Thompson, SA Brown, MT Getts, TJ Frederick, RS Sung, AC Wiseman, F Shihab, DR Getts. Protocol TTI-121 A Two Part, Phase II Safety, PK and PD Study of TOL101, an Anti-TCR Monoclonal Antibody for Prophylaxis of Acute Organ Rejection in Patients Receiving Renal Transplantation. American Transplant Congress Jun. 2-6, 2012; Boston, MA.

Wiseman AC, Mulgaonkar S, Sung RS, Melton LB, Waid TH, Thompson JS, Brown SA, Getts MT, Frederick TJ, Getts DR and Flechner SM. Immune Monitoring during TOL101 anti-ab TCR monoclonal Phase 2 renal transplant clinical trials. Poster Presentation. ESOT Glasgow Conference Sep. 4-7, 2011.

Getts DR, Wiseman AC, Mulgaonkar S, Sung RS, Melton LB, Waid TH, Thompson JS, Brown SA, Getts MT, Frederick TJ. Evaluating the Safety and Efficacy of TOL101 Induction to Prevent Kidney Transplant Rejection, Part A Interim Analysis. Oral Presentation. ESOT Glasgow Conference Sep. 4-7, 2011.

FIGURE 16

| Phase 2a | Open label ascending dose trial in renal transplant recipients to identify two potentially therapeutic doses (PTD-A and PTD-B) of TOL101 for Part B |
|---|---|
| TOL101 Phase 2a escalating dose strategy | 0.28mg (1/10$^{th}$ MABEL) (N=2)<br>1.4mg (n=2)<br>7mg (n=2)<br>14mg (n=2)<br>28mg (n=3)<br>42mg (Currently enrolling)<br>56mg (TBD) |
| TOL101 clinical endpoints | *Primary- Safety& tolerability* including infusion reactions, adverse events, cytokine release, infections, malignancies & standard biochemistry and hematology.<br>*Secondary- Efficacy* including BPAR, graft survival, subject survival, renal function, DGF, DSA<br>*Secondary- Immune monitoring* including CD3 counts, leukocyte subsets, antibodies to TOL101 (neutralizing or non-neutralizing). |
|  |  |
| Phase 2b | Randomized parallel arm active control trial to compare safety, PD, and clinical efficacy of two PTDs of TOL101 vs Thymoglobulin (TMG) |

FIGURE 32

| Study Day | Statistic | All patients (N=28) | 0.28mg (N=2) | 1.4mg (N=2) | 7mg (N=2) | 14mg (N=2) | 28mg (N=6) | 32 mg (N=4) | 42mg (N=4) | Dose Escalation (N=6) |
|---|---|---|---|---|---|---|---|---|---|---|
| Baseline | Mean | 329 | 481 | 237 | 281 | 288 | 291 | 338 | 262 | 386 |
| | SD | 173 | 66 | 111 | N/A | 55 | 291 | 168 | 149 | 139 |
| 1 | Mean | 24 | 125 | 112 | 18 | 7 | 5 | 5 | 2 | 10 |
| | SD | 44 | 5 | 91 | 17 | 3 | 8 | 3 | 1 | 4 |
| 102 | Mean | 22 | 181 | 255 | 32 | 13 | 2 | 7 | 4 | 7 |
| | SD | 37 | 78 | N/A | 42 | 10 | 1 | 3 | N/A | 5 |
| 3 | Mean | 22 | 213 | 438 | 26 | 16 | 17 | 7 | 5 | 6 |
| | SD | 49 | 87 | N/A | N/A | 15 | 27 | 6 | N/A | 5 |
| 4 | Mean | 88 | 74 | 144 | N/A | N/A | N/A | 3 | N/A | 8 |
| | SD | 37 | N/A | N/A | N/A | N/A | N/A | N/A | N/A | N/A |
| 5 | Mean | 82 | 13 | 91 | 72 | 78 | 8 | 5 | 1 | 2 |
| | SD | 106 | N/A | N/A | 48 | 25 | 9 | 5 | 2 | 1 |
| Last Dose Follow Up | Mean | 309 | 88 | 531 | N/A | N/A | 34 | 13 | 10 | 25 |
| | SD | 313 | N/A | N/A | N/A | N/A | 57 | 4 | 16 | 15 |
| 14 | Mean | 462 | 483 | 230 | 214 | 507 | 740 | 341 | 237 | 500 |
| | SD | 425 | 101 | 174 | 7 | 507 | 711 | 80 | 160 | 290 |

ND = not detected

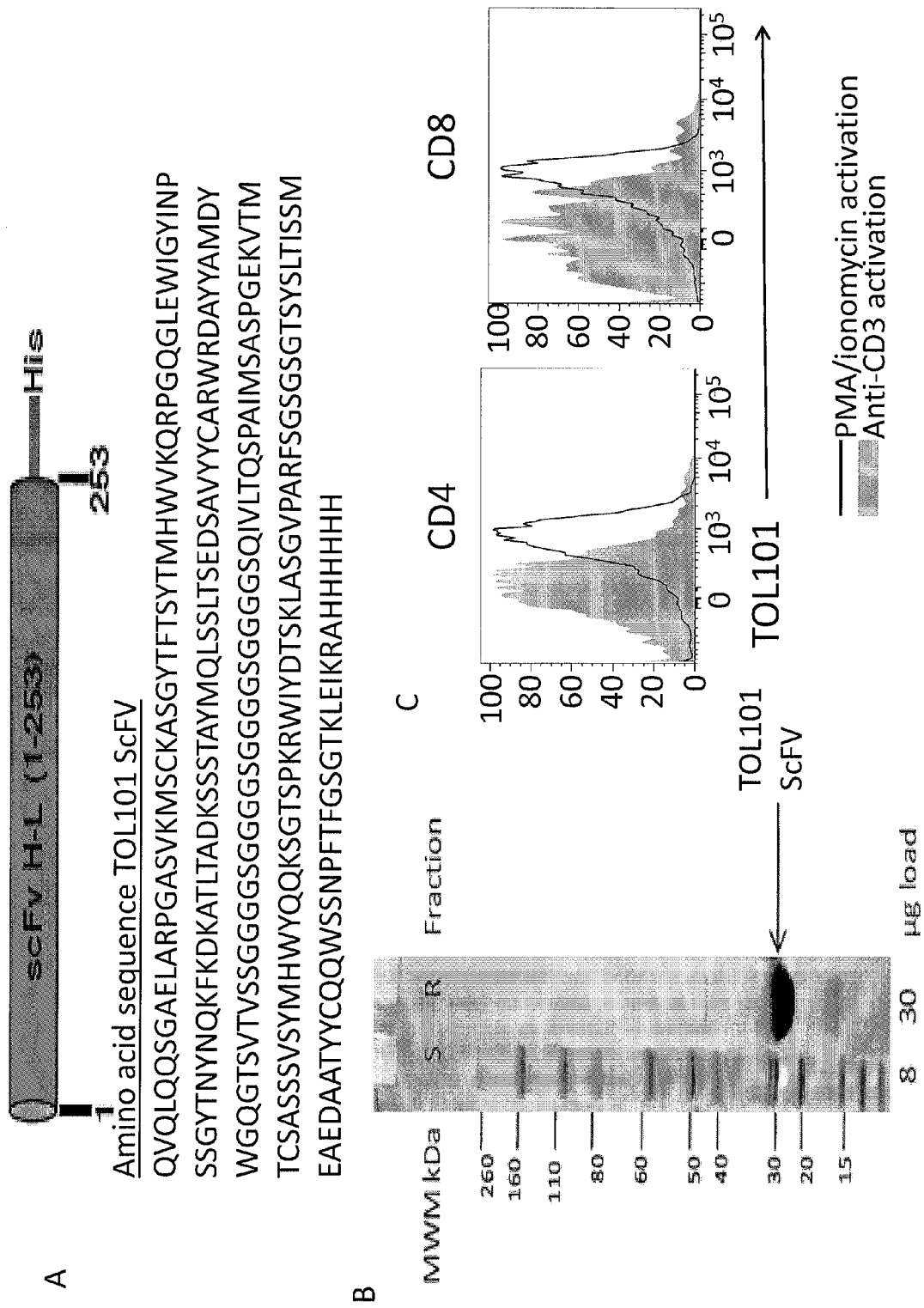

SEQUENCE LISTING

```
<160> NUMBER OF SEQ ID NOS: 9

<210> SEQ ID NO 1
<211> LENGTH: 207
<212> TYPE: PRT
<213> ORGANISM: Homo sapiens

<400> SEQUENCE: 1

Met Ala Lys Thr Thr Gln Pro Asn Ser Met Glu Ser Asn Glu Glu Glu
1               5                   10                  15

Pro Val His Leu Pro Cys Asn His Ser Thr Ile Ser Gly Thr Asp Tyr
                20                  25                  30

Ile His Trp Tyr Arg Gln Leu Pro Ser Gln Gly Pro Glu Tyr Val Ile
            35                  40                  45

His Gly Leu Thr Ser Asn Val Asn Asn Arg Met Ala Ser Leu Ala Ile
```

```
                50             55              60
Ala Glu Asp Arg Lys Ser Ser Thr Leu Ile Leu His Arg Ala Thr Leu
65                  70                  75                  80

Arg Asp Ala Ala Val Tyr Tyr Cys Ile Leu Pro Leu Ala Gly Gly Thr
                85                  90                  95

Ser Tyr Gly Lys Leu Thr Phe Gly Gln Gly Thr Ile Leu Thr Val His
            100                 105                 110

Pro Asn Ile Gln Asn Pro Asp Pro Ala Val Tyr Gln Leu Arg Asp Ser
            115                 120                 125

Lys Ser Ser Asp Lys Ser Val Cys Leu Phe Thr Asp Phe Asp Ser Gln
            130                 135                 140

Thr Asn Val Ser Gln Ser Lys Asp Ser Asp Val Tyr Ile Thr Asp Lys
145                 150                 155                 160

Thr Val Leu Asp Met Arg Ser Met Asp Phe Lys Ser Asn Ser Ala Val
                165                 170                 175

Ala Trp Ser Asn Lys Ser Asp Phe Ala Cys Ala Asn Ala Phe Asn Asn
            180                 185                 190

Ser Ile Ile Pro Glu Asp Thr Phe Phe Pro Ser Pro Glu Ser Ser
            195                 200                 205

<210> SEQ ID NO 2
<211> LENGTH: 256
<212> TYPE: PRT
<213> ORGANISM: Homo sapiens

<400> SEQUENCE: 2

Met Ala Gly Ser His Met Gly Val Ser Gln Ser Pro Arg Tyr Lys Val
1               5                   10                  15

Ala Lys Arg Gly Gln Asp Val Ala Leu Arg Cys Asp Pro Ile Ser Gly
                20                  25                  30

His Val Ser Leu Phe Trp Tyr Gln Gln Ala Leu Gly Gln Gly Pro Glu
            35                  40                  45

Phe Leu Thr Tyr Phe Gln Asn Glu Ala Gln Leu Asp Lys Ser Gly Leu
        50                  55                  60

Pro Ser Asp Arg Phe Phe Ala Glu Arg Pro Glu Gly Ser Val Ser Thr
65                  70                  75                  80

Leu Lys Ile Gln Arg Thr Gln Gln Glu Asp Ser Ala Val Tyr Leu Cys
                85                  90                  95

Ala Ser Ser Leu Gly Gln Ala Tyr Glu Gln Tyr Phe Gly Pro Gly Thr
            100                 105                 110

Arg Leu Thr Val Thr Glu Asp Leu Lys Asn Val Phe Pro Pro Glu Val
            115                 120                 125

Ala Val Phe Glu Pro Ser Glu Ala Glu Ile Ser His Thr Gln Lys Ala
            130                 135                 140

Thr Leu Val Cys Leu Ala Thr Gly Phe Tyr Pro Asp His Val Glu Leu
145                 150                 155                 160

Ser Trp Trp Val Asn Gly Lys Glu Val His Ser Gly Val Ser Thr Asp
                165                 170                 175

Pro Gln Pro Leu Lys Glu Gln Pro Ala Leu Asn Asp Ser Arg Tyr Cys
            180                 185                 190

Leu Ser Ser Arg Leu Arg Val Ser Ala Thr Phe Trp Gln Asn Pro Arg
            195                 200                 205

Asn His Phe Arg Cys Gln Val Gln Phe Tyr Gly Leu Ser Glu Asn Asp
            210                 215                 220

Glu Trp Thr Gln Asp Arg Ala Lys Pro Val Thr Gln Ile Val Ser Ala
```

| | 225 | | | 230 | | | 235 | | | 240 | |
|---|---|---|---|---|---|---|---|---|---|---|---|
| Glu | Ala | Trp | Gly | Arg | Ala | Asp | Cys | Thr | Ser | Gly | Asp | Asp | Asp | Lys |
| | | | | 245 | | | | 250 | | | | 255 |

<210> SEQ ID NO 3
<211> LENGTH: 708
<212> TYPE: DNA
<213> ORGANISM: Mus. sp.

<400> SEQUENCE: 3

```
atggatttc aagtgcagat tttcagcttc ctgctaatca gtgcctcagt cataatatcc      60
agaggacaaa ttgttctcac ccagtctcca gcaatcatgt ctgcatctcc aggggagaag    120
gtcaccatga cctgcagtgc cagctcaagt gtaagttaca tgcactggta ccagcagaag    180
tcaggcacct cccccaaaag atggatttat gacacatcca actggcttc tggagtccct     240
gctcgcttca gtggcagtgg gtctgggacc tcttactctc tcacaatcag cagcatggag    300
gctgaagatg ctgccactta ttactgccag cagtggagta gtaacccatt cacgttcggc    360
tcggggacaa agttggaaat aaaacgggct gatgctgcac caactgtatc catcttccca    420
ccatccagtg agcagttaac atctggaggt gcctcagtcg tgtgcttctt gaacaacttc    480
taccccaaag acatcaatgt caagtggaag attgatggca gtgaacgaca aaatggcgtc    540
ctgaacagtt ggactgatca ggacagcaaa gacagcacct acagcatgag cagcaccctc    600
acgttgacca aggacgagta tgaacgacat aacagctata cctgtgaggc cactcacaag    660
acatcaactt cacccattgt caagagcttc aacaggaatg agtgttag              708
```

<210> SEQ ID NO 4
<211> LENGTH: 1782
<212> TYPE: DNA
<213> ORGANISM: Mus sp.

<400> SEQUENCE: 4

```
atggaaaggc actggatctt tctactcctg ttgtcagtaa ctgcaggtgt ccactcccag      60
gtccagctgc agcagtctgg ggctgaactg gcaagacctg ggcctcagt gaagatgtcc     120
tgcaaggctt ctggctacac ctttactagc tacacgatgc actgggtaaa acagaggcct    180
ggacagggtc tggaatggat tggatacatt aatcctagca gtggttatac taattacaat    240
cagaagttca aggacaaggc cacattgact gcagacaaat cctccagcac agcctacatg    300
caactgagca gcctgacatc tgaggactct gcagtctatt actgtgcaag atggagggac    360
gcgtactatg ctatggacta ctggggtcaa ggaacctcag tcaccgtctc ctcagagagt    420
cagtccttcc caaatgtctt cccctcgtc tcctgcgaga gccccctgtc tgataagaat    480
ctggtggcca tgggctgcct ggcccgggac ttcctgccca gcaccatttc cttcacctgg    540
aactaccaga acaacactga agtcatccag ggtatcagaa ccttcccaac actgaggaca    600
gggggcaagt acctagccac ctcgcaggtg ttgctgtctc caagagcat ccttgaaggt     660
tcagatgaat acctggtatg caaaatccac tacggaggca aaacagaga tctgcatgtg    720
cccattccag ctgtcgcaga gatgaacccc aatgtaaatg tgttcgtccc caccgggat    780
ggcttctctg ccctgcacc acgcaagtct aaactcatct gcgaggccac gaacttcact    840
ccaaaaccga tcagtatc ctggctaaag gatgggaagc tcgtggaatc tggcttcacc    900
acagatccgg tgaccatcga gaacaaagga tccacacccc aaacctacaa ggtcataagc    960
acacttacca tctctgaaat cgactggctg aacctgaatg tgtacacctg ccgtgtggat   1020
cacagggtc tcaccttctt gaagaacgtg tcctccacat gtgctgccag tccctccaca   1080
```

```
gacatcctaa ccttcaccat cccccctcc tttgccgaca tcttcctcag caagtccgct      1140
aacctgacct gtctggtctc aaacctggca acctatgaaa ccctgaatat ctcctgggct      1200
tctcaaagtg gtgaaccact ggaaaccaaa attaaaatca tggaaagcca tcccaatggc      1260
accttcagtg ctaagggtgt ggctagtgtt tgtgtggaag actggaataa caggaaggaa      1320
tttgtgtgta ctgtgactca cagggatctg ccttcaccac agaagaaatt catctcaaaa      1380
cccaatgagg tgcacaaaca tccacctgct gtgtacctgc tgccaccagc tcgtgagcaa      1440
ctgaacctga gggagtcagc cacagtcacc tgcctggtga agggcttctc tcctgcagac      1500
atcagtgtgc agtggcttca gagagggcaa ctcttgcccc aagagaagta tgtgaccagt      1560
gccccgatgc cagagcctgg ggccccaggc ttctacttta cccacagcat cctgactgtg      1620
acagaggagg aatggaactc cggagagacc tatacctgtg ttgtaggcca cgaggccctg      1680
ccacacctgg tgaccgagag gaccgtggac aagtccactg gtaaacccac actgtacaat      1740
gtctccctga tcatgtctga cacaggcggc acctgctatt ga                         1782

<210> SEQ ID NO 5
<211> LENGTH: 480
<212> TYPE: DNA
<213> ORGANISM: Mus sp.

<400> SEQUENCE: 5
atgaagaccc acctgcttct ctggggagtc ctggccattt ttgttaaggc tgtccttgta       60
acaggtgacg acgaagcgac cattcttgct gacaacaaat gcatgtgtac ccgagttacc      120
tctaggatca tcccttccac cgaggatcct aatgaggaca ttgtggagag aaatatccga      180
attgttgtcc ctttgaacaa cagggagaat atctctgatc ccacctcccc actgagaagg      240
aactttgtat accatttgtc agacgtctgt aagaaatgcg atcctgtgga gtggagctg      300 gaagatcagg ttgttactgc cacccagagc aacatctgca atgaagacga tggtgttcct      360
gagacctgct acatgtatga cagaaacaag tgctatacca ctatggtccc acttaggtat      420
catggtgaga ccaaaatggt gcaagcagcc ttgaccccg attcttgcta ccctgactag      480

<210> SEQ ID NO 6
<211> LENGTH: 235
<212> TYPE: PRT
<213> ORGANISM: Mus sp.

<400> SEQUENCE: 6

Met Asp Phe Gln Val Gln Ile Phe Ser Phe Leu Leu Ile Ser Ala Ser
1               5                   10                  15

Val Ile Ile Ser Arg Gly Gln Ile Val Leu Thr Gln Ser Pro Ala Ile
                20                  25                  30

Met Ser Ala Ser Pro Gly Glu Lys Val Thr Met Thr Cys Ser Ala Ser
            35                  40                  45

Ser Ser Val Ser Tyr Met His Trp Tyr Gln Gln Lys Ser Gly Thr Ser
        50                  55                  60

Pro Lys Arg Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Trp
            100                 105                 110

Ser Ser Asn Pro Phe Thr Phe Gly Ser Gly Thr Lys Leu Glu Ile Lys
        115                 120                 125
```

```
Arg Ala Asp Ala Ala Pro Thr Val Ser Ile Phe Pro Pro Ser Ser Glu
        130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
        210                 215                 220

Pro Ile Val Lys Ser Phe Asn Arg Asn Glu Cys
225                 230                 235
```

<210> SEQ ID NO 7
<211> LENGTH: 593
<212> TYPE: PRT
<213> ORGANISM: Mus sp.

<400> SEQUENCE: 7

```
Met Glu Arg His Trp Ile Phe Leu Leu Leu Ser Val Thr Ala Gly
1                5                  10                  15

Val His Ser Gln Val Gln Leu Gln Gln Ser Gly Ala Glu Leu Ala Arg
            20                  25                  30

Pro Gly Ala Ser Val Lys Met Ser Cys Lys Ala Ser Gly Tyr Thr Phe
        35                  40                  45

Thr Ser Tyr Thr Met His Trp Val Lys Gln Arg Pro Gly Gln Gly Leu
    50                  55                  60

Glu Trp Ile Gly Tyr Ile Asn Pro Ser Ser Gly Tyr Thr Asn Tyr Asn
65                  70                  75                  80

Gln Lys Phe Lys Asp Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Trp Arg Asp Ala Tyr Tyr Ala Met Asp Tyr Trp
        115                 120                 125

Gly Gln Gly Thr Ser Val Thr Val Ser Ser Glu Ser Gln Ser Phe Pro
    130                 135                 140

Asn Val Phe Pro Leu Val Ser Cys Glu Ser Pro Leu Ser Asp Lys Asn
145                 150                 155                 160

Leu Val Ala Met Gly Cys Leu Ala Arg Asp Phe Leu Pro Ser Thr Ile
                165                 170                 175

Ser Phe Thr Trp Asn Tyr Gln Asn Asn Thr Glu Val Ile Gln Gly Ile
            180                 185                 190

Arg Thr Phe Pro Thr Leu Arg Thr Gly Gly Lys Tyr Leu Ala Thr Ser
        195                 200                 205

Gln Val Leu Leu Ser Pro Lys Ser Ile Leu Glu Gly Ser Asp Glu Tyr
    210                 215                 220

Leu Val Cys Lys Ile His Tyr Gly Gly Lys Asn Arg Asp Leu His Val
225                 230                 235                 240

Pro Ile Pro Ala Val Ala Glu Met Asn Pro Asn Val Asn Val Phe Val
                245                 250                 255

Pro Pro Arg Asp Gly Phe Ser Gly Pro Ala Pro Arg Lys Ser Lys Leu
            260                 265                 270
```

```
Ile Cys Glu Ala Thr Asn Phe Thr Pro Lys Pro Ile Thr Val Ser Trp
            275                 280                 285

Leu Lys Asp Gly Lys Leu Val Glu Ser Gly Phe Thr Thr Asp Pro Val
    290                 295                 300

Thr Ile Glu Asn Lys Gly Ser Thr Pro Gln Thr Tyr Lys Val Ile Ser
305                 310                 315                 320

Thr Leu Thr Ile Ser Glu Ile Asp Trp Leu Asn Leu Asn Val Tyr Thr
                325                 330                 335

Cys Arg Val Asp His Arg Gly Leu Thr Phe Leu Lys Asn Val Ser Ser
            340                 345                 350

Thr Cys Ala Ala Ser Pro Ser Thr Asp Ile Leu Thr Phe Thr Ile Pro
        355                 360                 365

Pro Ser Phe Ala Asp Ile Phe Leu Ser Lys Ser Ala Asn Leu Thr Cys
    370                 375                 380

Leu Val Ser Asn Leu Ala Thr Tyr Glu Thr Leu Asn Ile Ser Trp Ala
385                 390                 395                 400

Ser Gln Ser Gly Glu Pro Leu Glu Thr Lys Ile Lys Ile Met Glu Ser
                405                 410                 415

His Pro Asn Gly Thr Phe Ser Ala Lys Gly Val Ala Ser Val Cys Val
            420                 425                 430

Glu Asp Trp Asn Asn Arg Lys Glu Phe Val Cys Thr Val Thr His Arg
        435                 440                 445

Asp Leu Pro Ser Pro Gln Lys Lys Phe Ile Ser Lys Pro Asn Glu Val
    450                 455                 460

His Lys His Pro Pro Ala Val Tyr Leu Leu Pro Pro Ala Arg Glu Gln
465                 470                 475                 480

Leu Asn Leu Arg Glu Ser Ala Thr Val Thr Cys Leu Val Lys Gly Phe
                485                 490                 495

Ser Pro Ala Asp Ile Ser Val Gln Trp Leu Gln Arg Gly Gln Leu Leu
            500                 505                 510

Pro Gln Glu Lys Tyr Val Thr Ser Ala Pro Met Pro Glu Pro Gly Ala
    515                 520                 525

Pro Gly Phe Tyr Phe Thr His Ser Ile Leu Thr Val Thr Glu Glu Glu
    530                 535                 540

Trp Asn Ser Gly Glu Thr Tyr Thr Cys Val Val Gly His Glu Ala Leu
545                 550                 555                 560

Pro His Leu Val Thr Glu Arg Thr Val Asp Lys Ser Thr Gly Lys Pro
                565                 570                 575

Thr Leu Tyr Asn Val Ser Leu Ile Met Ser Asp Thr Gly Gly Thr Cys
            580                 585                 590

Tyr
```

<210> SEQ ID NO 8
<211> LENGTH: 159
<212> TYPE: PRT
<213> ORGANISM: Mus sp.

<400> SEQUENCE: 8

```
Met Lys Thr His Leu Leu Leu Trp Gly Val Leu Ala Ile Phe Val Lys
1               5                   10                  15

Ala Val Leu Val Thr Gly Asp Asp Glu Ala Thr Ile Leu Ala Asp Asn
                20                  25                  30

Lys Cys Met Cys Thr Arg Val Thr Ser Arg Ile Ile Pro Ser Thr Glu
            35                  40                  45
```

-continued

Asp Pro Asn Glu Asp Ile Val Glu Arg Asn Ile Arg Ile Val Val Pro
         50                  55                  60

Leu Asn Asn Arg Glu Asn Ile Ser Asp Pro Thr Ser Pro Leu Arg Arg
 65                  70                  75                  80

Asn Phe Val Tyr His Leu Ser Asp Val Cys Lys Lys Cys Asp Pro Val
                     85                  90                  95

Glu Val Glu Leu Glu Asp Gln Val Val Thr Ala Thr Gln Ser Asn Ile
                100                 105                 110

Cys Asn Glu Asp Asp Gly Val Pro Glu Thr Cys Tyr Met Tyr Asp Arg
            115                 120                 125

Asn Lys Cys Tyr Thr Thr Met Val Pro Leu Arg Tyr His Gly Glu Thr
        130                 135                 140

Lys Met Val Gln Ala Ala Leu Thr Pro Asp Ser Cys Tyr Pro Asp
145                 150                 155

<210> SEQ ID NO 9
<211> LENGTH: 253
<212> TYPE: PRT
<213> ORGANISM: Artificial Sequence
<220> FEATURE:
<223> OTHER INFORMATION: TOL101 ScFV

<400> SEQUENCE: 9

Gln Val Gln Leu Gln Gln Ser Gly Ala Glu Leu Ala Arg Pro Gly Ala
1               5                  10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Tyr Thr Asn Tyr Asn Gln Lys Phe
    50                  55                  60

Lys Asp Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Tyr Cys
                85                  90                  95

Ala Arg Trp Arg Asp Ala Tyr Tyr Ala Met Asp Tyr Trp Gly Gln Gly
            100                 105                 110

Thr Ser Val Thr Val Ser Ser Gly Gly Gly Ser Gly Gly Gly Gly
        115                 120                 125

Ser Gly Gly Gly Gly Ser Gly Gly Gly Ser Gln Ile Val Leu Thr
    130                 135                 140

Gln Ser Pro Ala Ile Met Ser Ala Ser Pro Gly Glu Lys Val Thr Met
145                 150                 155                 160

Thr Cys Ser Ala Ser Ser Val Ser Tyr Met His Trp Tyr Gln Gln
                165                 170                 175

Lys Ser Gly Thr Ser Pro Lys Arg Trp Ile Tyr Asp Thr Ser Lys Leu
            180                 185                 190

Ala Ser Gly Val Pro Ala Arg Phe Ser Gly Ser Gly Ser Gly Thr Ser
        195                 200                 205

Tyr Ser Leu Thr Ile Ser Ser Met Glu Ala Glu Asp Ala Ala Thr Tyr
    210                 215                 220

Tyr Cys Gln Gln Trp Ser Ser Asn Pro Phe Thr Phe Gly Ser Gly Thr
225                 230                 235                 240

Lys Leu Glu Ile Lys Arg Ala His His His His His
                245                 250

ANTIBODY FOR SELECTIVE INHIBITION OF T-CELL RESPONSES

CROSS REFERENCE TO RELATED APPLICATIONS

This application claims priority to U.S. Provisional Patent Application Nos. 61/555,335 (filed Nov. 3, 2011); 61/555,344 (filed Nov. 3, 2011); 61/589,715 (filed Jan. 23, 2012); 61/610,348 (filed Mar. 13, 2012); and 61/654,631 (filed Jun. 1, 2012), the entire contents of each of which is incorporated herein by reference in its entirely.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: TLRA_001_01US_SeqList_ST25.txt, date recorded: Nov. 5, 2012, file size 20 kilobytes).

FIELD

The present invention relates to antibodies and methods for selectively inhibiting (TCR+) T-cell immune responses. In particular, the present invention relates to treatment of transplant rejection, autoimmune diseases, and inflammatory diseases using anti-$\alpha\beta$ TCR antibodies and antibody fragments. Methods and assays for identifying modulators of (TCR+) T-cell immune responses are also described. In some embodiments, the anti-$\alpha\beta$ TCR antibodies are TOL101 monoclonal antibodies, TOL101 chimeric antibodies, TOL101 humanized antibodies or variants thereof.

BACKGROUND

The statements in this section merely provide background information related to the present disclosure and may not constitute prior art.

The T-cell receptor (TCR) is composed of at least 7 integral membrane proteins. On a majority of peripheral T-cells the TCR contains a clonally distributed disulphide linked heterodimer consisting of an $\alpha$ TCR chain and $\alpha\beta$ TCR chain. These clonotypic chains are subdivided into variable (V), joining (J) and constant (C) segments for the $\alpha$ chain and a Diversity (D) segment for the $\beta$ chain. Associated with the $\alpha\beta$ TCR are three invariant chains that form the CD3 complex. The $\alpha\beta$ TCR is critical for antigen/MHC recognition while the CD3 proteins play an important role in signal transduction.

The structure of the $\alpha\beta$ TCR chains is similar to that of antibodies, with the variable regions resulting from genetic recombination, generating the large diversity of TCR repertoires. On the other hand, the constant and transmembrane regions of the $\alpha\beta$ TCR are conserved. These conserved regions are very important, as they play a role in the binding of the $\alpha$ and $\beta$ chains, interact with the CD3 proteins, and play a role in the transport of TCR components from the endoplasmic reticulum to the cell surface. Patients who have mutations within the constant region may have a poorly functioning $\alpha\beta$ TCR, but more commonly fail to express a TCR at all. Physiologically, patients with these mutations suffer from severe immunodeficiency. One recent study in the Journal of Clinical investigation showed in multiple patients that a genetic impairment at the last base of exon 3 immediately following the translational termination codon in the $\alpha$ TCR subunit constant gene resulted in severe immunodeficiency in infants, requiring lifelong antiviral and antibiotic prophylaxis (Morgan, et al., "Mutation in the TCR$\alpha$ subunit constant gene (TRAC) leads to a human immunodeficiency disorder characterized by a lack of TCR$\alpha\beta^+$ T-cells". J. Clin. Invest., February 2011).

In the absence of immunosuppressive intervention following allogeneic solid organ transplantation, donor and recipient antigen-presenting cells present graft antigens to alloreactive alpha-beta ($\alpha\beta$) T-cells, which, when activated, result in an inflammatory response and rapid rejection of the allograft. These T-cells, which include T-helper (CD4) and cytotoxic (CD8) T-cells, are critical in the acute organ transplant rejection response since they recognize allogeneic antigens, including major histocompatibility complex (MHC) antigens, as foreign. Gamma-delta ($\gamma\delta$) T-cells express the $\gamma\delta$ T-cell receptor (TCR) and generally do not recognize protein antigens in the context of MHC but rather recognize unconventional, non-protein antigens. $\gamma\delta$ T-cells may be of benefit to renal transplant patients from several perspectives, including providing protection against a variety of microbial infections to which immune suppressed transplant patients are particularly vulnerable. Such infections include cytomegalovirus (CMV), a common viral infection in transplant patients that, through its immunosuppressive properties, can lead to other opportunistic infections as well as post-transplant lymphoproliferative disorders.

In mice and in humans, the presence of donor $\gamma\delta$ T-cells is associated with better outcomes in bone marrow transplant models, in part through prevention of graft-versus-host disease (GVHD), though the mechanisms are not fully understood. One subset of $\gamma\delta$ T-cells is a rare population in the peripheral blood of normal humans and the majority of liver transplant patients, but expands to a higher frequency compared to other $\gamma\delta$ T-cell subsets in the peripheral blood of "operationally tolerant" liver transplant patients. These patients are considered "operationally tolerant" because they have achieved a level of tolerance to the allograft that allows total removal from immunosuppression. This expanded subset of $\gamma\delta$ T-cells is the same one that is associated with tolerance to semi-allogeneic antigens in pregnant individuals, indicating that these cells may have an important role in the generation and/or maintenance of tolerance against allogeneic antigens. In addition, a reduction in peripheral $\gamma\delta$ T-cells is associated with acute and chronic renal allograft rejection, while stable, non-rejecting kidney transplant patients have a higher percentage of $\gamma\delta$ T-cells, on average. Together, these studies indicate that an immunosuppressive agent that spares depletion or inactivation of $\gamma\delta$ T-cells may be associated with better outcomes.

An unmet medical need exists for an agent capable of selectively inactivating specific $\alpha\beta$ T-cells in a non-mitogenic manner, without unnecessarily exposing the patient to non-specific, long term, or open-ended immune suppression, which may exacerbate the risks of infections and malignancies. Gamma-delta T-cells are important mediators in the protection against infectious agents and share several features in common with $\alpha\beta$ T-cells, including the expression of CD25, CD52 and CD3. As such, currently used induction therapies, including Anti-thymocyte globulin (ATG), alemtuzumab, basiliximab and daclizumab, target not only altoreactive T-cells but also $\gamma\delta$ T-cells and NK cells. A more specific approach to prevention of acute organ rejection or to treat inflammatory or autoimmune diseases by targeting the $\alpha\beta$ TCR alone, sparing $\gamma\delta$ T-cells, may provide similar or better efficacy than the currently used T-cell targeting antibodies while carrying fewer risks in terms of development of opportunistic infections and malignancies. Although the development of some αβ TCR-specific antibodies has been attempted, none have exhibited both sufficient clinical efficacy and an acceptable safety profile. There is therefore a need for αβ TCR-specific antibodies that exhibit efficacy in diseases and conditions including inflammatory diseases, autoimmune diseases, and allograft rejection, while exhibiting minimal adverse effects.

SUMMARY

Unless otherwise defined, all technical and scientific terms used herein have the same meaning as commonly understood by one of ordinary skill in the art to which this present technology belongs. Although methods and materials similar or equivalent to those described herein can be used in the practice or testing of the present technology, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The present invention provides compositions, methods, and assays for treating an inflammatory and/or autoimmune disease, and/or transplanted tissue rejection using anti-αβ TCR antibodies and antibody fragments. In certain embodiments, the present invention provides methods for treating an autoimmune disease, with only a single dose of an anti-αβ TCR antibody per day. In some embodiments, the anti-αβ TCR antibodies of the present invention are TOL101 monoclonal antibodies, TOL101 chimeric antibodies, TOL101 humanized antibodies, or variants thereof. TOL101 monoclonal antibodies are mouse monoclonal IgM antibodies which bind to a human αβ TCR and are produced by a hybridoma that is designated TOL101 Master Cell Bank (MCB). The TOL101 MCB hybridoma, which produces TOL101, was deposited on Nov. 2, 2012 at the American Type Culture Collection (ATCC), 10801 University Boulevard, Manassas, Va. 20110-2209, under the provisions of the Budapest Treaty on the International Recognition of the Deposit of Microorganisms for the Purpose of Patent Procedures, and assigned ATCC accession number PTA-13293.

In one aspect, the present invention provides an isolated hybridoma cell line that produces an antibody or antigen binding fragment thereof that binds αβ TCR. In one embodiment, the hybridoma cell line is TOL101 MCB. In other aspects, the present invention provides an isolated antibody, or antigen binding fragment thereof, that binds to the αβ TCR and is glycosylated at equivalent or corresponding amino acid residues as the antibody produced by the hybridoma TOL101 MCB. In another embodiment of the invention, the isolated antibody or antigen binding fragment thereof is TOL101 or a fragment thereof, which is produced by the hybridoma TOL101 MCB.

In one embodiment, the isolated antibody or fragment thereof of the invention does not induce production of a cytokine upon binding to the αβ TCR on a T cell. In a further embodiment, the isolated antibody or fragment thereof of the invention does not induce production of Tumor Necrosis Factor-alpha (TNF-α), Interferon-gamma (IFN-γ), interleukin-2 and/or Interleukin-6 upon binding to the αβ TCR on a T cell. In another embodiment, the isolated antibody or fragment thereof of the invention does not produce levels of cytokines associated with cytokine release syndrome upon binding to the αβ TCR on a T cell. In a further embodiment, the cytokines associated with cytokine release syndrome are TNF-α, IFN-γ, interleukin-2 and/or Interleukin-6. In another embodiment, the isolated antibody or fragment thereof of the invention induces the production of less than 500 pg/mL of TNF-α upon binding to αβ TCR on a T cell. In another embodiment, the isolated antibody or fragment thereof of the invention induces the production of less than 500 pg/mL of IFN-γ upon binding to αβ TCR on a T cell. In another embodiment, the isolated antibody or fragment thereof of the invention induces the production of less than 500 pg/mL of Interleukin-2 upon binding to αβ TCR on a T cell. In another embodiment, the isolated antibody or fragment thereof of the invention induces the production of less than 500 pg/mL of Interleukin-6 upon binding to αβ TCR on a T cell, in another embodiment, the isolated antibody or fragment thereof of the invention binds to αβ TCR on a T cell, wherein the antibody binds to αβ TCR and reduces the surface expression of αβ TCR and CD3 on the T cell, and wherein the antibody does not deplete T cells. In another embodiment, the isolated antibody or fragment thereof of the invention induces phosphorylation of AKT or ERK upon binding the αβ TCR. In another embodiment, the isolated antibody or fragment thereof of the invention induces calcium flux in less than 60% of αβ TCR+ T cells. In a further embodiment, the antibody or fragment thereof induces calcium flux in less than 50% of αβ TCR+ T cells. In a further embodiment, the antibody or fragment thereof induces calcium flux in less than 40% of αβ TCR+ T cells. In a further embodiment, the antibody or fragment thereof induces calcium flux in less than 30% of αβ TCR+ T cells. In a further embodiment, the antibody or fragment thereof induces calcium flux in less than 20% of αβ TCR+ T cells. In a further embodiment, the antibody or fragment thereof induces calcium flux in less than 15% of αβ TCR+ T cells. In a still further embodiment, the antibody or fragment thereof induces calcium flux in less than 10% of αβ TCR+ T cells. In another embodiment, the isolated antibody or fragment thereof of the invention reduces the binding of other antibodies specific for the αβ TCR, including IP26, 3a8, and T10B9. In one embodiment, the antibody or fragment thereof reduces the binding of monoclonal antibody T10B9, 3a8, or IP26 to the αβ TCR by about 10% to about 100%, in a further embodiment, the antibody or fragment thereof reduces the binding of monoclonal antibody T10B9, 3a8, or IP26 to the αβ TCR by about 40% to about 90%. In a still further embodiment, the antibody or fragment thereof reduces the binding of monoclonal antibody T10B9, 3a8, or IP26 to the αβ TCR by about 60% to about 80%. In a yet further embodiment, the antibody or fragment thereof reduces the binding of monoclonal antibody T10B9, 3a8, or IP26 to the αβ TCR by at least 80%. In another embodiment, the isolated antibody or fragment thereof binds to αβ TCR on a T cell, wherein cross-linking of the antibody or fragment thereof does not induce proliferation of the T cell. As used herein, the term "cross-linking" refers to immobilizing the antibody, for example, on a solid phase plastic surface.

In one embodiment, the present invention provides an isolated antibody or antigen binding fragment thereof wherein the three light chain complementarity determining regions (CDRL1, CDRL2 and CDRL3) and the three heavy chain complementarity determining regions (CDRH1, CDRH2 and CDRH3) are the light and heavy chain complementarity determining regions of the antibody produced by the hybridoma TOL101 MCB. In another embodiment, the antibody or fragment thereof is encoded by a polynucleotide sequence comprising SEQ ID NOs: 3, 4, and 5. In another embodiment, the antibody or fragment thereof comprises an amino acid sequence according to SEQ ID NOs: 6, 7, and 8.

In some embodiments, the present invention provides an isolated antibody or antigen binding fragment thereof that binds to αβ TCR, wherein the antibody or antigen binding fragment thereof is a murine antibody, a chimeric antibody, a humanized antibody, an scFv, an Fab fragment, an Fab' fragment, and an F(ab)' fragment.

In one embodiment, the isolated antibody or antigen binding fragment thereof binds the αβ TCR and is coupled to a detectable label, including, but not limited to, a radioisotope, an enzyme, a fluorescent label, a luminescent label, a bioluminescent label, biotin or toxin.

In one embodiment, the isolated antibody or antigen binding fragment thereof of the invention binds the αβ TCR on a T cell and, following cross-linking of the antibody or antigen binding fragment does not induce proliferation of the T cell.

In one aspect, the present invention provides a method for treating, preventing the onset of ameliorating or reducing the symptoms of an inflammatory disease, autoimmune disease, or transplant tissue rejection comprising administering a therapeutically effective amount of an isolated antibody or antigen binding fragment thereof to a human patient in need thereof, wherein the antibody or fragment binds αβ TCR. In another aspect, the present invention provides a method of inhibiting a T cell immune response in order to treat, prevent the onset of, ameliorate, or reduce the symptoms of an inflammatory disease, an autoimmune disease, or a response against a transplanted tissue, comprising administering a therapeutically effective amount of an anti-αβ TCR antibody or antigen binding fragment thereof to a human patient in need thereof. Inflammatory diseases, autoimmune diseases, or transplanted tissue rejection that may be detected, diagnosed, treated, prognosed, ameliorated or monitored by the antibodies or fragments thereof of the invention include, but are not limited to: asthma, allergy, allergic airway inflammation, allergic encephalomyelitis, autoimmune arthritis, rheumatoid arthritis, Juvenile rheumatoid arthritis, reactive arthritis, psoriatic arthritis, sacroiliitis, isolated acute anterior uveitis, undifferentiated spondyloarthropathy, Type 1 Diabetes Mellitus, Multiple Sclerosis, Systemic Lupus Erythematosus, glomerulonephritis, Hashimoto's thyroiditis, Graves' disease, Scleroderma, Celiac disease, Crohn's disease, inflammatory bowel disease, ulcerative colitis, ankylosing spondylitis, Sjogren's syndrome, psoriasis, contact dermatitis, Goodpasture's syndrome, Addison's disease, Wegener's granulomatosis, Primary biliary cirrhosis, Sclerosing cholangitis, Autoimmune hepatitis, Polymyalgia Rheumatica, Bechet's disease, Guillain-Barre syndrome, various vasculitides, uveoretinitis, thyroditis, myasthenia gravis, immunoglobulin nephropathies, myocarditis, progressive systemic sclerosis, organ graft rejection, mixed connective tissue rejection, and graft-versus-host disease.

In one embodiment, the antibody or antigen binding fragment thereof of the invention binds the αβ TCR and induces a Human anti-mouse antibody (HAMA) response in fewer than 20% of the human patients administered the antibody or fragment thereof as measured by Enzyme Linked Immunosorbent Assay (ELISA). In a further embodiment, the antibody or antigen binding fragment thereof binds the αβ TCR and induces a HAMA response in fewer than 10% or 5% of the human patients administered the antibody or fragment thereof as measured by ELISA.

In one embodiment, the present invention also provides a method of producing an isolated antibody or fragment thereof comprising transfecting a mammalian host cell with a polynucleotide sequence encoding an antibody or fragment thereof comprising the six complementarity determining regions (CDR1, CDR2, and CDR3) of the light and heavy chain of the antibody produced by the hybridoma TOL101 MCB; culturing the host cell; and isolating the antibody or fragment thereof produced by the host cell which binds to αβ TCR. In one embodiment, the antibody or fragment thereof produced by this method reduces surface expression of αβ TCR and CD3 on the T cell, and does not deplete T cells. In another embodiment, the isolated antibody or fragment thereof produced by this method is encoded by a polynucleotide sequence comprising SEQ ID NOs: 3 and 4. In a further embodiment, the polynucleotide sequence further comprises SEQ ID NO: 5. In a still further embodiment, the isolated antibody produced by this method is TOL101.

In another aspect, the present invention provides a method for identifying a therapeutic compound that represses TCR+ T-cell activation. In a further embodiment, the method includes the steps of: (a) contacting a αβ T-cell receptor (4 TCR) or fragment thereof with an anti-αβ TCR antibody or antibody fragment thereof under conditions operable to form a TCR-anti-αβ TCR complex; (b) contacting the TCR-anti-αβ TCR complex; with a candidate compound; (c) determining the ability of the candidate compound to modulate the binding of the anti-αβ TCR antibody or antibody fragment thereof to the TCR or fragment thereof, and (d) determining whether said candidate compound activates a resting T-cell in the presence of an anti-CD3 antibody, wherein modulation of the binding of said anti-αβ TCR antibody or antibody fragment thereof to said TCR or fragment thereof and failure to activate a resting T-cell indicates that said candidate compound is a therapeutic compound. In a further aspect, the present invention includes a method for treating an inflammatory disease, an autoimmune disease, or a transplanted tissue rejection, the method includes the step: administering an anti-αβ TCR antibody or antibody fragment thereof in an amount from about 14 mg/day to about 52 mg/day to a subject in need thereof wherein the antibody is produced from the hybridoma TOL101 MCB.

In one embodiment, the present invention provides a method for treating an autoimmune disease, inflammatory disease, or transplant tissue rejection, comprising administering an αβ TCR antibody or antigen binding fragment thereof in an amount from about 7 mg/day to about 58 mg/day to a subject in need thereof in a further embodiment, the anti-αβ TCR antibody or antigen binding fragment thereof is produced from the hybridoma TOL101 MCB. In a further embodiment, the anti-αβ TCR antibody or fragment thereof is administered in an amount of 7 mg/day, 14 mg/day, 21 mg/day, 28 mg/day, 30 mg/day, 32 mg/day, 34 mg/day, 35 mg/day, 36 mg/day, 38 mg/day, 40 mg/day, 42 mg/day, 44 mg/day, 46 mg/day, 48 mg/day, 50 mg/day, 52 mg/day, 54 mg/day, 56 mg/day or 58 mg/day, or combinations thereof.

In one embodiment, the present invent on provides a method for treating an autoimmune disease, inflammatory disease, or transplant tissue rejection, comprising administering an αβ TCR antibody or antigen binding fragment thereof in a dosing schedule comprising 14 mg at day 1, 21 mg at day 2, 28mer at day 3, 42 mg at day 4, and 42mer at day 5. In a further embodiment, the antibody or fragment thereof is administered in a dosing schedule comprising 14 mg at day 1, 21 mg at day 2, 28 mg at day 3, 42 mg at day 4, 42 mg at day 5, and 42 mg at day 6. In one embodiment, the αβ TCR antibody or antigen binding fragment thereof is administered once per day.

In one aspect, the present invention provides a method for induction of regulatory T cells (Tregs) in a subject in need thereof, comprising administering an αβ TCR antibody or antigen binding fragment thereof in a dosing schedule comprising 14 mg at day 1, 21 mg at day 2, 28 mg at day 3, 42 mg at day 4, and 42 mg at day 5. In a further embodiment, the antibody or fragment thereof is administered in a dosing schedule comprising 14 mg at day 1, 21 mg at day 2, 28 mg at day 3, 42 mg at day 4, 42 mg at day 5, and 42 mg at day 6. In one embodiment, the concentration of Tregs per milliliter of whole blood present in the subject is determined prior to commencing the dosing schedule to obtain a baseline level of Tregs per milliliter of whole blood in the subject. In some embodiments, Tregs are phenotypically CD2+ CD25+ FOXP3+ CD127lo Tregs. In some embodiments, the number of Tregs is determined using specific cell surface markers and flow cytometry. In some embodiments, a method of inducing Tregs is provided wherein the subject is in need of inhibiting alloreactive T-cells, or inhibiting cytotoxic T-cell (CTL) activity, or immunosuppressing an alloresponse, or inhibiting an autoimmune response, or inhibiting, preventing or blocking an alloresponse or an autoimmune response prior to, during or subsequent to tissue transplantation, or inhibiting, suppressing or blocking graft vs. host disease, or preventing, treating or suppressing an autoimmune response in an inflammatory disease, or autoimmune disease.

The details of one or more embodiments of the present invention are set forth in the accompanying figures and the description below. Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 16 depicts a protocol for treatment of renal transplant recipients using TOL101 and corresponding clinical endpoints.

FIG. 31A-E are line graphs demonstrating the levels of TNF (panel A), IFN-γ (panel B), IL6 (panel C), IL1β (panel D), and IL2 (panel E) in TOL101 treated human clinical trial subjects. FIG. 31F is a bar graph demonstrating the level of Human Anti-Mouse Antibody (HAMA) induction in the TOL101 Phase 2 clinical trial.

FIG. 32 is a listing of the CD3 counts from patients enrolled in the TOL101 Phase 2 clinical study.

Figure 33:
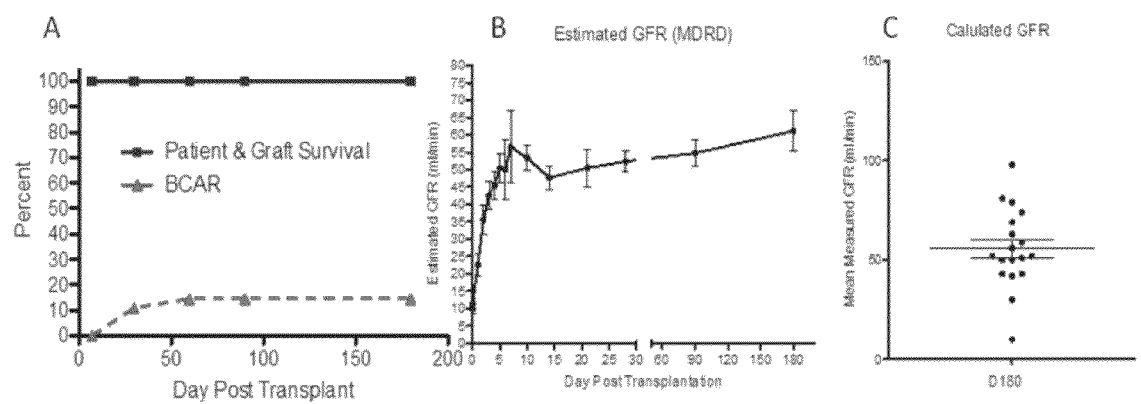

FIG. 33 A-C depict efficacy measures from the Phase 2 TOL101 clinical study. Panel A is a line graph depicting biopsy proven acute rejection rates as well as patient and graft survival (commonly refereed to as the transplant triple endpoint). Panel B is a line graph showing the estimated glomerular filtration rate. Panel C is a cluster graph showing the measured glomerular filtration rate from patients in the TOL101 Phase 2 study.

Figure 34:
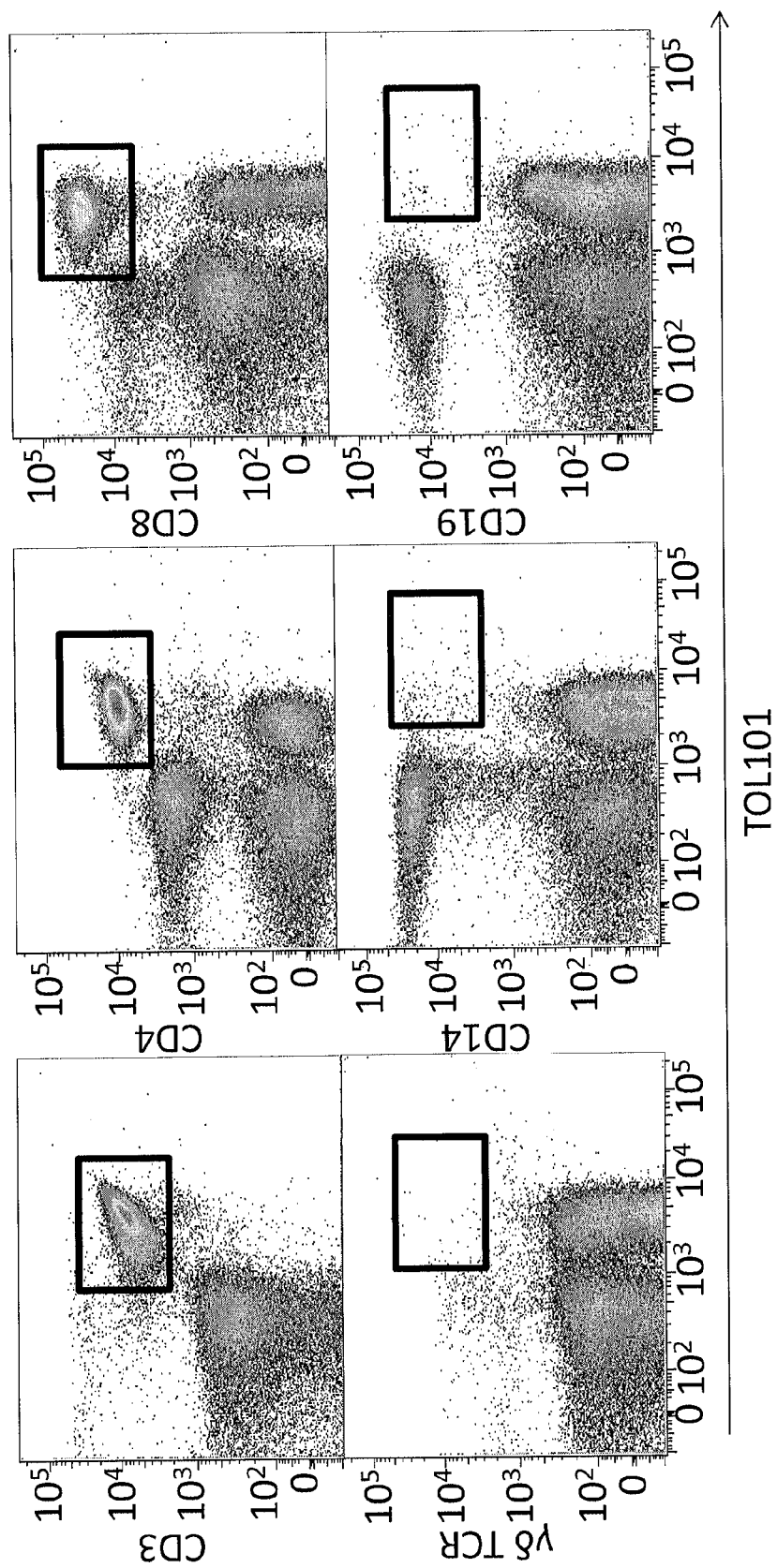

FIG. 34 depicts a set of flow cytometry dot plots and histograms showing the specificity of TOL101 to the αβ TCR, indicating that the antibody binds to the alpha chain.

Figure 35:
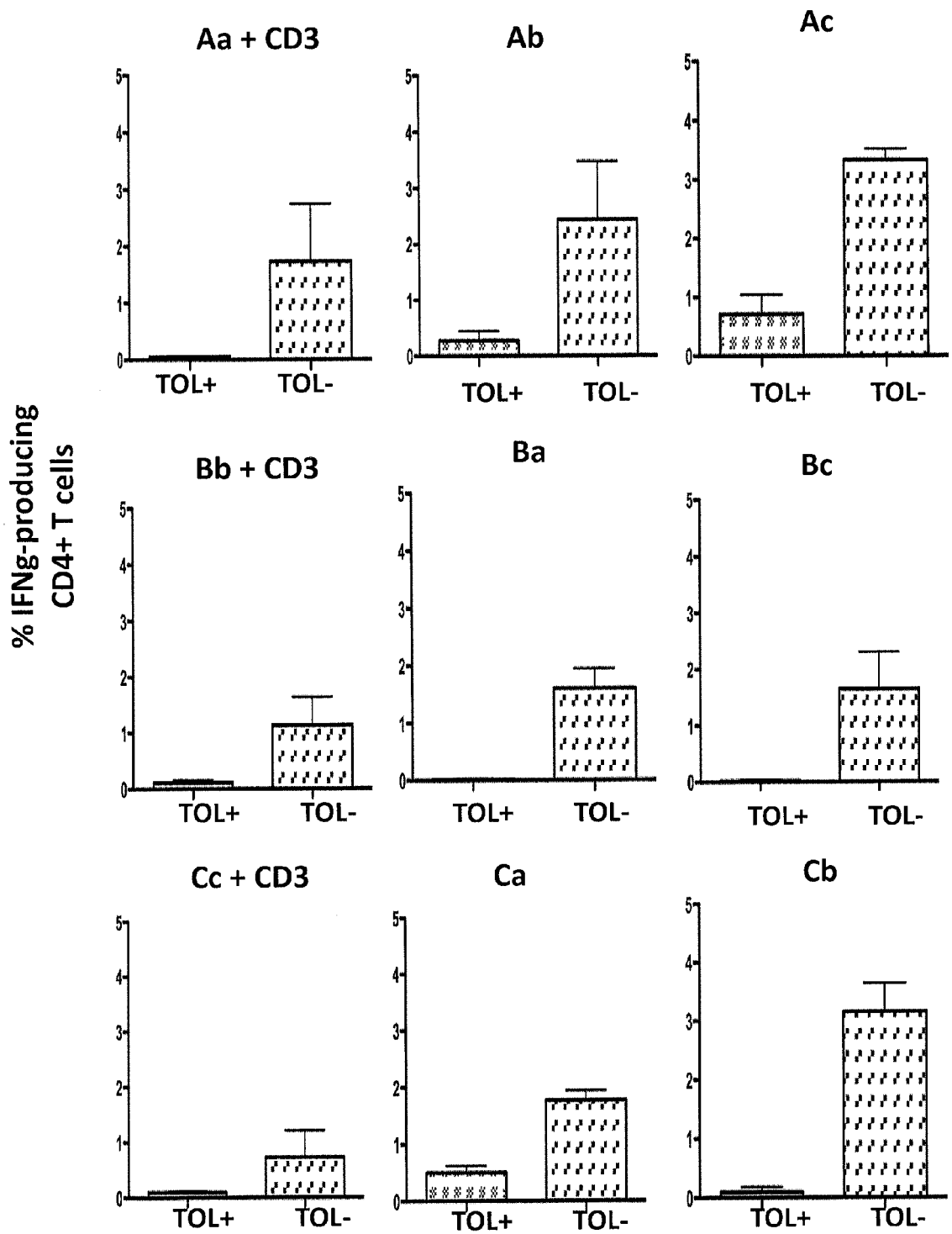

FIG. 35 depicts a set of bar graphs illustrating suppression of IFN-gamma by TOL101 in a one-way MLR.

Figure 36:
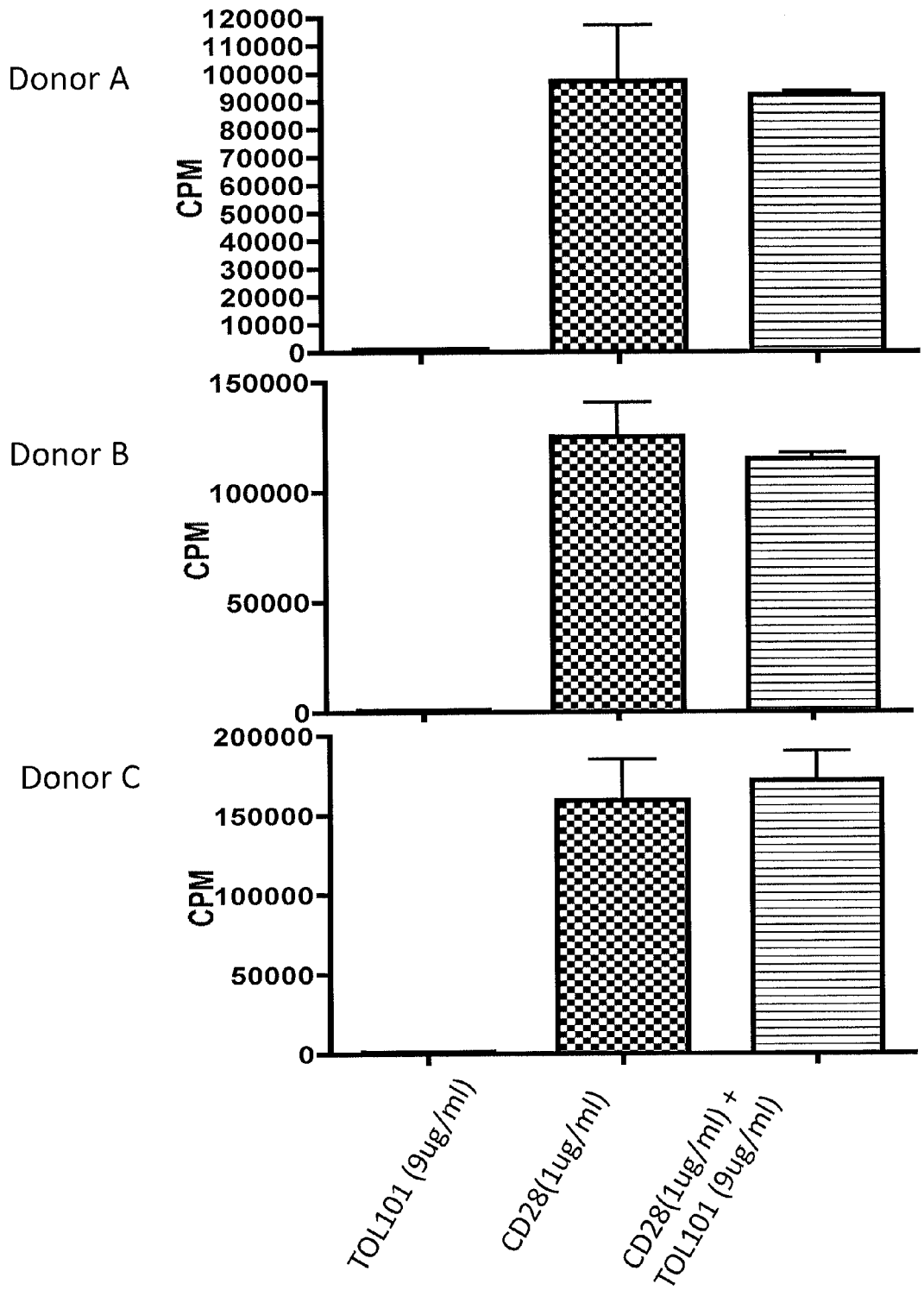

FIG. 36 shows that TOL101 does not modulate CD28-induced proliferation.

Figure 37:
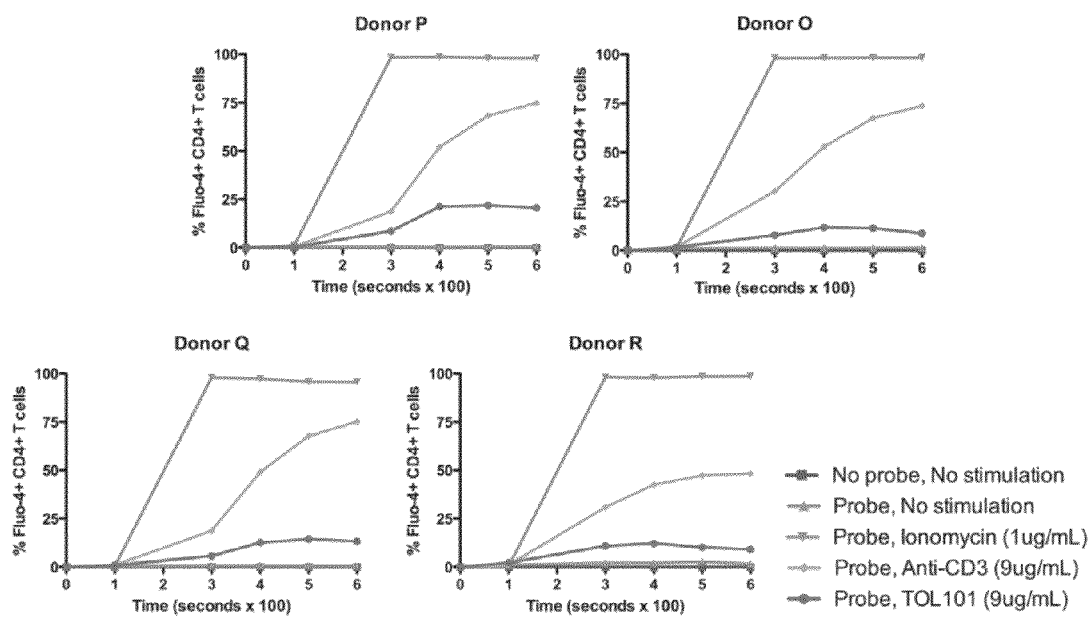

FIG. 37 depicts calcium flux in CD4 T cells stimulated with ionomycin, anti-CD3, or TOL101.

Figure 38:
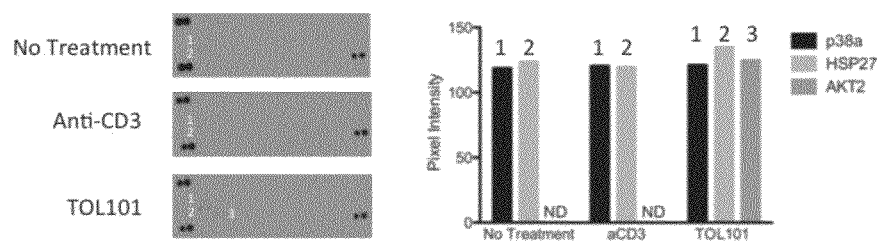

FIG. 38 depicts protein phosphorylation of heat shock protein 27, p38a MAPK protein activate kinase and AKT2 after TOL1.01 treatment as compared to anti-CD3 treatment and media controls. ND=not detected.

Figure 39A:
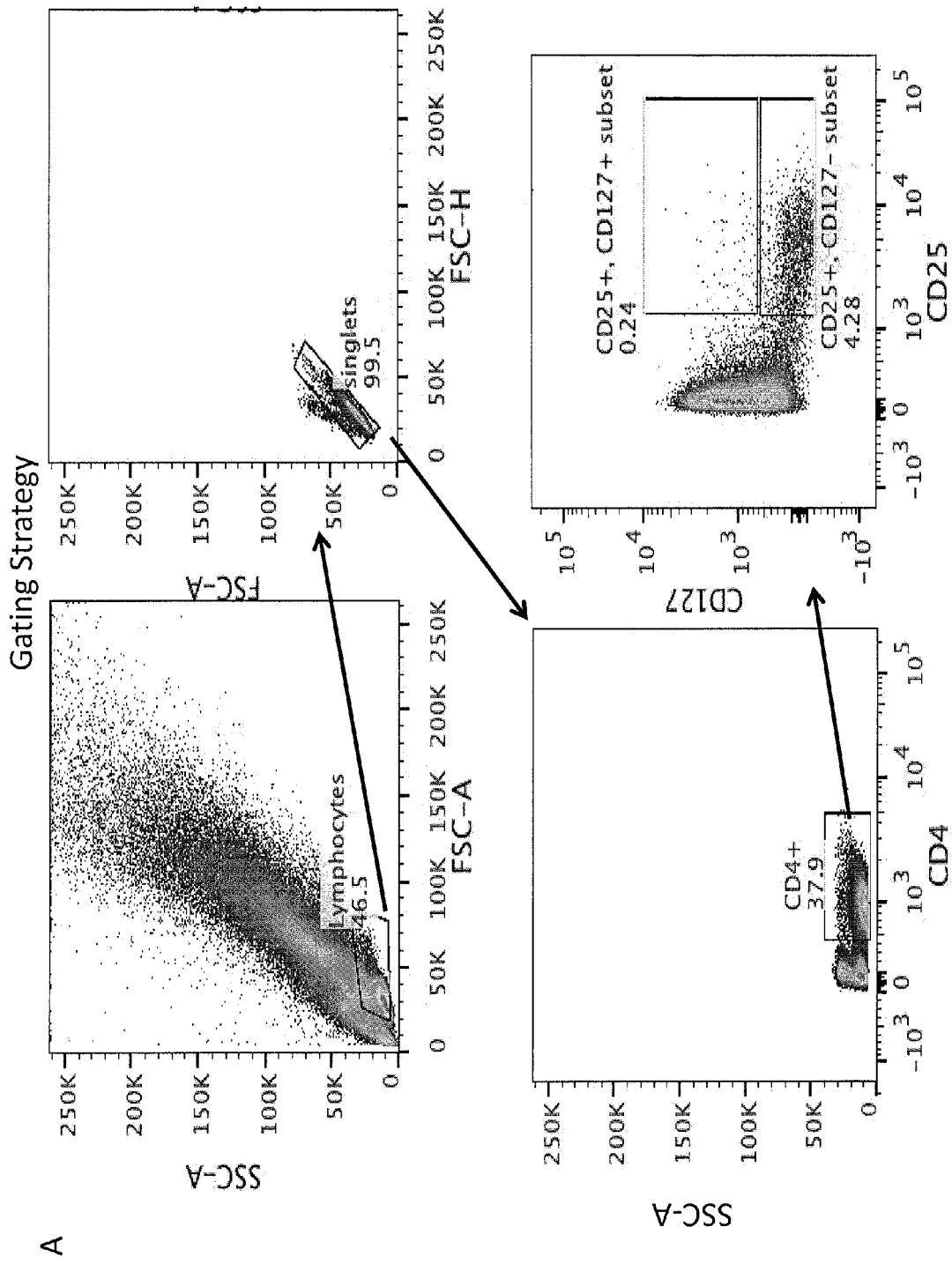
Figure 39B:
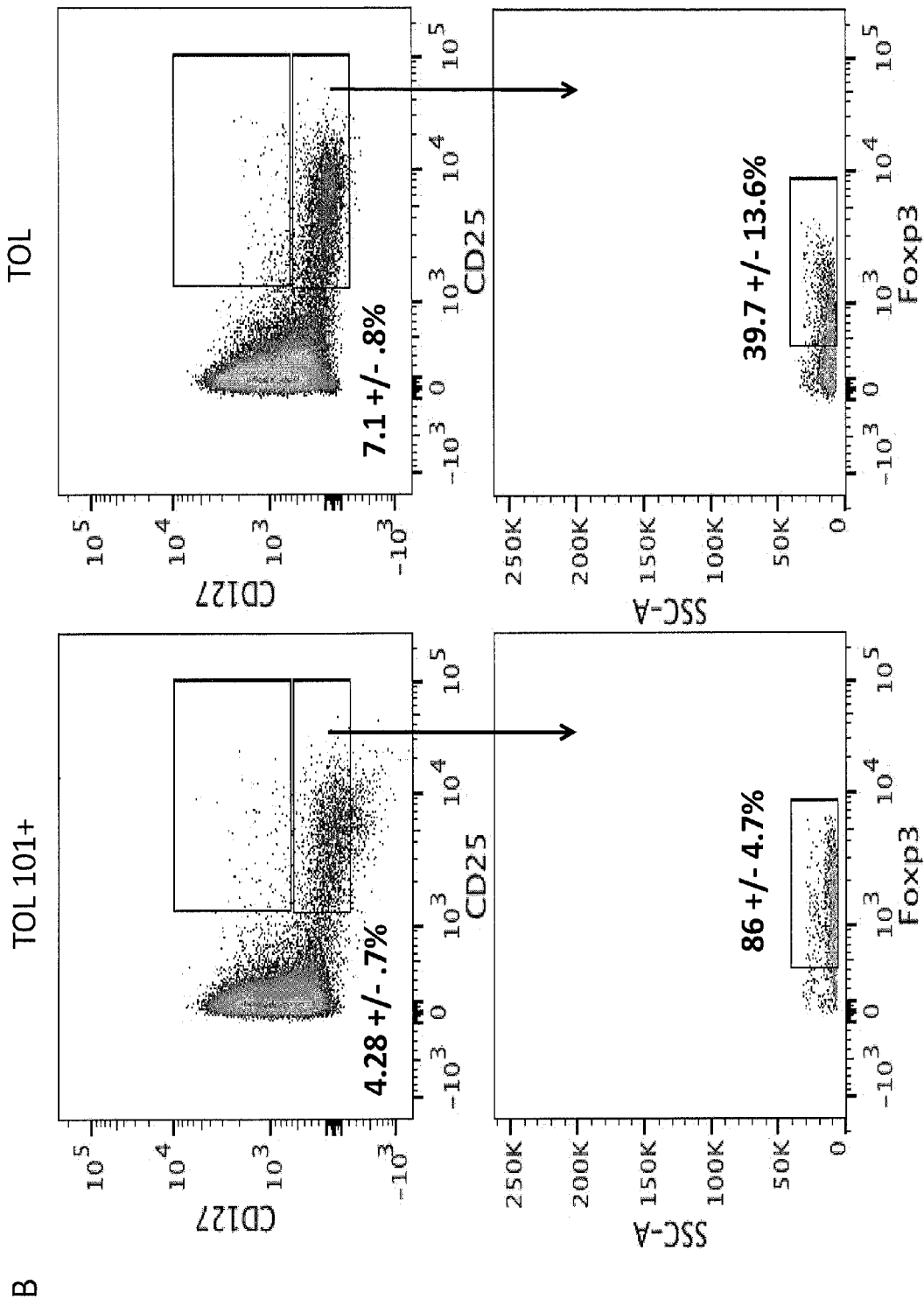
Figure 39C:
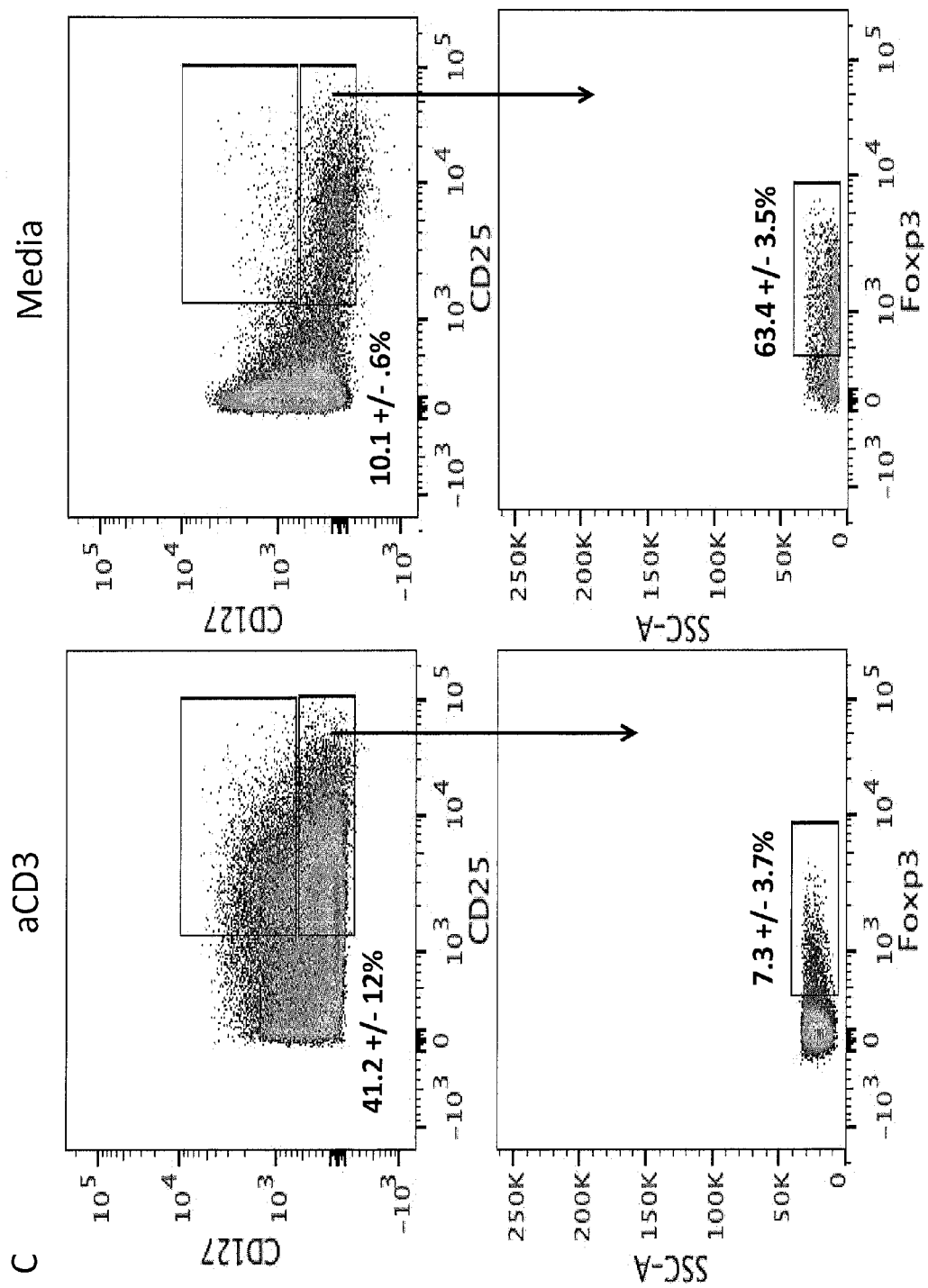

FIG. 39 depicts the gating strategy (FIG. 39A) and the induction of FoxP3 by TOL101 (FIG. 39B) in a two-way MLR. Positive (aCD3) and negative (media) controls are shown in FIG. 39C).

FIG. 40 shows the a schematic structure and the amino acid sequence (SEQ ID NO: 9) of a scFV derived from the TOL101 amino acid sequence (panel A); an SDS page of the scFV under reducing and non-reducing conditions (panel B); and flow cytometry showing the ability of the scFV to bind to CD8 and CD4 T cells (panel C).

DETAILED DESCRIPTION

The following description of technology is merely exemplary in nature of the subject matter, manufacture and use of one or more present inventions, and is not intended to limit the scope, application, or uses of any specific present technology claimed in this application or in such other applications as may be filed claiming priority to this application, or patents issuing therefrom. The following definitions and non-limiting guidelines must be considered in reviewing the description of the technology set forth herein.

The term "antibody," as used herein, is intended to refer to immunoglobulin molecules comprised of four polypeptide chains, two heavy (R) chains and two light (L) chains interconnected by disulfide bonds. Each heavy chain is comprised of a heavy chain variable region (abbreviated herein as HCVR or $V_H$) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, CL. The $V_H$ and $V_L$ regions can be further subdivided into regions of hypervariability, termed complementarity determining regions (CDRs), interspersed with regions that are more conserved, termed framework regions (FR). Each variable region ($V_H$ or $V_L$) contains 3 CDRs, designated CDR1, CDR2 and CDR3. Each variable region also contains 4 framework sub-regions, designated FR1, FR2, FR3 and FR4. The term antibody includes all types of antibodies, including, for example, IgG and IgM. In some embodiments, the antibodies are IgM and in some embodiments, the IgM form polymerized pentamers.

As used herein, the term "antibody fragments" and "antigen-binding fragment," in reference to an antibody, refers to a portion of an intact antibody that is able to bind the same antigen as the intact antibody. Examples of antibody fragments include, but are not limited to, linear antibodies, single-chain antibody molecules (scFv), Fv, Fab and F(ab')$_2$ fragments, and multispecific antibodies formed from antibody fragments. The antibody fragments preferably retain at least part of the heavy and/or light chain variable region.

The term "anti-αβ TCR antibody or antibody fragment" refers to an antibody or antibody fragment that binds the alpha chain of the human T-cell receptor, the beta chain of the human T-cell receptor, or both the alpha and beta chains of the human T-cell receptor.

As used herein, the phrase "TOL101 antibody" refers to a murine anti-αβ TCR monoclonal IgM antibody which binds to a human αβ TCR and is produced from the hybridoma TOL101 Master Cell Bank (MCB). As used herein, the term "master cell bank" refers to a culture of fully characterized cells processed together to ensure uniformity and stability. Typically, a MCB is a hybridoma cell line that is tested and determined to provide a stable and uniform source of a particular monoclonal antibody. TOL101 MCB was deposited on Nov. 2, 2012 at the ATCC and assigned ATCC accession number PTA-13293.

TOL101 has a Light chain encoded by the polynucleotide sequence of SEQ ID NO: 3:

```
ATGGATTTTCAAGTGCAGATTTTCAGCTTCCTGCTAATCAGTGCCTCAGTCATAATATCCAGAGGACAAA

TTGTTCTCACCCAGTCTCCAGCAATCATGTCTGCATCTCCAGGGGAGAAGGTCACCATGACCTGCAGTGC

CAGCTCAAGTGTAAGTTACATGCACTGGTACCAGCAGAAGTCAGGCACCTCCCCCAAAAGATGGATTTAT

GACACATCCAAACTGGCTTCTGGAGTCCCTGCTCGCTTCAGTGGCAGTGGGTCTGGGACCTCTTACTCTC

TCACAATCAGCAGCATGGAGGCTGAAGATGCTGCCACTTATTACTGCCAGCAGTGGAGTAGTAACCCATT

CACGTTCGGCTCGGGGACAAAGTTGGAAATAAAACGGGCTGATGCTGCACCAACTGTATCCATCTTCCCA

CCATCCAGTGAGCAGTTAACATCTGGAGGTGCCTCAGTCGTGTGCTTCTTGAACAACTTCTACCCCAAAG

ACATCAATGTCAAGTGGAAGATTGATGGCAGTGAACGACAAAATGGCGTCCTGAACAGTTGGACTGATCA

GGACAGCAAAGACAGCACCTACAGCATGAGCAGCACCCTCACGTTGACCAAGGACGAGTATGAACGACAT

AACAGCTATACCTGTGAGGCCACTCACAAGACATCAACTTCACCCATTGTCAAGAGCTTCAACAGGAATG

AGTGTTAG.
```

TOL101 has a Heavy chain encoded by the polynucleotide of SEQ ID NO:4:

```
ATGGAAAGGCACTGGATCTTTCTACTCCTGTTGTCAGTAACTGCAGGTGTCCACTCCCAGGTCCAGCTG
CAGCAGTCTGGGGCTGAACTGGCAAGACCTGGGGCCTCAGTGAAGATGTCCTGCAAGGCTTCTGGCTAC
ACCTTTACTAGCTACACGATGCACTGGGTAAAACAGAGGCCTGGACAGGGTCTGGAATGGATTGGATAC
ATTAATCCTAGCAGTGGTTATACTAATTACAATCAGAAGTTCAAGGACAAGGCCACATTGACTGCAGAC
AAATCCTCCAGCACAGCCTACATGCAACTGAGCAGCCTGACATCTGAGGACTCTGCAGTCTATTACTGT
GCAAGATGGAGGGACGCGTACTATGCTATGGACTACTGGGGTCAAGGAACCTCAGTCACCGTCTCCTCA
GAGAGTCAGTCCTTCCCAAATGTCTTCCCCCTCGTCTCCTGCGAGAGCCCCCTGTCTGATAAGAATCTG
GTGGCCATGGGCTGCCTGGCCCGGGACTTCCTGCCCAGCACCATTTCCTTCACCTGGAACTACCAGAAC
AACACTGAAGTCATCCAGGGTATCAGAACCTTCCCAACACTGAGGACAGGGGGCAAGTACCTAGCCACC
TCGCAGGTGTTGCTGTCTCCCAAGAGCATCCTTGAAGGTTCAGATGAATACCTGGTATGCAAAATCCAC
TACGGAGGCAAAAACAGAGATCTGCATGTGCCCATTCCAGCTGTCGCAGAGATGAACCCCAATGTAAAT
GTGTTCGTCCCACCACGGGATGGCTTCTCTGGCCCTGCACCACGCAAGTCTAAACTCATCTGCGAGGCC
ACGAACTTCACTCCAAAACCGATCACAGTATCCTGGCTAAAGGATGGGAAGCTCGTGGAATCTGGCTTC
ACCACAGATCCGGTGACCATCGAGAACAAAGGATCCACACCCCAAACCTACAAGGTCATAAGCACACTT
ACCATCTCTGAAATCGACTGGCTGAACCTGAATGTGTACACCTGCCGTGTGGATCACAGGGGTCTCACC
TTCTTGAAGAACGTGTCCTCCACATGTGCTGCCAGTCCCTCCACAGACATCCTAACCTTCACCATCCCC
CCCTCCTTTGCCGACATCTTCCTCAGCAAGTCCGCTAACCTGACCTGTCTGGTCTCAAACCTGGCAACC
TATGAAACCCTGAATATCTCCTGGGCTTCTCAAAGTGGTGAACCACTGGAAACCAAAATTAAAATCATG
GAAAGCCATCCCAATGGCACCTTCAGTGCTAAGGGTGTGGCTAGTGTTTGTGTGGAAGACTGGAATAAC
AGGAAGGAATTTGTGTGTACTGTGACTCACAGGGATCTGCCTTCACCACAGAAGAAATTCATCTCAAAA
CCCAATGAGGTGCACAAACATCCACCTGCTGTGTACCTGCTGCCACCAGCTCGTGAGCAACTGAACCTG
AGGGAGTCAGCCACAGTCACCTGCCTGGTGAAGGGCTTCTCTCCTGCAGACATCAGTGTGCAGTGGCTT
CAGAGAGGGCAACTCTTGCCCCAAGAGAAGTATGTGACCAGTGCCCCGATGCCAGAGCCTGGGGCCCCA
GGCTTCTACTTTACCCACAGCATCCTGACTGTGACAGAGGAGGAATGGAACTCCGGAGAGACCTATACC
TGTGTTGTAGGCCACGAGGCCCTGCCACACCTGGTGACCGAGAGGACCGTGGACAAGTCCACTGGTAAA
CCCACACTGTACAATGTCTCCCTGATCATGTCTGACACAGGCGGCACCTGCTATTGA.
```

TOL101 has a J chain encoded by the polynucleotide sequence of SEQ ID NO: 5:

```
ATGAAGACCCACCTGCTTCTCTGGGGAGTCCTGGCCATTTTTGTTAAGGCTGTCCTTGTAACAGGTGACG
ACGAAGCGACCATTCTTGCTGACAACAAATGCATGTGTACCCGAGTTACCTCTAGGATCATCCCTTCCAC
CGAGGATCCTAATGAGGACATTGTGGAGAGAAATATCCGAATTGTTGTCCCTTTGAACAACAGGGAGAAT
ATCTCTGATCCCACCTCCCCACTGAGAAGGAACTTTGTATACCATTTGTCAGACGTCTGTAAGAAATGCG
ATCCTGTGGAAGTGGAGCTGGAAGATCAGGTTGTTACTGCCACCCAGAGCAACATCTGCAATGAAGACGA
TGGTGTTCCTGAGACCTGCTACATGTATGACAGAAACAAGTGCTATACCACTATGGTCCCACTTAGGTAT
CATGGTGAGACCAAAATGGTGCAAGCAGCCTTGACCCCCGATTCTTGCTACCCTGACTAG.
```

The amino acid sequence of the TOL101 Light chain is according to SEQ ID NO: 6:

MDFQVQIFSFLLISASVIISRGQIVLTQSPAIMSASPGEKVTMTCSASSSVSYMHWYQQRSGTSPKRWIYDTS

KLASGVPAREFSGSGSGTSYSLTISSMEAEDAATYYCQQWSSNPFTFGSGTKLEIKRADAAPTVSIFPPSSEQL

TSGGASVVCFLNNFYPKDINVKWKIDGSERQNGVLNSWTDQDSKDSTYSMSSTLTLTKDEYERHNSYTCE

ATHKTSTSPIVKSFNRNEC

The amino acid sequence of the TOL101 Heavy chain is according to SEQ ID NO: 7:

MERHWIFLLLLSVTAGVHSQVQLQQSGAELARPGASVKMSCKASGYTFTSYTMHWVKQRPGQGLEWIGY

INPSSGYTNYNQKFKDKATLTADKSSSTAYMQLSSLTSEDSAVYYCARWRDAYYAMDYWGQGTSVTVSS

ESQSFPNVFPLVSCESPLSDKNLVAMGCLARDFLPSTISFTWNYQNNTEVIQGIRTFPTLRTGGKYLATSQVL

LSPKSILEGSDEYLVCKIHYGGKNRDLHVPIPAVAEMNPNVNVFVPPRDGFSGPAPRKSKLICEATNFTPKPI

TVSWLKDGKLVESGFTTDPVTIENKGSTPQTYKVISTLTISEIDWLNLNVYTCRVDHRGLTFLKNVSSTCAA

SPSTDILTFTIPPSFADIFLSKSANLTCLVSNLATYETLNISWASQSGEPLETKIKIMESHPNGTFSAKGVASVC

VEDWNNRKEFVCTVTHRDLPSPQKKFISKPNEVHKHPPAVYLLPPAREQLNLRESATVTCLVKGFSPADISV

QWLQRGQLLPQEKYVTSAPMPEPGFYFTHSILTVTEEEWNSGETYTCVVGHEALPHLVTERTVDKSTG

KPTLYNVSLIMSDTGGTCY

The amino acid sequence of the TOL101 J chain is according to SEQ ID NO: 8:

MKTHLLLWGVLAIFVKAVLVTGDDEATILADNKCMCTRVTSRIIPSTEDPNEDIVERNIRIVVPLNNRENISD

PTSPLRRNFVYHLSDVCKKCDPVEVELEDQVVTATQSNICNEDDGVPETCYMYDRNKCYTTMVPLRYHGE

TKMVQAALTPDSCYPD

As used herein a "αβ TCR" can include a heterodimer of a mammalian α-subunit and a mammalian β-subunit of a mammalian TCR. In some embodiments, the mammalian α-subunit can comprise the amino acid sequence of a human α-subunit, for example, an amino acid sequence of SEQ ID NO:1:

MAKTTQPNSMESNEEEPVHLPCNHSTISGTDYIHWYRQLPSQGPEYVIHGLTSNVNNRMASLAIAEDRKSSTLILHRATL

RDAAVYYCILPLAGGTSYGKLTFGQGTILTVHPNIQNPDPAVYQLRDSKSSDKSVCLFTDFDSQTNVSQSKDSDVYITDK

TVLDMRSMDFKSNSAVAWSNKSDFACANAFNNSIIPEDMITSPESS.

In some embodiments, the mammalian β-subunit can comprise the amino acid sequence of a human β-subunit, for example, an amino acid sequence of SEQ ID NO:2:

MAGSHMGVSQSPRYKVAKRGQDVALRCDPISGHVSLFWYQQALGQGPEFLTYFQNEAQLDKSGLPSDRFFAERPEGSV

STLKIQRTQQEDSAVYLCASSLGQAYEQYFGPGTRLTVTEDLKNVFPPEVAVFEPSEAEISHTQKATLVCLATGFYPDHV

ELSWWVNGKEVHSGVSTDPQPLKEQPALNDSRYCLSSRLRVSATFWQNPRNHFRCQVQFYGLSENDEWTQDRAKPVT

QIVSAEAWGRADCTSGD DDDK.

In some embodiments, an illustrative human αβ TCR can be a heterodimer comprising the subunits αβ of SEQ ID NOs: 1 & 2. In some embodiments, a human αβ TCR or fragment thereof comprises at least a portion of SEQ ID NOs: 1 & 2. In some embodiments, the human αβ TCR can include a portion or fragment that includes at least a portion of SEQ ID NO: 1 or 2.

As used herein, the terms "complementarity determining region" and "CDR" refer to the regions that are primarily responsible for antigen-binding. There are three CDRs in a light chain variable region (CDRL1, CDRL2, and CDRL3), and three CDRs in a heavy chain variable region (CDRH1, CDRH2, and CDRH3). The residues that make up these six CDRs have been characterized by Kabat and Chothia as follows: residues 24-34 (CDRL1), 50-56 (CDRL2) and 89-97 (CDRL3) in the light chain variable region and 31-35

(CDRH1), 50-65 (CDRH2) and 95-102 (CDRH3) in the heavy chain variable region; Kabat et al., (1991) Sequences of Proteins of Immunological Interest, 5th Ed, Public Health Service, National Institutes of Health, Bethesda, Md., herein incorporated by reference; and residues 26-32 (CDRL1), 50-52 (CDRL2) and 91-96 (CDRL3) in the light chain variable region and 26-32 (CDRH1), 53-55 (CDRH2) and 96-101 (CDRH3) in the heavy chain variable region; Chothia and Lesk (1987) J. Mol. Biol. 196: 901-917, herein incorporated by reference. In certain embodiments, the terms "complementarity determining region" and "CDR" as used herein, include the residues that encompass both the Kabat and Chothia definitions (i.e., residues 24-34 (CDRL1), 50-56 (CDRL2), and 89-97 (CDRL3) in the light chain variable region; and 26-35 (CDRH1), 50-65 (CDRH2), and 95-102 (CDRH3)). Also, unless specified, as used herein, the numbering of CDR residues is according to Kabat. In certain embodiments, the present invention provides humanized antibodies composed of the six CDRs from TOL101, within a human framework (e.g., the deposited hybridomas are sequenced and humanized antibodies are assembled recombinantly according to techniques known in the art).

As used herein, the term "framework" refers to the residues of the variable region other than the CDR residues as defined herein. There are four separate framework sub-regions that make up the framework: FR1, FR2, FR3, and FR4. In order to indicate if the framework sub-region is in the tight or heavy chain variable region, an "L" "H" may be added to the sub-region abbreviation (e.g., "FRL1" indicates framework sub-region 1 of the light chain variable region). Unless specified, the numbering of framework residues is according to Kabat. It is noted that, in certain embodiments, the anti-αβ TCR antibodies or fragments thereof may have less than a complete framework (e.g., they may have a portion of a framework that only contains one or more of the four sub-regions).

As used herein, the term "fully human framework" means a framework with an amino acid sequence found naturally in humans. Examples of fully human frameworks, include, but are not limited to, KOL, NEWM, REI, EU, TUR, TEI, LAY and POM (See, e.g., Kabat et al., (1991) Sequences of Proteins of Immunological Interest, US Department of Health and Human Services, NIH, USA; and Wu et al., (1970) J. Exp. Med. 132, 211-250, both of which are herein incorporated by reference), in certain embodiments, the humanized antibodies of the present invention have fully human frameworks, or frameworks with one or more amino acids changed to accommodate the murine CDRs of TOL101.

As used herein, "Humanized" antibodies refer to a chimeric molecule, generally prepared using recombinant techniques, having an antigen binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the complementarity determining regions (CDRs) grafted onto appropriate framework regions in the variable domains. Antigen binding sites may be wild type or modified by one or more amino acid substitutions. This generally eliminates the constant region as an immunogen in human individuals, but the possibility of an immune response to the foreign variable region generally remains. Another approach focuses not only on providing human-derived constant regions, but modifying the variable regions as well so as to reshape them as closely as possible to human form. It is known that the variable regions of both heavy and light chains contain three complementarily-determining regions (CDRs) which vary in response to the antigens in question and determine binding capability, flanked by four framework regions (FRs) which are relatively conserved in a given species and which putatively provide a scaffolding for the CDRs. When nonhuman antibodies are prepared with respect to a particular antigen, the variable regions can be "reshaped" or "humanized" by grafting CDRs derived from nonhuman antibody on the FRs present in the human antibody to be modified. Application of this approach to various antibodies has been reported by Sato, K., et al., (1993) Cancer Res 53:851-856. Riechmann, L., et al., (1988) Nature 332:323-327; Verhoeyen, M., et al., (1988) Science 239:1534-1536; Kettleborough, C. A., et al., (1991) Protein Engineering 4:773-3783; Maeda, H., et al., (1991) Human Antibodies Hybridoma 2:124-134; Gorman, S. D., et al., (1991) Proc Natl Acad Sci USA 88:4181-4185; Tempest, P. R., et al., (1991) Bio/Technology 9:266-271; Co, M. S. et al., (1991) Proc Natl Acad Sci USA 88:2869-2873; Carter, P., et al., (1992) Proc Natl Acad Sci USA 89:4285-4289; and Co, M. S. et al., (1992) J Immunol 148:1149-1154, all of which are herein incorporated by reference. In some embodiments, humanized antibodies preserve all CDR sequences (for example, a humanized mouse antibody which contains all six CDRs from the deposited TOL101 antibody). In other embodiments, humanized antibodies have one or more CDRs (one, two, three, four, five, six) which are altered with respect to the original antibody (e.g. original TOL101 antibody), which are also termed one or more CDRs "derived from" one or more CDRs from the original antibody.

As used herein, the terms "subject" and "patient" refer to any animal, such as a mammal. The term "mammal" as used herein refers to any mammal classified as a mammal, including humans, non-human primates, apes, pigs, caws, goats, sheep, horses, dogs, cats and those mammals employed in scientific research commonly known in the art, for example, mice, rats, hamsters, rabbits, guinea-pigs, and ferrets. In a preferred embodiment of the invention, the mammal is a human.

As used herein, the term "purified" or "to purify" refers to the removal of contaminants from a sample. For example, αβ TCR specific antibodies may be purified by removal of contaminating non-immunoglobulin proteins; they are also purified by the removal of immunoglobulins that do not bind to the same antigen. The removal of non-immunoglobulin proteins and/or the removal of immunoglobulins that do not bind the particular antigen results in an increase in the percentage of antigen specific immunoglobulins in the sample. In another example, recombinant antigen-specific polypeptides are expressed in bacterial, eukaryotic or mammalian host cells and the polypeptides are purified by the removal of host cell proteins; the percentage of recombinant antigen-specific polypeptides is thereby increased in the sample.

As used herein, the term "Fc region" refers to a C-terminal region of an immunoglobulin heavy chain. The "Fc region" may be a native sequence Fc region or a variant Fc region (e.g., with increased or decreased effector functions).

As used herein, an Fc region may possess "effector functions" that are responsible for activating or diminishing a biological activity (e.g., in a subject). Examples of effector functions include, but are not limited to: C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions may require the Fc region to be combined with a binding domain (e.g., an antibody variable domain) and can be assessed using various assays (e.g. Fc binding assays, ADCC assays, CDC assays, etc.).

As used herein, an "isolated" antibody or antibody fragment is one that has been identified and separated and/or recovered from a component of its natural environment. Contaminant components of its natural environment are materials that would interfere with diagnostic or therapeutic uses for the antibody or fragment thereof, and may include enzymes, hormones, and other proteinaceous or non-proteinaceous solutes. In certain embodiments, the isolated antibody is purified (1) to greater than 95% by weight of polypeptides as determined by the Lowry method, and preferably, more than 99% by weight, (2) to a degree sufficient to obtain at least 15 residues of N-terminal or internal amino acid sequence by use of a spinning cup sequenator, or (3) to homogeneity by SDS-page under reducing or non-reducing conditions using Coomassie blue, or silver stain. An isolated antibody includes the antibody in situ within recombinant cells since at least one component of the polypeptide's natural environment will not be present. Ordinarily, however, an isolated antibody will be prepared by a least one purification step.

As used herein, the term "treatment" refers to both therapeutic treatment and prophylactic or preventative measures. Those in need of treatment include those already with the disorder as well as those in which the disorder is to be prevented.

The phrase "under conditions such that the symptoms are reduced" refers to any degree of qualitative or quantitative reduction in detectable symptoms of any disease treatable by all TCR antibodies, including but not limited to, a detectable impact on the rate of recovery from disease (e.g., rate of weight gain), or the reduction of at least one of the symptoms normally associated with the particular disease (e.g., symptoms of graft rejection). In certain embodiments, the all TCR antibodies of the present invention are administered to a subject under conditions such that symptoms of graft rejection or GVHD are reduced (e.g., as compared to not treating with the TCR antibodies).

The headings (such as "Background" and "Summary") and sub-headings used herein are intended only for general organization of topics within the present technology, and are not intended to limit the disclosure of the present technology or any aspect thereof. In particular, subject matter disclosed in the "Background" may include novel technology and may not constitute a recitation of prior art. Subject matter disclosed in the "Summary" exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The citation of references herein does not constitute an admission that those references are prior art or have any relevance to the patentability of the technology disclosed herein. Any discussion of the content of references cited in the present disclosure is intended merely to provide a general summary of assertions made by the authors of the references, and does not constitute an admission as to the accuracy of the content of such references. All references cited in the "Description" section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing or having, is used herein to describe and claim the invention, the present technology, or embodiments thereof, may alternatively be described using more limiting terms such as "consisting of" or "consisting essentially of" the recited ingredients.

Unless otherwise defined, all technical and scientific terms used herein have the same meaning as commonly understood by one of ordinary skill in the art to which this present technology belongs. Although methods and materials similar or equivalent to those described herein can be used in the practice or testing of the present technology, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

Isolated Antibodies and Antibody Fragments Directed to αβ TCR

The term "antibody" is used in the broadest sense and specifically covers single anti-all TCR antibodies (including agonist, antagonist, and neutralizing or blocking antibodies) and anti-all TCR antibody compositions with polyepitopic specificity. "Antibody" as used herein includes intact immunoglobulin or antibody molecules, polyclonal antibodies, multispecific antibodies (i.e., bispecific antibodies formed from at least two intact antibodies) and immunoglobulin fragments (such as say, Fab, F(ab')$_2$, or Fv), so long as they exhibit any of the desired agonistic or antagonistic or functional or clinical properties described herein.

Antibodies axe typically proteins or polypeptides which exhibit binding specificity to a specific antigen. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains [Chothia et al., J. Mol. Biol., 186:651-663 (1985); Novotny and Haber, Proc. Natl. Acad. Sci. USA, 82:4592-4596 (1985)]. The light chains of antibodies from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes.

There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called alpha, delta, epsilon, gamma, and mu, respectively.

"Antibody fragments" comprise a portion of an intact antibody, generally the antigen binding or variable region of the intact antibody. Examples of antibody fragments include Fab, Fab', F(ab')$_2$, and F V fragments, diabodies, and multispecific antibodies formed from antibody fragments.

The term "variable" is used herein to describe certain portions of the variable domains which differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies [see Kabat, E. A, et al., Sequences of Proteins of Immunological interest, National Institutes of Health, Bethesda, Md. (1987)]. The constant domains are not involved directly in binding an antibody to an antigen, but exhibit various effector functions, such as participation of the antibody in antibody-dependent cellular toxicity.

The term "monoclonal antibody" as used herein refers to an antibody obtained from a population of substantially homogeneous antibodies, the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include chimeric, hybrid and recombinant antibodies produced by splicing a variable (including hypervariable) domain of an anti-αβ TCR antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity or properties. See, e.g. U.S. Pat. No. 4,816,567 and Mage et al., in Monoclonal Antibody Production Techniques and Applications, pp. 79-97 (Marcel Dekker, Inc.: New York, 1987).

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein. Nature, 256:495 (1975), or may be made by recombinant DNA methods such as described in U.S. Pat. No. 4,816,567. The "monoclonal antibodies" may also be isolated from phage libraries generated using the techniques described in McCafferty et al., Nature, 348:552-554 (1990), for example.

"Humanized" forms of non-human (e.g. murine) antibodies are specific chimeric immunoglobulins, immunoglobulin chains, or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance, in general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (e), typically that of a human immunoglobulin.

A "human antibody" is one which possesses an amino acid sequence which corresponds to that of an antibody produced by a human and/or has been made using any of the techniques for making human antibodies known in the art or as disclosed herein. This definition of a human antibody includes antibodies comprising at least one human heavy chain polypeptide or at least one human light chain polypeptide, for example an antibody comprising murine light chain and human heavy chain polypeptides. Human antibodies can be produced using various techniques known in the art. In one embodiment, the human antibody is selected from a phage library, where that phage library expresses human antibodies (Vaughan et al. Nature Biotechnology, 14:309-314 (1996): Sheets et al. PNAS, (USA) 95:6157-6162 (1998)); Hoogenboom and Winter, J. Mol. Biol., 227:381 (1991); Marks et al., J. Mol. Biol., 222:581 (1991)). Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos.

5,545,807; 5,545,806; 5,569,825; 5,625,126; 5,633,425; 5,661,016, and in the following scientific publications: Marks et al., Bio/Technology, 10: 779-783 (1992); Lonberg et al., Nature, 368: 856-859 (1994); Morrison, Nature, 368:812-13 (1994); Fishwild et al., Nature Biotechnology, 14: 845-51 (1996); Neuberger, Nature Biotechnology, 14: 826 (1996); Lonberg and Huszar, Intern. Rev. Immunol., 13:65-93 (1995). Alternatively, the human antibody may be prepared via immortalization of human B lymphocytes producing an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner et al., J. Immunol., 147 (1):86-95 (1991); and U.S. Pat. No. 5,750,373.

The anti-αβ TCR antibody or antibody fragment variable regions and/or CDRs of the present invention, and variants thereof, may be employed with any type of suitable human constant regions (e.g., for chimeric antibodies) or human framework (e.g., for humanized antibodies). In certain embodiments, the constant regions are of the IgM class. Preferably, the CDRs are used with fully human frameworks or framework sub-regions. For example, the NCBI web site contains the sequences for certain human framework regions. Examples of human VH sequences include, but are not limited to, VH1-18, VH1-2, VH1-24, VH1-3, VH1-45, VH1-46, VH1-58, VH1-69, VH1-8, VH2-26, VH2-5, VH2-70, VH3-11, VH3-13, VH3-15, VH3-16, VH3-20, VH3-21, VH13-23, VH3-30, VH3-33, VH3-35, VH3-38, VH3-43, VH3-48, VH3-49, VH3-53, VH3-64, VH3-66, VH3-7, VH3-72, VH3-73, VH3-74, VH3-9, VH4-28, VH4-31, VH4-34, VH4-39, VH4-4, VH4-59, VH4-61, VH5-51, VH6-1, and VH7-81, which are provided in Matsuda et al., J Exp. Med. 1998 Dec. 7; 188(11):2151-62, that includes the complete nucleotide sequence of the human immunoglobulin chain variable region locus, herein incorporated by reference. Examples of human VK sequences include, but are not limited to, A1, A10, A11, A14, A17, A18, A19, A2, A20, A23, A26, A27, A3, A30, A5, A7, B2, B3, L1, L10, L11, L12, L14, L15, L16, L18, L19, L2, L20, L22, L23, L24, L25, L4/18a, L5, L6, L8, L9, O1, O11, O12, O14, O18, O2, O4, and O08, which are provided in Kawasaki et al., Eur J Immunol April; 31(4):1017-28; Sellable and Zachau, Biol Chem Hoppe Seyler 1993 November; 374(11):1001-22; and Brensing-Kuppers et Gene 1997 Jun. 3; 191(2):173-81, all of which are herein incorporated by reference. Examples of human VL sequences include, but are not limited to, V1-11, V1-13, V1-16, V1-17, V1-18, V1-19, V1-2, V1-20, V1-22, V1-3, V1-4, V1-5, V1-7, V1-9, V2-1, V2-11, V2-13, V2-14, V2-15, V2-17, V2-19, V2-6, V2-7, V2-8, V3-2, V3-3, V3-4, V4-1, V4-2, V4-3, V4-4, V4-6, V5-1, V5-2, V5-4, and V5-6, which are provided in Kawasaki et al., Genome Res 1997 March; 7(3):250-61, herein incorporated by reference, Fully human frameworks can be selected from any of these functional germline genes. Generally, these frameworks differ from each other by a limited number of amino acid changes. These frameworks may be used with the CDRs from TOL101 or variants thereof. Additional examples of human frameworks which may be used with the CDRs of the present invention include, but are not limited to, KOL, NEWM, REI, EU, TUR, TEI, LAY and POM (See, e.g., Kabat et al., 1987 Sequences of Proteins of Immunological Interest, US Department of Health and Human Services, NIH, USA; and Wu et al., 1970, J. Exp. Med. 132, 211-250, both of which are herein incorporated by reference).

The term "Fc region" is used to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region (using herein the numbering system according to Kabat et al., supra). The Fc region of an immunoglobulin generally comprises two constant domains, a $CH_2$ domain and a $CH_3$ domain, and optionally comprises a $CH_4$ domain.

By "Fc region chain" herein is meant one of the two polypeptide chains of an Fc region. The "$CH_2$ domain" of a human IgG Fc region (also referred to as "Cγ2" domain) usually extends from an amino acid residue at about position 231 to an amino acid residue at about position 340. The $CH_2$ domain is unique in that it is not closely paired with another domain. Rather, two N-linked branched carbohydrate chains are interposed between the two $CH_2$ domains of an intact native IgG molecule. It has been speculated that the carbohydrate may provide a substitute for the domain-domain pairing and help stabilize the $CH_2$ domain. Burton, Molec. Immunol. 22:161-206 (1985). The $CH_2$ domain herein may be a native sequence $CH_2$ domain or variant $CH_2$ domain.

The "$CH_3$ domain" comprises the stretch of residues C-terminal to a $CH_2$ domain in an Fc region (i.e. from an amino acid residue at about position 341 to an amino acid residue at about position 447 of an IgG). The $CH_3$ region herein may be a native sequence $CH_3$ domain or a variant $CH_3$ domain (e.g. a $CH_3$ domain with an introduced "protroberance" in one chain thereof and a corresponding introduced "cavity" in the other chain thereof; see U.S. Pat. No. 5,821,333). Such variant $CH_3$ domains may be used to make multispecific (e.g. bispecific) antibodies as herein described.

"Hinge region" is generally defined as stretching from about Glu216, or about Cys226, to about Pro230 of human $IgG_1$ (Burton, Molec. Immunol, 22:161-206 (1985)). Hinge regions of other IgG isotypes may be aligned with the IgG1 sequence by placing the first and last cysteine residues forming inter-heavy chain S—S bonds in the same positions. The hinge region herein may be a native sequence hinge region or a variant hinge region. The two polypeptide chains of a variant hinge region generally retain at least one cysteine residue per polypeptide chain, so that the two polypeptide chains of the variant hinge region can form a disulfide bond between the two chains. The preferred hinge region herein is a native sequence human hinge region, e.g. a native sequence human IgG1 hinge region.

A "functional Fc region" possesses at least one "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays known in the an for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95% sequence identity therewith.

"Antibody-dependent T-cell-mediated cytotoxicity" and "ADCC" refer to a cell-mediated reaction in which nonspecific cytotoxic cells that express Fc receptors (FcRs) (e.g. Natural Killer (NK) neutrophils, and macrophages) recognize bound antibody on a target T-cell and subsequently cause lysis of the target T-cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol., 9:457-92 (1991). To assess ADCC activity of a molecule of interest, an in vitro ADCC assay, such as that described in U.S. Pat. No. 5,500,362 or U.S. Pat. No. 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. PNAS (USA), 95:652-656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T-cells and neutrophils; with PBMCs and NK cells being preferred. The effector cells may be isolated from a native source thereof, e.g. from blood or PBMCs as described herein.

The terms "Fc receptor" and "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRO, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof, Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (reviewed in Dacron, Annu. Rev. Immunol., 15:203-234 (1997)). Felts are reviewed in Ravetch and Kinet, Annu. Rev. Immunol., 9:457-92 (1991); Capel et al., Immunomethods, 4:25-34 (1994); and de Haas et al., J. Lab. Clin. Med., 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol., 117:587 (1976); and Kim et al., J. Immunol., 24:249 (1994)).

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., J. Immunol. Methods, 202:163 (1996), may be performed.

An "affinity matured" antibody is one with one or more alterations in one or more CDRs thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. Bio/Technology, 10:779-783 (1992) describes affinity maturation by and VL domain shuffling, Random mutagenesis of CDR and/or framework residues is described by: Barbas et al. Proc Nat. Acad. Sci, USA 91:3809-3813 (1994); Schier et al. Gene, 169:147-155 (1995); Yelton et al. J. Immunol., 155:1994-2004 (1995); Jackson et al., J. Immunol., 154(7):3310-9 (1995); and Hawkins et al., J. Mol. Biol., 226:889-896 (1992).

The term "immunospecific" as used in "immunospecific binding of antibodies" for example, refers to the antigen specific binding interaction that occurs between the antigen-combining site of an antibody and the specific antigen recognized by that antibody.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha and TOE-beta; insulin-like growth factor-I and -II; erythropoietin (EPO); osteo inductive factors; interferons such as interferon-alpha, -beta and -gamma colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; a tumor necrosis factor such as TNF-alpha or TNF-beta; and other polypeptide factors including LIF and kit ligand (KL). As used herein, the term cytokine includes proteins from natural sources or from recombinant T-cell culture and biologically active equivalents of the native sequence cytokines.

The terms "treating," "treatment," and "therapy" as used herein refer to curative therapy; therapy that reduces or ameliorates symptoms of a disease or condition; prophylactic therapy; and preventative therapy.

The term "therapeutically effective amount" refers to an amount of an active agent (e.g. an antibody or antibody fragment) or drug effective to treat a disease or disorder in a mammal. In the case of an autoimmune disease of an inflammatory disease, the therapeutically effective amount of the active agent or drug may reduce the number of activated immune cells, (for example αβ TCR+ T-cells); increase the number and/or activity of $T_{reg}$-cells, reduce the production of inflammatory cytokines, or pro-immune cytokines, such as IL-2, interferon-γ, or TNF-α from activated T-cells; inhibit (i.e., slow to some extent and preferably stop) proliferation of activated T-cells; reduce the expression of CD3 on the surface of (113 TCR+ T-cells to below 50/mm$^3$, preferably below 25/mm$^3$; and/or relieve to some extent, one or more of the symptoms associated with the autoimmune and/or inflammatory disorder. To the extent the antibody or antibody active agent or drug may prevent activation and expansion of αβ TCR+ T-cells, it may be anti-inflammatory and/or autoantigen tolerance inducing. For autoimmune or inflammation therapy, efficacy in vivo can, for example, be measured by assessing the amount of inflammatory cytokines, or pro-immune cytokines, such as interferon-γ, or TNF-α from activated T-cells and the depletion of functional CD3 molecules on the surface of αβ TCR+ T-cells. For treatment of transplant tissue rejection, a "therapeutically effective amount" refers to an amount of an active agent (e.g. an anti αβ TCR antibody or antibody fragment) e.g. TOL101, or a secondary adjunct drug effective to abrogate, reduce, cease or prevent the rejection of a transplanted tissue as measured by abrogation, reduction, cessation or prevention of cellular necrosis of transplanted tissue, production of alloreactive antibodies, or production alloreactive T-cells reactive against the transplanted tissue in vivo or in vitro.

The term "Human-anti-mouse antibody response" Of "HAMA" refers to an immunologic response against a murine antibody following administration of a murine antibody to a human subject. Typically, mouse antibodies are recognized as foreign by the human immune system and thus they provoke the Human Anti-Mouse Antibody or HAMA response. The HAMA response interferes with the efficacy of the mouse antibody and can cause severe adverse symptoms in the recipient. The HAMA response may also interfere with the use of other murine-based therapeutics or diagnostics that may subsequently be administered to the patient. Methods for measuring HAMA and/or diagnosing HAMA in patients are well known in the art. See, e.g., ImmuSTRIP® HAMA IgG ELISA Test System (Catalog Number 10016; IMMUNOMEDICS®, INC. 300 American Road, Morris Plains, N.J. 07950) or HAMA (human anti-mouse antibodies) ELISA (IgG and IgM HAMA, Catalog Number 43-HAMHU-E01; ALPCO DIAGNOSTICS, 26-G Keewaydin Drive, Salem, N.H. 03079) or Gruber et. al, Cancer Res., 60: 1921-1926 (2000).

Polyclonal Antibodies

Polyclonal antibodies are preferably raised in animals by multiple subcutaneous (sc) or intraperitoneal (ip) injections of the relevant antigen and an adjuvant. Alternatively, antigen may be injected directly into the animal's lymph node (see Kilpatrick et al., Hybridoma, 16:381-389, 1997). An improved antibody response may be obtained by conjugating the relevant antigen to a protein that is immunogenic in the species to be immunized, e.g., keyhole limpet hemocyanin, serum albumin, bovine thymoglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride or other agents known in the art.

Animals are immunized against the αβ TCR protein, fragments thereof, immunogenic conjugates or derivatives thereof by combining, e.g., 100 μg of the protein or conjugate (for mice) with 3 volumes of Freund's complete adjuvant and injecting the solution intradermally at multiple sites. One month later, the animals are boosted with ⅕ to ¹⁄₁₀ the original amount of peptide or conjugate in Freund's complete adjuvant by subcutaneous injection at multiple sites. At 7-14 days post-booster injection, the animals are bled and the serum is assayed for antibody titer. Animals are boosted until the titer plateaus. Preferably, the animal is boosted with the conjugate of the same antigen, but conjugated through a different cross-linking reagent. Conjugates also can be made in recombinant cell culture as protein fusions. Also, aggregating agents such as alum are suitably used to enhance the immune response.

Monoclonal Antibodies

The antibodies of the invention maybe monoclonal antibodies, Monoclonal antibodies may be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the αβ TCR or subunit thereof. In non-limiting examples, the αβ TCR subunit can include an alpha chain, a beta chain or a linked alpha-beta chain. In some embodiments, the TCR can be a mammalian β TCR. In some embodiments, the αβ TCR used for immunizing an animal includes a human αβ TCR comprising an amino acid sequence of SEQ ID NO: 1. or a fragment thereof. The immunizing agent may alternatively comprise a fragment or portion of SEQ ID NO: 1, in one embodiment, the immunizing agent comprises a protein comprising the amino acid sequence of SEQ ID NO:1. In one embodiment, the immunizing agent comprises a protein comprising the amino acid sequence of SEQ ID NO:2 or a fragment of portion of SEQ ID NO:2. In one embodiment, the immunizing agent comprises a protein of two subunits as provided by the amino acid sequences of SEQ ID NO:1 and 2. Alternatively, the immunogen can comprise an αβ TCR heterodimer, from a desired species, for example a human αβ TCR heterodimer. In one embodiment, the immunizing agent comprises a population of human buffy coat cells containing peripheral blood mononuclear cells.

Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (see illustrative methods for making monoclonal antibodies disclosed in: Goding, Monoclonal Antibodies: Principles and Practice, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient T-cells. In some embodiments, preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. An example of such a murine myeloma cell line is P3X63Ag8U.1, (ATCC CRL 1580). Human myeloma and mouse-human heteromyeloma cell lines also have been described for the production of human monoclonal antibodies (see for example, Kozbor, J. Immunol., 133:3001 (1984);

Brodeur et al., Monoclonal Antibody Production Techniques and Applications, Marcel Dekker, Inc., New York, (1987) pp. 51-63].

The culture medium in which the hybridoma cells are cultured can then be assayed for the presence of monoclonal antibodies directed against a αβ TCR. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA), alternatively, the binding specificity of the monoclonal antibodies produced by the hybridoma cells can be determined by incubating a population of T-cells with the monoclonal antibodies and co-staining using an anti-CD3 antibody. Such techniques and assays are known in the art. The binding affinity of the monoclonal antibody can, for example, be determined by the Scatchard analysis of Munson and Pollard, Anal. Biochem. 107:220 (1980).

After the desired hybridoma cells are identified, the clones may be subcloned by limiting dilution procedures and grown by standard methods (see for example, Goding, supra). Suitable culture media for this purpose include, for example, Dulbecco's Modified Eagle's Medium or RPM-1640 medium. Alternatively, the hybridoma cells may be grown in vivo as ascites in a mammal commonly used and routinely produced in the art.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Recombinant Production of Antibodies

The amino acid sequence of n immunoglobulin of interest can generally be determined by direct protein sequencing, and suitable encoding nucleotide sequences can be designed according to a universal codon table. However, in the case of IgM antibodies, direct protein sequencing from the antibody protein is very difficult. The amino acid sequence of TOL101, an IgM antibody, is particularly intractable to standard protein sequencing protocols. Alternatively, DNA encoding the monoclonal antibodies, including TOL101, can be isolated and sequenced from the hybridoma cells, including the hybridoma TOL101 MCB, to ascertain the amino acid sequence of the antibody using conventional procedures (e.g., by using oligonucleotide probes that are capable of binding specifically to genes encoding the heavy and light chains of the monoclonal antibodies), Sequence determination will generally require isolation of at least a portion of the gene or cDNA of interest. Usually this requires cloning the DNA or mRNA encoding the monoclonal antibodies. Cloning is carried out using standard techniques (see, e.g., Sambrook et al. (1989) Molecular Cloning: A Laboratory Guide, Vols 1-3, Cold Spring Harbor Press, which is incorporated herein by reference). For example, a cDNA library can be constructed by reverse transcription of polyA+ mRNA, preferably membrane-associated mRNA, and the library screened using probes specific for human immunoglobulin polypeptide gene sequences. In a preferred embodiment, the polymerase chain reaction (PCR) is used to amplify cDNAs (or portions of full-length cDNAs) encoding an immunoglobulin gene segment of interest (e.g., a light chain variable segment). The amplified sequences can be cloned readily into any suitable vector, e.g., expression vectors, minigene vectors, or phage display vectors. It will be appreciated that the particular method of cloning used is not critical, so long as it is possible to determine the sequence of some portion of the immunoglobulin polypeptide of interest.

One source for RNA used for cloning and sequencing is a hybridoma produced by obtaining a B cell from the transgenic mouse and fusing the B cell to an immortal cell. An advantage of using hybridomas is that they can be easily screened, and a hybridoma that produces a human monoclonal antibody of interest selected. Alternatively, RNA can be isolated from B cells (or whole spleen) of the immunized animal. When sources other than hybridomas are used, it may be desirable to screen for sequences encoding immunoglobulins immunoglobulin polypeptides with specific binding characteristics. One method for such screening is the use of phage display technology. Phage display is described in e.g., Dower et al., WO 91/17271, McCafferty et al., WO 92/01047, and Caton and Koprowski, Proc. Natl. Acad. Sci. USA, 87:6450-6454 (1990), each of which is incorporated herein by reference. In one embodiment using phage display technology, cDNA from an immunized transgenic mouse (e.g., total spleen cDNA) is isolated, PCR is used to amplify cDNA sequences that encode a portion of an immunoglobulin polypeptide, e.g., CDR regions, and the amplified sequences are inserted into a phage vector. cDNAs encoding peptides of interest, e.g., variable region peptides with desired binding characteristics, are identified by standard techniques such as panning. The sequence of the amplified or cloned nucleic acid is then determined. Typically the sequence encoding an entire variable region of the immunoglobulin polypeptide is determined, however, sometimes only a portion of a variable region need be sequenced, for example, the CDR-encoding portion. Typically the sequenced portion will be at least 30 bases in length, and more often bases coding for at least about one-third or at least about one-half of the length of the variable region will be sequenced. Sequencing can be carried out on clones isolated from a cDNA library or, when PCR is used, after subcloning the amplified sequence or by direct PCR sequencing of the amplified segment. Sequencing is carried out using standard techniques (see, e.g., Sambrook et al. (1989) Molecular Cloning: A Laboratory Guide, Vols 1-3, Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of human immunoglobulin genes and cDNAs, an artisan can determine readily, depending on the region sequenced, (i) the germline segment usage of the hybridoma immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

Once isolated, the DNA may be operably linked to expression control sequences or placed into expression vectors, which are then transfected into bacterial, eukaryotic and/or mammalian host cells such as E. coli cells, simian COS cells, Chinese hamster ovary (CHO) cells, or myeloma cells that do not otherwise produce immunoglobulin protein, to direct the synthesis of monoclonal antibodies in the recombinant host cells.

Expression control sequences denote DNA sequences necessary for the expression of an operably linked coding sequence in a particular host organism. The control sequences that are suitable for prokaryotes, for example, include a promoter, optionally an operator sequence, and a ribosome-binding site. Eukaryotic cells are known to utilize promoters, polyadenylation signals, and enhancers. Suitable expression control sequences for expression of antibodies in prokaryotic, eukaryotic and/or mammalian host cells are well known in the art.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome-binding site is operably linked to a coding sequence if it is positioned so as to facilitate translation. Generally, operably linked means that the DNA sequences being linked are contiguous, and, in the case of a secretory leader, contiguous and in reading phase. However, enhancers do not have to be contiguous. Linking can be accomplished by ligation at convenient restriction sites. If such sites do not exist, synthetic oligonucleotide adaptors or linkers can be used in accordance with conventional practice.

"Cell line" and "cell culture" are often used interchangeably and all such designations include progeny. Transformants and transformed cells include the primary subject cell and cultures derived therefrom without regard for the number of transfers. It also is understood that all progeny may not be precisely identical in DNA content, due to deliberate or inadvertent mutations. Mutant progeny that have the same function or biological activity as screened for in the originally transformed cell are included.

Isolated nucleic acids also are provided that encode specific antibodies, optionally operably linked to control sequences recognized by a host cell, vectors and host cells comprising the nucleic acids, and recombinant techniques for the production of the antibodies, which may comprise culturing the host cell so that the nucleic acid is expressed and, optionally, recovering the antibody from the host cell culture or culture medium.

A variety of vectors are known in the art. Vector components can include one or more of the following: a signal sequence (that, for example, can direct secretion of the antibody), an origin of replication, one or more selective marker genes (that, for example, can confer antibiotic or other drug resistance, complement auxotrophic deficiencies, or supply critical nutrients not available in the media), an enhancer element, a promoter, and a transcription termination sequence, all of which are well known in the art.

Suitable host cells include prokaryote, yeast, or higher eukaryote cells. Suitable prokaryotes include eubacteria, such as Gram-negative or Gram-positive organisms, for example, Enterobacteriaceae such as *Escherichia*, e.g., *E. coli, Enterobacter, Erwinia, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas*, and *Streptomyces*. In addition to prokaryotes, eukaryotic microbes such as filamentous fungi of yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available, such as *Pichia*, e.g. *P. pastoris, Schizosaccharomyces pombe; Kluyveromyces, Yarrowia; Candida; Trichoderma reesia; Neurospora crassa; Schwanniomyces* such as *Schwanniomyces occidentalis*; and filamentous fungi such as, e.g., *Neurospora, Tolypocladium*, and *Aspergillus* hosts such as *A. nidulans* and *A. niger*.

Suitable host cells for the expression of glycosylated antibodies are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection of such cells are publicly available, e.g., the variant of *Autographa californica* NPV and the Bm-5 strain of *Bombyx mori* NPV.

However, interest has been greatest in vertebrate cells, and propagation of vertebrate cells in culture (tissue culture) has become routine. Examples of useful mammalian host cell-lines are Chinese hamster ovary cells, including CHOKI cells (ATCC CCL61) and Chinese hamster ovary cells/-DHFR (DXB-11, DG-44; Urlaub et al, Proc. Natl. Acad. Sci, USA 77: 4216 (1980)); monkey kidney CV1 line transformed by SV40 (COS-7, ATCC CRL 1651); human embryonic kidney line (293 or 293 cells subcloned for growth in suspension culture, [Graham et al., J. Gen Virol. 36: 59 (1977)]; baby hamster kidney cells (BHK, ATCC CCL 10); mouse Sertoli cells (TM4, Mather, Biol. Reprod. 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human hepatoma cells (Hep G2, RB 8065); mouse mammary tumor (MMT 060562, ATCC CCL51); TRI cells (Mather et al., Annals N.Y. Acad. Sci. 383: 44-68 (1982)); MRC 5 cells and FS4 cells.

The host cells can be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44 (1979), Barnes et al. Anal. Biochem. 102: 255 (1980), U.S. Pat. Nos. 4,767,704; 4,657,866; 4,927,762; 4,560,655; or U.S. Pat. No. 5,122,469; WO90103430; WO 87/00195; or U.S. Pat. Re. No. 30,985 can be used as culture media for the host cells. Preferably, the media are free of animal products. More preferably, the media are free of proteins. Exemplary media include Gibco CD Hybridoma; SAFC EX CELL SP/20; SAFC EX CELL 620-HSF; Cell Grow TurboDoma; and Hyclone HyQ CDM4Mab. Any of these media can be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin™ (rug), trace elements (defined as inorganic compounds usually present at final concentrations in the micromolar range), and glucose or an equivalent energy source. Preferably, the media may be supplemented with L glutamine or L alanyl-L glutamine. Any other necessary supplements also can be included at appropriate concentrations that would be known to those skilled in the art. The culture conditions, such as temperature, pH, and the like, are those previously used with the host cell selected for expression, and will be apparent to the artisan.

In some embodiments, the cell culture and harvest process comprises the following five steps:

1. Thaw and expansion
2. Shake flask expansion
3. WAVE expansion 4. 300 L Bioreactor production
5. Harvest/clarification The antibody composition can be purified using, for example, hydroxylapatite chromatography, cation or anion exchange chromatography, or preferably affinity chromatography, using the antigen of interest or protein A or protein G as an affinity ligand. Protein A can be used to purify antibodies that are based on human γ1, γ2, or γ4 heavy chains (Lindmark et al., J. Immunol. Meth. 62: 1-13 (1983)). Protein G is recommended for all mouse isotypes and for human γ3 (Glass et al., 20 EMBO J. 5: 15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $CH_3$ domain, the Bakerbond ABX™ resin (J. T. Baker, Phillipsburg, 25 NJ.) is useful for purification. Other techniques for protein purification such as ethanol precipitation, Reverse Phase HPLC, chromatofocusing, SDS-PAGE, and ammonium sulfate precipitation are also possible depending on the specific binding agent or antibody to be recovered.

In some embodiments, the purification process comprises the following 6 steps:
1. pH adjustment and Toypearl SP-650M chromatography
2. Toyopearl Super Q-650M chromatography
3. Toyopearl CM-650M chromatography
4. Planova 35N nanofiltration
5. Toypearl phenyl-650M chromatography
6. Final tangential flow filtration (TFF)

The terms "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3-5, and more usually, at least 5 or 8-10 amino acids in a unique spatial conformation.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

Humanized Antibodies

Generally, a humanized antibody has one or more amino acid residues introduced into it from a non-human source. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 3]2:323-327 (1988); Verhoeyen et al., Science, 239: 1534-1536 (1988)], by substituting rodent CDRs or CDR sequences for the corresponding sequences of a human antibody.

Accordingly, such "humanized" antibodies are chimeric antibodies wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

Human Antibodies

Human monoclonal antibodies can be made by hybridoma method. Human myeloma and mouse-human heteromyeloma cell lines for the production of human monoclonal antibodies have been described, for example, by Kozbor, J. Immunol, 133, 3001 (1984), and Brodeur, et al., Monoclonal Antibody Production Techniques and Applications, pp. 51-63 (Marcel Dekker, Inc., New York, 1987).

In some embodiments, transgenic animals (e.g. mice) can be employed that are capable, upon immunization with αβ TCR, or fragments thereof, of producing a repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., Proc. Natl. Acad. Sci. USA 90, 2551-255 (1993); Jakobovits et al., Nature 362, 255-258 (1993). Mendez et al. (Nature Genetics 15: 146-156 [1997]) have further improved the technology and have generated a line of transgenic mice designated as "Xenomouse II" that, when challenged with an antigen, generates high affinity fully human antibodies. This was achieved by germ-line integration of megabase human heavy chain and light chain loci into mice with deletion into endogenous ($J_H$) segment as described above. The Xenomouse H harbors 1,020 kb of human heavy chain locus containing approximately 66 $V_H$ genes, complete $D_H$ and $J_H$ regions and three different constant regions (μ, δ, χ), and also harbors 800 kb of human κ locus containing 32 Vκ genes, Jκ segments and Cκ genes. The antibodies produced in these mice closely resemble that seen in humans in respects, including gene rearrangement, assembly, and repertoire. The human antibodies are preferentially expressed over endogenous antibodies due to deletion in endogenous $J_H$ segment that prevents gene rearrangement in the murine locus.

Alternatively, the phage display technology (McCafferty et al., Nature 348, 552-553 (1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g. Johnson, Kevin S. and Chiswell, David J., Current Opinion in Structural Biology 3, 564-571 (1993). Several sources of V-gene segments can be used for phage display. Clackson et al., Nature 352, 624-628 (1991) isolated a diverse array of anti-oxazolone antibodies from a small random combinatorial library of d % genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222, 581-597 (1991), or Griffith et al., EMBO J. 12, 725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., Bio/Technol. 10, 779-783 [1992]). In this method, the affinity of "primary" human antibodies obtained by phage display can be improved by sequentially replacing the heavy and light chain V region genes with repertoires of naturally occurring variants (repertoires) of V domain genes obtained from unimmunized donors. This techniques allows the production of antibodies and antibody fragments with affinities in the nM range. A strategy for snaking cry large phage antibody repertoires has been described by Waterhouse et al., Nucl. Acids Res. 21, 2265-2266 (1993). Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras, Selection on antigen results in isolation of human variable capable of restoring a functional antigen-binding site, i.e. the epitope governs (imprints) the choice of partner. When the process is repeated in order to replace the remaining rodent V domain, a human antibody is obtained (see PCT patent application WO 93/06213, published 1 Apr. 1993). Unlike traditional humanization of rodent antibodies by CDR grafting, this technique provides completely human antibodies, which have no framework or CDR residues of rodent origin.

As discussed in detail below, the antibodies of the invention may optionally comprise monomeric antibodies, dimeric antibodies, as well as multivalent forms of antibodies. Those skilled in the art may construct such dimers or multivalent forms by techniques known in the art and using the anti-αβ TCR antibodies disclosed herein. Methods for preparing monovalent antibodies are also well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Antibody Fragments

In certain embodiments, the anti-αβ TCR antibody of the present invention (including murine, human and humanized antibodies, and antibody variants) is an antibody fragment. Various techniques have been developed for the production of antibody fragments, Traditionally, these fragments were derived via proteolytic digestion of intact antibodies (see, e.g., Morimoto et al., J. Biochem. Biophys. Methods 24:107-117 (1992) and Brennan et al., Science 229:81 (1985)). However, these fragments can now be produced directly by recombinant host cells. For example, Fab'-SH fragments can be directly recovered from E. coli and chemically coupled to form F(ab') fragments (Carter et al., Bio/Technology 10:163-167 (1992)). In one embodiment, single chain variable fragments (say) are produced from E. coli using techniques known in the art. In another embodiment, the F(ab')$_2$ is formed using the leucine zipper GCN4 to promote assembly of the F(ab')$_2$ molecule. According to another approach, Fv, Fab or F(ab')$_2$ fragments can be isolated directly from recombinant host cell culture. A variety of techniques for the production of antibody fragments will be apparent to the skilled practitioner. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields an F(ab')$_2$ fragment that has two antigen combining sites and is still capable of cross-linking antigen.

The Fab fragments produced in the antibody digestion also contain the constant domains of the light chain and the first constant domain (CH$_1$) of the heavy chain. Fab' fragments differ from Fab fragments by the addition of a few residues at the carboxy terminus of the heavy chain CH$_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells.

In some embodiments, antibodies or antibody fragments are isolated from antibody phage libraries generated using the techniques described in, for example, McCafferty et al., Nature, 348: 552554 (1990). Clackson et al., Nature, 352: 624-628 (1991) and Marks et al., J. Mol. Biol., 222: 581-597 (1991) describe the isolation of murine and human antibodies, respectively, using phage libraries. Subsequent publications describe the production of high affinity (nM range) human antibodies by chain shuffling (Marks et al, BioTechnology, 10: 779-783 (1992)), as well as combinatorial infection and in vivo recombination as a strategy for constructing very lame phage libraries (e.g., Waterhouse et al., Nuc. Acids. Res., 21: 2265-2266 (1993)). Thus, these techniques, and similar techniques, are viable alternatives to traditional monoclonal antibody hybridoma techniques for isolation of monoclonal antibodies.

Also, the DNA may be modified, for example, by substituting the coding sequence for human heavy- and light-chain constant domains in place of the homologous murine sequences (e.g., U.S. Pat. No. 4,816,567, and Morrison, et al., Proc. Nat. Acad. Sci. USA, 81: 6851 (1984), both of which are hereby incorporated by reference), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Amino Acid Sequence Variants of Antibodies

Amino acid sequence variants of the anti-αβ TCR antibodies are prepared by introducing appropriate nucleotide changes into the anti-αβ TCR antibody DNA, or by peptide synthesis. Such variants include, for example, deletions from, and/or insertions into and/or substitutions of, residues within the amino acid sequences of the anti-αβ TCR antibodies of the examples herein. Any combination of deletion, insertion, and substitution is made to arrive at the final construct, provided that the final construct possesses the desired characteristics. The amino acid chances also may alter post-translational processes of the humanized or variant anti-αβ TCR antibody, such as changing the number or position of glycosylation sites.

A useful method for identification of certain residues or regions of the anti-αβ TCR antibody that are preferred locations for mutagenesis is called "alanine scanning mutagenesis," as described by Cunningham and Wells Science, 244: 1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with DR4 antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-αβ TCR antibody variants are screened for the desired activity.

Amino acid sequence insertions include amino- and/or carboxyl-terminal fusions ranging in length from one residue to polypeptides containing a hundred or more residues, as well as intra-sequence insertions of single or multiple amino acid residues. Examples of terminal insertions include an anti-αβ TCR antibody with an NI-terminal methionyl residue of the antibody fused to an epitope tag. Other insertional variants of the anti-αβ TCR antibody molecule include the fusion to the N- or C-terminus of the anti-αβ TCR antibody of an enzyme or a polypeptide which increases the serum half-life of the antibody.

Another type of variant is an amino acid substitution variant. These variants have at least one amino acid residue in the anti-αβ TCR antibody molecule removed and a different residue inserted in its place. The sites of greatest interest for substitutional mutagenesis include the hypervariable regions, but FR alterations are also contemplated. Conservative substitutions are indicated below. If such substitutions result in a change in biological activity, then more substantial changes may be introduced and the products screened.

Substantial modifications in the biological properties of the antibody are accomplished by selecting substitutions that differ significantly in their effect on maintaining (a) the structure of the polypeptide backbone in the area of the substitution, for example, as a sheet or helical conformation, (h) the charge or hydrophobicity of the molecule at the target site, or (c) the bulk of the side chain. Naturally occurring residues are divided into groups based on common side-chain properties.

The following eight groups each contain amino acids that are regarded conservative substitutions for one another: 1) Alanine (A) and Glycine (0); 2) Aspartic acid (I)) and Glutamic acid (E); 3) Asparagine (N) and Glutamine (Q); 4) Arginine (R) and Lysine (K); 5) Isoleucine (I), Leucine (L), Methionine (M) and Valine (V); 6) Phenylalanine (F), Tyrosine (Y) and Tryptophan (W); 7) Serine (S) and Threonine (T); and 8) Cysteine (C) and Methionine (M) (see, e.g., Creighton. Proteins, W.H. Freeman and Co., New York (1984)).

In some embodiments, conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gin; ile/leu ear val; leu/ile or val; lys/arg or gin or glu; met/leu or tyr or ile; phe/met or leu or tyr; ser/thr; thr/ser; trp/tyr; tyr/trp or phe; val/ile leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine Histidine (H); 5) Isoleucine (I), Leucine (L), Methionine (M), Valine (V); and 6) Phenylalanine (F), sine (Y), Tryptophan (W); (see also, e.g., Creighton, Proteins, W.H. Freeman and Company (1984); Schultz and Schimer, Principles of Protein Structure, Springer-Verlag (1979)). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations."

Non-conservative substitutions will entail exchanging a member of one of these classes for another class. Any cysteine residue not involved in maintaining the proper conformation of the humanized or variant anti-αβ TCR antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or in addition, it may be beneficial to analyze a crystal structure of the antigen-antibody complex to identify contact points between the antibody and human DR4. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Glycosylation Variants of Antibodies

Antibodies are glycosylated at conserved positions in their constant regions (Jefferis and Lund, Chem. Immunol. 65:111-128 [1997]; Wright and Morrison, TibTECH 15:26-32 [1997]). The oligosaccharide side chains of the immunoglobulins affect the proteins function (Boyd et al., Mol. Immunol. 32:1311-1318 [1996]; Wittwe and Howard, Biochem. 29:4175-4180 [1990]), and the intramolecular interaction between portions of the glycoprotein which can affect the conformation and presented three-dimensional surface of the glycoprotein (Hefferis and Lund, supra; Wyss and Wagner, Current Opin. Biotech. 7:409-416 [1996]). Oligosaccharides may also serve to target a given glycoprotein to certain molecules based upon specific recognition structures. For example, it has been reported that in agalactosylated IgG, the oligosaccharide moiety 'flips' out of the inter-$CH_2$ space and terminal N-acetylglucosamine residues become available to bind mannose binding protein (Malhotra et al., Nature Med. 1:237-243 (1995]). Removal by glycopeptidase of the oligosaccharides from CAMPATH-1H (a recombinant humanized murine monoclonal IgG1 antibody which recognizes the CDw52 antigen of human lymphocytes) produced in Chinese Hamster Ovary (CHO) cells resulted in a complete reduction in complement mediated lysis (CMCL) (Boyd et al., Mol. Immunol. 32:1311-1318 [1996]), while selective removal of sialic acid residues using neuraminidase resulted in no loss of DMCL. Glycosylation of antibodies has also been reported to affect antibody-dependent-cellular cytotoxicity (ADCC). In particular, CHO cells with tetracycline-regulated expression of .beta.(1,4)-N-acetylglucosaminyltransferase III (GnTIII), a glycosyltransferase catalyzing formation of bisecting GlcNAc, was reported to have improved ADCC activity (Umana et al., Mature Biotech. 17:176-180 [1999]).

Glycosylation variants of antibodies are variants in which the glycosylation pattern of an antibody is altered. By altering is meant deleting one or more carbohydrate moieties found in the antibody, adding one or more carbohydrate moieties to the antibody, changing the composition of glycosylation (glycosylation pattern), the extent of glycosylation, etc. Glycosylation variants may, for example, be prepared by removing, changing and/or adding one or more glycosylation sites in the nucleic acid sequence encoding the antibody, and expressing and translating the nucleic acid in a prokaryotic cell expression system.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site, O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-αβ TCR antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-αβ TCR antibody.

The glycosylation (including glycosylation pattern) of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, significant variations in the glycosylation pattern of the antibodies can be expected (see, e.g. Hse et al., J. Biol. Chem. 272:9062-9070 [1997]). Various methods have been proposed to alter the glycosylation pattern achieved in a particular host organism including introducing or overexpressing certain enzymes involved oligosaccharide production (U.S. Pat. Nos. 5,047,335; 5,510,261 and 5,278,299). Glycosylation, or certain types of glycosylation, can be enzymatically removed from the glycoprotein, for example using endoglycosidase H (Endo H). In addition, the recombinant host cell can be genetically engineered, e.g. make defective in processing certain types of polysaccharides. These and similar techniques are well known in the art. The glycosylation structure of antibodies can be readily analyzed by conventional techniques of carbohydrate analysis, including lectin chromatography, NMR, Mass spectrometry, HPLC, GPC, monosaccharide compositional analysis, sequential enzymatic digestion, and HPAEC-PAD, which uses high pH anion exchange chromatography to, separate oligosaccharides based on charge. Methods for releasing oligosaccharides for analytical purposes are also known, and include, without limitation, enzymatic treatment (commonly performed using peptide-N-glycosidase F/endo-α-galactosidase), elimination using harsh alkaline environment to release mainly O-linked structures, and chemical methods using anhydrous hydrazine to release both N- and O-linked oligosaccharides. In some embodiments, the anti-αβ TCR antibodies of the present invention can be glycosylated. In some embodiments of the present invention, the anti-αβ TCR antibodies of the present invention can be unglycosylated. In some embodiments, the antibody or antigen binding fragments of the invention include antibodies or antibody fragments that bind to human αβ TCR that have or are engineered to have the same glycosylation pattern as the antibody produced from the hybridoma TOL101 MCB (TOL101). By "same glycosylation pattern" or "equivalent glycosylation pattern" it is intended that the antibodies of the invention have the same number and/or type of glycosylation sites as the antibody produced from the hybridoma TOL101 MCB (TOL101) such that the overall glycosylation signature or N- and O-linked oligosaccharide composition of the antibodies of the invention is similar to the glycosylation signature or N- and O-linked oligosaccharide composition of the antibody produced from the hybridoma TOL101 MCB (TOL101), as measured using the traditional techniques disclosed herein, resulting in the antibodies of the invention having at least one of the improved functional or clinical properties of TOL101 described herein. In addition, the antibody or antigen binding fragments of the invention may be glycosylated at equivalent or corresponding residues as the antibody produced by the hybridoma TOL101 MCB (TOL101). By "equivalent or corresponding residues" it is contemplated that the antibody or antigen binding fragments of the invention are glycosylated at residues that are within 35, within 30, within 25, within 20, within 15, within 10, or within 5 amino acid residues of the glycosylated residue in the antibody produced by the hybridoma TOL101 MCB (TOL101) when the two antibody sequences are aligned using publicly available computer software and the residue numbers of the glycosylated residues are identified according to Kabat such that the antibodies or antigen binding fragments of the invention have at least one of the improved functional or clinical properties of TOL101 over the prior art as described herein. Examples of suitable computer software include programs include the "Staden Package", "DNA Star", "MacVector", GCG "Wisconsin Package" (Genetics Computer Group, Madison, Wis.) and "NCBI toolbox" (National Center for Biotechnology Information). As discussed herein, methods of identifying, comparing, altering and/or engineering the glycosylation of an antibody are also well known in the art.

Exemplary Antibodies

The invention disclosed herein has a number of exemplary embodiments. A variety of the typical embodiments of the invention are described below. The following embodiments are offered for illustrative purposes only, and are not intended to limit the scope of the present invention in any way. In certain embodiments of the methods, assays and compositions of the present invention, the anti-αβ TCR antibody or antibody fragment thereof comprises TOL101 antibody or antibody fragment thereof which is an isolated mouse IgM monoclonal antibody which binds to a αβ TCR and is produced by the hybridoma TOL101 MCB.

Anti-αβ TCR Monoclonal Antibody Properties

In various embodiments, anti-αβ TCR antibodies of the present invention bind specifically to a mammalian αβ TCR, for example, a human αβ TCR. In some embodiments, the anti-αβ TCR antibodies of the present invention bind to CD3+ T cells without a γδ TCR. Furthermore, anti-αβ TCR antibodies of the present invention do not bind to cells expressing markers such as CD14, CD16, B220 and CD19, further highlighting their specificity for the αβ T– cell. For example, homogenous, robust and reproducible anti-all TCR antibody binding of TOL101 has been observed in over 130 clinical patients and 20 healthy volunteers, as well as to common immortalized T-cell lines. Because anti αβ TCR antibodies of the present invention bind to the entire population of αβ T-cells in a homogenous manner, it is believed that the anti-αβ TCR antibodies of the present invention bind a constant region of the αβ TCR.

Other anti-αβ TCR antibodies known in the art, such as T10B9.1A-31 (T10B9) and MEDI-500, are immunoglobulin M kappa murine monoclonal antibodies (mAb) directed against the alpha-beta (αβ) heterodimer of the T-lymphocyte receptor complex. T10B9 is commercially available from BD Pharminigen™ (San Diego, Calif., USA) as Catalog Numbers 561674, 555548, 5555547, 561673. T10B9 has a relatively short duration of action, depleting T-cells for 10 to 14 days, unlike the protracted depletion seen with thymoglobulin and Campath-1H. Anti-αβ TCR antibodies such as T10B9 and MEDI-500 are nonmitogenic (i.e. do not induce cell proliferation) in soluble form at low concentrations; however, high concentrations of antibody in soluble form, or either low or high concentrations of plate-bound antibody (i.e., crosslinked antibody) induce cell proliferation (Brown et al. Clinical Transplantation 10; 607-613 [1996]). In contrast, anti-αβ TCR monoclonal antibodies or antibody fragments thereof of the present invention, which do not include MEDI-500 or T10B9 or fragments thereof, are non-mitogenic at high and low concentrations and in both soluble and plate-bound form. T10B9 and MEDI-500 are sometimes used interchangeably in the literature, and have each previously been tested as therapeutic antibodies for indications such as treatment for allograft rejection and hematological malignancies. However, the clinical use of these antibodies was associated with adverse events and significant human-anti-mouse antibody responses (HAMA) (Wail et al. Transplantation 64; 274-281 [1997]). Thus, there is a need in the art for anti-αβ TCR antibodies that provide efficacy while minimizing adverse events. Surprisingly, TOL101 which is a murine antibody and is specific for αβ TCR, exhibited robust T cell suppression with minimal adverse events and minimal HAMA responses. Without wishing to be bound by theory, it is thought that the posttranslational modifications of TOL101, including, for example, the glycosylation and/or conformation of the antibody, are at least in part responsible for the superior clinical efficacy and safety of the antibody of the present invention over the antibodies of the prior art. In addition, anti-αβ TCR antibodies of the present invention (including TOL101) do not deplete the numbers of circulating CD3+ T-cells significantly (for example, by an amount greater than 10% when compared to a vehicle control) when administered systemically at doses ranging from 0 to 42 mg/mL per day for 1 to 5 days. Instead, without wishing to be bound by theory, it is thought that the anti-αβ TCR antibodies of the present invention (including TOL101) downregulate the CD3 complex on αβ TCR+ T cells, including the TCR itself, thus rendering the T cells unable to respond to antigen. As used herein, the terms "T cell depletion" and "T cell deletion" refer to the reduction of T cell numbers (e.g., circulating T cells in a subject). T cell depletion or deletion may be achieved by inducing cell death in a T Uses for Anti-αβ TCR Antibodies and Antibody Fragments Thereof The anti-αβ TCR antibodies or antibody fragments thereof of the invention have various utilities, particularly related to negative modulation of αβ TCR+ T-cells. For example, anti-αβ TCR antibodies may be employed in methods for treating pathological conditions in mammals, for example, humans, primates, and laboratory animals. It is contemplated herein that the anti-αβ TCR antibodies may be employed in the treatment and/or prevention of autoimmune diseases, inflammatory diseases and graft-versus host or transplant tissue rejection related conditions and diseases. In the methods of the present invention, the anti-αβ TCR antibodies or antibody fragments thereof, can be administered to a mammal, for example a human subject in need thereof, alone or in combination with still other secondary adjunctive therapeutic agents or techniques.

By way of illustration only, autoimmune and inflammation diseases for which treatment with the anti-αβ TCR antibodies or antibody fragments can provide efficacy can include: asthma (for example, allergic asthma, non-allergic asthma, exercised-induced asthma, occupational asthma, and nocturnal asthma), allergy, allergic airway inflammation, allergic encephalomyelitis, autoimmune arthritis, rheumatoid arthritis, Juvenile rheumatoid arthritis, reactive arthritis, psoriatic arthritis, sacroiliitis, isolated acute anterior uveitis, undifferentiated spondyloarthropathy, Type I Diabetes Mellitus, Multiple Sclerosis, Systemic Lupus Erythematosus, glomerulonephritis, Hashimoto's thyroiditis, Graves' disease, Scleroderma, Celiac disease, Crohn's disease, inflammatory bowel disease, ulcerative colitis, ankylosing spondylitis, Sjogren's syndrome, psoriasis, contact dermatitis, Goodpasture's syndrome, Addison's disease, Wegener's granulomatosis, Primary biliary cirrhosis, Sclerosing cholangitis, Autoimmune hepatitis, Polymyalgia Rheumatica, Bechet's disease, Guillain-Barre syndrome, various vasculitides, uveoretinitis, thyroditis, myasthenia gravis, immunoglobulin nephropathies, myocarditis, and progressive systemic sclerosis. In some embodiments, an inflammatory disease can include an inflammatory condition or disease for example, chronic obstructive pulmonary disease (COPD), bronchitis, emphysema or acute respiratory distress syndrome (ARDS), in another aspect, the inflammatory condition or disease can include a disease, condition or disorder that is associated with elevated levels of inflammatory cytokines, in various aspects, the inflammatory cytokine is IL-2, IL-4 or IL-5; or the inflammatory cytokine is IFN-γ; or the inflammatory cytokine is TNF-α. In particular embodiments, the autoimmune disease is type I diabetes or multiple sclerosis.

Embodiments of the present invention provide for methods for treating a subject having Of in need of a transplant. In accordance with these embodiments, a subject may be treated with a composition for reducing the risk of a transplant rejection or a side-effect of a transplant rejection in a subject. In accordance with this method the subject can be administered a composition comprising anti-αβ TCR antibodies or antibody fragments thereof that is capable of reducing T-cell activation. The composition may be administered before transplantation, during transplantation, after transplantation or combination thereof. In some embodiments, the anti-αβ TCR antibodies or antibody fragments thereof of the present invention are administered in order to prevent or reduce the severity of transplant rejection. In other embodiments, the anti-αβ TCR antibodies or antibody fragments thereof of the present invention are administered in order to treat a transplant rejection that is occurring or has already occurred. In addition, the composition may further include one or more anti-transplant rejection agent, anti-inflammatory agent, immunosuppressive agent, immunomodulatory agent, antimicrobial agent, or a combination thereof.

In certain embodiments of the invention, a composition comprising anti-αβ TCR antibodies or antibody fragments thereof is capable of significantly reducing cytokine activation associated with T-cell activation. A tissue transplant of the present invention may include an organ transplant and/or a non-organ transplant. For example lung, kidney, heart, liver, cornea, skin, stem cells, soft tissue (e.g. facial component transplant), intestinal transplants, bone marrow, pancreatic islet, pancreas transplant or combination thereof are contemplated.

Embodiments of the present invention provide for methods for ameliorating symptoms or signs experienced by a subject having or in need of a transplant. In accordance with these embodiments, symptoms or signs may include conditions associated with graft versus host disease (GVHD), or graft rejection. In one example, methods disclosed herein may be used to treat a subject undergoing renal transplantation. In another embodiment, symptoms or signs may include but is not limited to one or more of the following, kidney failure, lung failure, heart failure, malaise, fever, dry cough, anorexia, weight loss, myalgias, and chest pains, ventilatory compromise, sweating, nausea, vomiting, fever, abdominal pain, bloody diarrhea, mucosal ulcerations, reduced renal function (increased creatinine, decreased urine output), reduced pulmonary function (increased shortness of breath, fever, cough, sputum, hypoxemia), reduced cardiac function (shortness of breath, chest pain, fatigue, pulmonary or peripheral edema, valvulopathy), reduced islet function (increased glucose, diabetes melitus), graft versus host disease (gastrointestinal (GI) ulceration, pulmonary failure, skin ulceration, coagulopothy, CNS dysfunction (mental status changes, coma) CMV (cytomeglovirus infection, viral, fungal parasitic infection)).

Embodiments of the present invention provide methods for promoting prolonged graft survival and function in a subject including administering to a subject in need thereof a therapeutically effective amount of a composition including anti-αβ TCR antibodies or antibody fragments thereof. Embodiments of the present invention provide for methods for treating a subject in need of an immunotolerance therapy. In accordance with these embodiments, a subject may be treated with a composition for reducing the risk of a dysfunctional immune responses or a side-effect of a dysfunctional immune response in a subject. In another embodiment, methods herein provide for inducing immune tolerance specific for a graft and/or reduce the need for immunosuppressive therapy. In accordance with this embodiment, the immune system of the transplant recipient may have reduced or lost the specific ability to attack the graft while maintaining its ability to mount any other type of immune attack. In accordance with this method, the transplant recipient can be administered with a composition including anti-αβ TCR antibodies or antibody fragments thereof, for example, TOL101, in accordance with these embodiments, immunotolerance therapy can include inhibiting cytokine production using anti-αβ TCR antibodies or antibody fragments thereof.

Embodiments of the present invention provide for methods for reducing TNF-α (tumor necrosis factor alpha) levels in a subject including administering a composition including anti-αβ TCR antibodies or antibody fragments thereof to a subject in need of such a treatment. Embodiments of the present invention provide for methods for treating a subject in need of an immunotolerance therapy. In accordance with these embodiments methods are provided for reducing NO production and/or reducing apoptosis and/or inhibiting cytomegleovirus (infection and reactivation) including administering a composition including anti-αβ TCR antibodies or antibody fragments thereof. In certain embodiments of the invention, a composition capable of significantly reducing T-cell activation in vivo and in vitro.

In certain embodiments of the present invention, secondary active agents can be used in conjunction with anti-αβ TCR antibodies or antibody fragments thereof of the present invention. In exemplary embodiments, anti-inflammatory compound or immunomodulatory drugs can include but is not limited to one or more of interferon, interferon derivatives including betaseron, beta-interferon, prostane derivatives including iloprost, cicaprost; glucocorticoids including cortisol, prednisolone, methyl-prednisolone, dexamethasone; immunsuppressives including cyclosporine A, FK-506, methoxsalene, thalidomide, sulfasalazine, azathioprine, methotrexate; lipoxygenase inhibitors comprising zileutone, MK-886, WY-50295, SC-45662, SC-41661A, BI-L-357; leukotriene antagonists; peptide derivatives including ACTH and analogs thereof; soluble TNF-receptors; TNF-antibodies; soluble receptors of interleukins, other cytokines, T-cell-proteins; antibodies against receptors of interleukins, other cytokines, T-cell-proteins; and calcipotriols; Celcept® mycophenolate mofetil, and analogs thereof taken either alone or in combination.

The anti-αβ TCR antibodies or antibody fragments thereof of the present invention may be further recombinantly fused or coupled to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays (such as radionuclides, radioisotopes, fluorescent labels, luminescent labels, bioluminescent labels or biotin) and effector molecules such as heterologous polypeptides, drugs, enzyme or toxins. See, e.g., PCT publications WO 92/08495; WO 91/14438.

Embodiments of the present invention provide for methods for reducing graft rejection in a subject. In accordance with these embodiments, a subject may be treated with a therapeutically effective amount of an anti-αβ TCR antibody or antibody fragments thereof, for reducing the risk of graft rejection responses or a side-effect of a graft rejection response in a subject. In accordance with this method, the subject can be administered a composition including anti-αβ TCR antibodies or antibody fragments thereof. In one example, reducing graft rejection may include reducing the symptoms associated with graft rejection in a subject having an organ transplant, such as a kidney transplant or a bowel transplant or a non-organ transplant, such as a bone marrow transplant soft tissue transplant.

In various embodiments, diagnosis in mammals of the various pathological conditions described herein can be made by the skilled practitioner. Diagnostic techniques are available in the art which allow, e.g., for the diagnosis or detection of autoimmune and inflammation related diseases in a mammal. For instance, autoimmune and inflammation related diseases may be identified through techniques, including but not limited to, identifying the types and population of certain lymphocytes, the presence of autoantibodies, the presence and quantity of disease specific cytokines, by the presence of fever and the like. For example, in systemic lupus erythematosus, the central mediator of disease is the production of auto-reactive antibodies to self proteins/tissues and the subsequent generation of immune-mediated inflammation. Multiple organs and systems are affected clinically including kidney, lung, musculoskeletal system, mucocutaneous, eye, central nervous system, cardiovascular system, gastrointestinal tract, bone marrow and blood. SLE can be diagnosed using a variety of rheumatological and hematological tests for example, the presence and quantity of certain autoantibodies, for example, a positive anti-nuclear antibody (ANA) test, presence of anti-nRNP A, anti-nRNP C, anti-Sm, anti-Ro, anti-La, and anti-dsDNA antibodies.

Rheumatoid arthritis (RA) is a chronic systemic autoimmune inflammatory disease that mainly involves the synovial membrane of multiple joints with resultant injury to the articular cartilage. The pathogenesis is T lymphocyte dependent and is associated with the production of rheumatoid factors, auto-antibodies directed against self IgG, with the resultant formation of immune complexes that attain high levels in joint fluid and blood. These complexes in the joint may induce the marked infiltrate of lymphocytes and monocytes into the synovium and subsequent marked synovial changes; the joint space/fluid if infiltrated by similar cells with the addition of numerous neutrophils. Tissues affected are primarily the joints, often in symmetrical pattern. However, extra-articular disease also occurs in two major forms. One form is the development of extra-articular lesions with ongoing progressive joint disease and typical lesions of pulmonary fibrosis, vasculitis, and cutaneous ulcers. The second form of extra-articular disease is the so called Felty's syndrome which occurs late in the RA disease course, sometimes after joint disease has become quiescent, and involves the presence of neutropenia, thrombocytopenia and splenomegaly. This can be accompanied by vasculitis in multiple organs with formations of infarcts, skin ulcers and gangrene. Patients often also develop rheumatoid nodules in the subcutis tissue overlying affected joints; the nodules late stage have necrotic centers surrounded by a mixed inflammatory cell infiltrate. Other manifestations which can occur in RA include: pericarditis, pleuritis, coronary arteritis, interstitial pneumonitis with pulmonary fibrosis, keratoconjunctivitis sicca, and rheumatoid nodules.

Juvenile chronic arthritis is a chronic idiopathic inflammatory disease which begins often at less than 16 years of age, its phenotype has some similarities to RA; some patients which are rheumatoid factor positive are classified as juvenile rheumatoid arthritis. The disease is sub-classified into three major categories: pauciarticular, polyarticular, and systemic. The arthritis can be severe and is typically destructive and leads to joint ankylosis and retarded growth. Other manifestations can include chronic anterior uveitis and systemic amyloidosis.

Spondyloarthropathies are a group of disorders with some common clinical features and the common association with the expression of HLA-B27 gene product. The disorders include: ankylosing sponylitis, Reiter's syndrome (reactive arthritis), arthritis associated with inflammatory bowel disease, spondylitis associated with psoriasis, juvenile onset spondyloarthropathy and undifferentiated spondyloarthropathy. Distinguishing features include sacroileitis with or without spondylitis; inflammatory asymmetric arthritis; association with HLA-B27 (a serologically defined allele of the HLA-B locus of class I MHC); ocular inflammation, and absence of autoantibodies associated with other rheumatoid disease. The cell most implicated as key to induction of the disease is the CD8+ T lymphocyte, a cell which targets antigen presented by class I MHC molecules. CD8+ T-cells may react against the class I MHC allele HLA-B27 as if it were a foreign peptide expressed by MHC class I molecules. It has been hypothesized that an epitope of HLA-B27 may mimic a bacterial or other microbial antigenic epitope and thus induces a CD8+ T-cells response.

Systemic sclerosis (scleroderma) has an unknown etiology. A hallmark of the disease is induration of the skin; likely this is induced by an active inflammatory process. Scleroderma can be localized or systemic; vascular lesions are common and endothelial cell injury in the microvasculature is an early and important event in the development of systemic sclerosis; the vascular injury may be immune mediated. An immunologic basis is implied by the presence of mononuclear cell infiltrates in the cutaneous lesions and the presence of anti-nuclear antibodies in many patients. ICAM-1 is often upregulated on the cell surface of fibroblasts in skin lesions suggesting that T-cell interaction with these cells may have a role in the pathogenesis of the disease. Other organs involved include: the gastrointestinal tract: smooth muscle atrophy and fibrosis resulting in abnormal peristalsis/motility; kidney: concentric subendothelial intimal proliferation affecting small arcuate and interlobular arteries with resultant reduced renal cortical blood flow, results in proteinuria, azotemia and hypertension; skeletal muscle: atrophy, interstitial fibrosis; inflammation; lung: interstitial pneumonitis and interstitial fibrosis; and heart: contraction band necrosis, scarring/fibrosis.

Idiopathic inflammatory myopathies including dermatomyositis, polymyositis and others are disorders of chronic muscle inflammation of unknown etiology resulting in muscle weakness. Muscle injury/inflammation is often symmetric and progressive. Autoantibodies are associated with most forms. These myositis-specific autoantibodies are directed against and inhibit the function of components, proteins and RNA's, involved in protein synthesis.

Sjogren's syndrome is due to immune-mediated inflammation and subsequent functional destruction of the tear glands and salivary glands. The disease can be associated with or accompanied by inflammatory connective tissue diseases. The disease is associated with autoantibody production against Ro and La antigens, both of which are small RNA-protein complexes. Lesions result in keratoconjunctivitis sicca, xerostomia, with other manifestations or associations including bilary cirrhosis, peripheral or sensory neuropathy, and palpable purpura.

Systemic vasculitis are diseases in which the primary lesion is inflammation and subsequent damage to blood vessels which results in ischemia/necrosis/degeneration to tissues supplied by the affected vessels and eventual end-organ dysfunction in some cases. Vasculitides can also occur as a secondary lesion or sequelae to other immune-inflammatory mediated diseases such as rheumatoid arthritis, systemic, sclerosis, etc. particularly in diseases also associated with the formation of immune complexes. Diseases in the primary systemic vasculitis group include: systemic necrotizing vasculitis: polyarteritis nodosa, allergic angiitis and granulomatosis, polyangiitis; Wegener's granulomatosis; lymphomatoid granulomatosis; and giant-cell arteritis. Miscellaneous vasculitides include: mucocutaneous lymph node syndrome (MLNS or Kawasaki's disease), isolated CNS vasculitis, Behet's disease, thromboangiitis obliterans (Buerger's disease) and cutaneous necrotizing venulitis. The pathogenic mechanism of most of the types of vasculitis listed is believed to be primarily due to the deposition of immunoglobulin complexes in the vessel wall and subsequent induction of an inflammatory response either via ADCC, complement activation, or both.

Sarcoidosis is a condition of unknown etiology which is characterized by the presence of epithelioid granulomas in nearly any tissue in the body; involvement of the lung is most common. The pathogenesis involves the persistence of activated macrophages and lymphoid cells at sites of the disease with subsequent chronic sequelae resultant from the release of locally and systemically active products released by these cell types.

Autoimmune hemolytic anemia including autoimmune hemolytic anemia, immune pancytopenia, and paroxysmal noctural hemoglobinuria is a result of production of antibodies that react with antigens expressed on the surface of red blood cells (and in some cases other blood cells including platelets as well) and is a reflection of the removal of those antibody coated cells via complement mediated lysis and/or ADCC/Fc-receptor-mediated mechanisms.

In autoimmune thrombocytopenia including thrombocytopenic purpura, and immune-mediated thrombocytopenia in other clinical settings, platelet destruction/removal occurs as a result of either antibody or complement attaching to platelets and subsequent removal by complement lysis, ADCC or FC-receptor mediated mechanisms.

Thyroiditis including Grave's disease, Hashimoto's thyroiditis, juvenile, lymphocytic thyroiditis, and atrophic thyroiditis, are the result of an autoimmune response against thyroid antigens with production of antibodies that react with proteins present in and often specific for the thyroid gland. Experimental models exist including spontaneous models: rats (BUF and BB rats) and chickens (obese chicken strain); inducible models: immunization of animals with either thyroglobulin, thyroid microsomal antigen (thyroid peroxidase).

Type I diabetes mellitus or insulin-dependent diabetes is the autoimmune destruction of pancreatic islet $\beta$ cells. This destruction is mediated by autoantibodies and auto-reactive T-cells. Antibodies to insulin or the insulin receptor can also produce the phenotype of insulin-non-responsiveness.

Immune mediated renal diseases, including glomerulonephritis and tubulointerstitial nephritis, are the result of antibody or T lymphocyte mediated injury to renal tissue either directly as a result of the production of autoreactive antibodies or T-cells against renal antigens or indirectly as a result of the deposition of antibodies and/or immune complexes in the kidney that are reactive against other, non-renal antigens. Thus other immune-mediated diseases that result in the formation of immune-complexes can also induce immune mediated renal disease as an indirect sequelae. Both direct and indirect immune mechanisms result in inflammatory response that produces/induces lesion development in renal tissues with resultant organ function impairment and in some cases progression to renal failure. Both humoral and cellular immune mechanisms can be involved in the pathogenesis of lesions Demyelinating diseases of the central and peripheral nervous systems, including Multiple Sclerosis; idiopathic demyelinating polyneuropathy or Guillain-Barr syndrome; and Chronic Inflammatory Demyelinating Polyneuropathy, are believed to have an autoimmune basis and result in nerve demyelination as a result of damage caused to oligodendrocytes or to myelin directly. In Multiple Sclerosis there is evidence to suggest that disease induction and progression is dependent on T lymphocytes. Multiple Sclerosis typically has either a relapsing-remitting course or a chronic progressive course. The etiology is unknown; however, viral infections, genetic predisposition, environment, and autoimmunity all may contribute to the etiology and/or pathogenesis of the disease. Lesions contain infiltrates of predominantly T lymphocyte mediated, microglial cells and infiltrating macrophages; CD4+ T lymphocytes are the predominant cell type at lesion sites. The mechanism of oligodendrocyte cell death and subsequent demyelination is not known but is likely that it is T lymphocyte driven. In various aspects of the present invention, administration of the anti-$\alpha\beta$ TCR antibodies of the present invention is seen as a rational first step in preventing further myelin destruction and patient morbidity. In the animal model of MS, Experimental Autoimmune Encephalomyelitis, T cell antagonism can completely abrogate disease. Without being bound to any particular theory, it is believed that the administration of the anti-4 TCR antibodies of the present invention in the animal model of multiple sclerosis, experimental autoimmune encephalomyelitis, leads to T-cell antagonism which can completely abrogate disease. While the specific mechanism(s) that operate in reducing, abrogating or reversing the symptoms and pathogenesis of the disease is not necessary to the understanding of the present invention, it is believed that the administration of anti-αβ TCR antibodies of the present invention to a recent onset Multiple Sclerosis patient not only silences the autoreactive immune response, but also prevents epitope spreading to other myelin epitopes, inhibiting progression of disease.

Criteria for determining the stages of multiple sclerosis disease are well known. For example, symptoms associated with recent onset can include one or more of the following: fatigue, visual disorders, numbness dizziness/vertigo, bladder and bowel dysfunction, weakness, tremor, impaired mobility, sexual dysfunction, slurred speech, spasticity (leg stiffness), swallowing disorders, chronic aching pain, depression, mild cognitive and memory difficulties. While not all of these symptoms may be present in recent-onset multiple sclerosis, some combination of these is usually detected. Other stages or types of multiple sclerosis can include: benign multiple sclerosis, relapsing/remitting multiple sclerosis, secondary/progressive multiple sclerosis, primary/progressive multiple sclerosis, and progressive/relapsing multiple sclerosis. These stages of multiple sclerosis are well known in the art and can be verified using neurologically acceptable tests and diagnostic methods known in the art. For example, the number of contrast enhancing lesions (CEL) can be determined from Magnetic Resonance Imaging (MRI) studies. Additionally, functional assessments of Multiple Sclerosis patients are known in the art and include, for example, the mean Scripps Neurological Rating Scale (SNRS); the mean Expanded Disability Status Scale (EDSS); and the mean Multiple Sclerosis Functional Composite (MSFC).

As used herein, treatment of a mammal, for example a human, diagnosed or suspected of having multiple sclerosis, can include administering a therapeutically effective dose of an anti-αβ TCR antibody or fragment thereof of the present invention to a mammalian subject diagnosed with, or suspected of having any one or more of: recent onset multiple sclerosis, benign multiple sclerosis, relapsing/remitting, multiple sclerosis, secondary/progressive multiple sclerosis, primary/progressive multiple sclerosis, and progressive/relapsing multiple sclerosis. In some embodiments, the method of treating a mammal with multiple sclerosis can further comprise administering a therapeutically effective dose of an anti-αβ TCR antibody or fragment thereof of the present invention in an escalating dose regimen, a diminishing dose regimen, or combinations thereof, as disclosed herein.

Clinically, agents including alemtuzumab and daclizumab are being tested in MS. However, these therapies have questionable efficacy and safety profiles. In animal studies, targeting the αβ T cell receptor has shown dramatic therapeutic efficacy on clinical and pathological signs of disease. It not only silences the autoreactive immune response, but also prevents epitope spreading to other myelin epitopes, inhibiting progression of disease. In some embodiments, the anti-αβ TCR antibody or fragment thereof of the present invention will decrease the average number of monthly contrast enhancing lesions by 50% or greater. In some embodiments anti-αβTCR antibody or fragment thereof of the present invention will decrease the mean number of contrast enhancing lesions (CEL) during months 3-6 after treatment with the anti-αβ TCR antibody or fragment thereof of the present invention, compared to the mean total of CELs during baseline MRIs (for example, the mean total of CELs during 3 MRIs taken during the two months prior to treatment). In other embodiments, treatment with anti-αβ TCR antibody Of fragment thereof of the present invention improves or prevents the worsening of Multiple Sclerosis symptoms as measured by the mean Scripps Neurological Rating Scale (SMS) compared to the SNRS, the Expanded Disability Status Scale (EDSS), and/or the Multiple Sclerosis Functional Composite (MSFC).

In some embodiments, the anti-αβ TCR antibody or fragment thereof of the present invention will reduce the number of myelin-specific T cells. In some embodiments, the anti-αβ TCR antibody or fragment thereof of the present invention will change the phenotype of myelin-specific T cells from a proinflammotry-TH1/17 to an anti-inflammatory T1-12-like T cell and/or render disease causing T cells non-responsive.

As used herein, recent-onset Multiple Sclerosis may include subjects having a first demyelenating event (clinically isolated syndrome (CID)). Methods for detecting and/or diagnosing recent-onset multiple sclerosis are well known in the neurological field. Some illustrative examples can include, magnetic resonance imaging, for lesion detection, such as the use of lesion volume and count of Gadolinium-enhancing and T2 lesions (i.e., lesions seen on T2-weighted images), T1-weighted hypointense lesions (Black Holes) and central nervous system (CNS) atrophy measures, are able to capture a more global picture of the range of tissue alterations caused by inflammation, demyelination, axonal loss, and neurodegeneration. In some embodiments, objective clinical evidence of one lesion (Clinically Isolated Syndrome) a recent-onset multiple sclerosis patient can be determined with dissemination in space demonstrated by: two or more MRI lesions consistent with multiple sclerosis plus a positive CSF and dissemination in time demonstrated by: MRI or a second clinical attack. Positive CSF is generally defined as oligoclonal bands different from those in serum or raised immunoglobulin G index. In an example, MRI criteria for brain abnormality as determined by space and time dissemination and MRI lesions disseminated in space can be determined if at least three of the following criteria are met: 1) One gadolinium-enhancing lesion or nine T2-hyperintense lesions in the brain or spine; 2) at least one infratentorial or spine lesion; 3) at least one juxtacortical lesion; or 4) at least three periventricular lesions. To determine the presence of MRI Lesions Disseminated in Time, at least one criterion must be met: 1) Gadolinium-enhancing lesion $\geq$3 months after initial presentation, but in a different location from the initial event, and 2) New T2 lesion, compared with a reference MRI done $\geq$30 days after onset of initial event. Adapted from Polman C H, Reingold S C, Edan G, et al: Diagnostic Criteria for Multiple Sclerosis: 2005 Revisions to the "McDonald Criteria." Ann Neurol 2005; 58:840-846, the disclosure of which in incorporated herein in its entirety.

Inflammatory and Fibrotic Lung Disease, including Eosinophilic Pneumonias; Idiopathic Pulmonary Fibrosis, and Hypersensitivity Pneumonitis may involve a disregulated immune-inflammatory response. Inhibition of that response would be of therapeutic benefit.

Autoimmune or Immune-mediated Skin Disease including Bullous Skin Diseases, Erythema Multiforme, and Contact Dermatitis are mediated by auto-antibodies, the genesis of which is T lymphocyte-dependent.

Psoriasis is a T lymphocyte-mediated inflammatory disease. Lesions contain infiltrates of T lymphocytes, macrophages and antigen processing cells, and some neutrophils.

Inflammatory diseases can include allergy type diseases, which include those that are IgE mediated and non-IgE mediated. For example, allergic rhinitis; atopic dermatitis; food hypersensitivity; and urticaria are T lymphocyte dependent. These diseases are predominantly mediated by T lymphocyte induced inflammation, IgE mediated-inflammation or a combination of both. In some embodiments, the anti-αβ TCR antibodies of the present invention can find utility in treating allergic disease, hypersensitive associated disease or respiratory disease associated with airway inflammation, such as asthma. In some embodiments, the compositions of the present invention are effective in preventing, treating or alleviating one or more symptoms related to anaphylaxis, skin allergy, eczema, allergic rhinitis, urticaria, atopic dermatitis, dry eye disease, allergic contact allergy, food hypersensitivity, allergic conjunctivitis, insect venom allergy, bronchial asthma, allergic asthma, intrinsic asthma, occupational asthma, atopic asthma, acute respiratory distress syndrome (ARDS) and chronic obstructive pulmonary disease (COPD).

Hypersensitivity associated diseases or disorders that may be treated by the methods of the invention include, but are not limited to, anaphylaxis, drug reactions, skin allergy, eczema, allergic rhinitis, urticaria, atopic dermatitis, dry eye disease (or otherwise referred to as Keratoconjunctivitis sicca (KCS), also called keratitis sicca, xerophthalmia, allergic contact allergy, food allergy, allergic conjunctivitis, insect venom allergy and respiratory diseases associated with airway inflammation, for example, mediated asthma and non-IgE mediated asthma.

The respiratory diseases associated with airway inflammation may include, but are not limited to rhinitis, allergic rhinitis, bronchial asthma, allergic (extrinsic) asthma, non-allergic (intrinsic) asthma, occupational asthma, atopic asthma, exercise induced asthma, cough-induced asthma, acute respiratory distress syndrome (ARDS) and chronic obstructive pulmonary disease (COPD).

Transplantation associated diseases, including Graft rejection and Graft-Versus-Host-Disease (GVHD) are T lymphocyte-dependent, inhibition of T lymphocyte function is ameliorative. The anti-αβ TCR antibodies and antibody fragments described above are useful for treating, preventing or delaying allograft rejection.

The present invention is not limited by the type of allograft employed. For example, in certain embodiments, the allograft is a solid organ or tissue selected from the group consisting of: Heart, Lung, Kidney, Liver, Pancreas, Intestine, Stomach, Testis, Hand, Cornea, Skin including Face replant, islets of Langerhans (Pancreas Islet Cells), Bone marrow/Adult stem cell, Blood transfusion/Blood Parts Transfusion, Blood vessels, Heart valve, Bone, and a cell or tissue transplant recipient (e.g., stem cell or bone marrow cell recipient).

Administration

The antibody is preferably administered to the mammal in a carrier; preferably a pharmaceutically-acceptable carrier. Suitable carriers and their formulations are described in Remington's Pharmaceutical Sciences, 16th ed., 1980, Mack Publishing Co., edited by Oslo et al. Typically, an appropriate amount of a pharmaceutically-acceptable salt is used in the formulation to render the formulation isotonic. Examples of the carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The anti-αβ TCR antibodies or antibody fragments thereof can be administered to the subject by injection (e.g., intravenous, intraperitoneal, subcutaneous, intramuscular, intraportal), or by other methods such as infusion that ensure its delivery to the bloodstream in an effective form. The antibody may also be administered by isolated perfusion techniques, such as isolated tissue perfusion, to exert local therapeutic effects. Local or intravenous injection is preferred.

Guidance in selecting appropriate doses for antibody is found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 0.01 mg/kg to up to 100 mg/kg of body weight or more per day, more preferably, from about 0.1 mg/kg to up to about 10 mg/kg, and even more preferably from about 0.2 mg/kg to about 0.7 mg/kg of body weight or more per day depending on the factors mentioned above.

In some embodiments, methods for treating an autoimmune disease, an inflammatory disease or a graft tissue rejection (for example, a renal transplantation rejection reaction) can include administering an anti-αβ TCR antibody or antibody fragment thereof or an anti-αβ TCR IgM antibody or antibody fragment thereof to a subject in need, in an amount from about 1 mg/day to about 200 mg/day, or from about 7 mg/day to about 58 mg/day or, from about 14 mg/day to about 45 mg/day, or from about 28 mg/day to about 42 mg/(or an amount of 7 mg/day, 14 mg/day, 21 mg/day, 28 mg/day, 30 mg/day, 32 mg/day, 34 mg/day, 35 mg/day, 36 mg/day, 38 mg/day, 40 mg/day, 42 mg/clay, 44 mg/day, 46 mg/day, 48 mg/day, 50 mg/stay, 52 mg/day, 54 mg/day, 56 mg/day or 58 mg/day or more, or combinations thereof. As used herein, the integers 1 to 200 encompasses or includes, any integer or fraction thereof between the integers 1 and 200. For example, a daily dose of from about 7 mg/day to about 58 mg/day would naturally include all integers between this range, for example: 8, 10, 13, 27, 28, 29, 30, 45, 53 and 57 mg/day, and any fractional amounts thereof, for example, 3.5, 4.7, 5.25, 11.6, 22.1, 46.3 and 51.125 mg/day as merely examples of fractional amounts as contemplated between the integers 7 and 58. In some embodiments, a 3, 4, 5, 6, 7, 8, 9, 10, 11, 12, 13, or 14 day dosing schedule, can include an escalating and/or a diminishing dosing schedule which contemplates sequential daily doses that may be the same and/or may be different. In certain embodiments of the methods, assays and compositions of the present invention, the anti-αβ TCR antibody or antibody fragment thereof comprises TOL101 antibody or antibody fragment thereof which binds to a αβ TCR. In certain embodiments of the methods of the present invention, the autoimmune disease, inflammation disease or graft tissue rejection is renal transplant tissue rejection/graft versus host disease or multiple sclerosis.

In some embodiments, the methods of the present invention, for example, methods for treating an autoimmune disease, an inflammatory disease or a graft tissue rejection can include administering an anti-αβ TCR antibody or antibody fragment thereof to a subject in need, in an amount ranging from about 1 mg/day to about 200 mg/day, or from about 7 mg to about 58 mg per daily dose, or a fractional unit dose that added together comprises a daily dose, for example a daily dose of 28 mg can comprise two 14 mg doses administered at different times within a 24 hour period, for example twice a day, or every 12 hours. In some embodiments, the dosing regimen can comprise dosing a patient or subject in need thereof, with a composition, for example, a pharmaceutical composition, with a daily dose that essentially does not vary between day to day. In some embodiments, the subject is treated with a titrated daily dose that begins at day 0 with the highest daily dose, for example, 58 mg per day, or 56 mg/day or 42 mg/day and is titrated to the lowest daily dose, for example, 7 mg per day, or 14 mg/day over a period of three to five to six days. Exemplary dosing schedules are shown below in Tables 1-4.

TABLE 1

Exemplary 3 day diminishing dosing schedule

| Day | Daily Dose 1 | Daily Dose 2 | Daily Dose 3 | Daily Dose 4 | Daily Dose 5 | Daily Dose 6 | Daily Dose 7 | Daily Dose 8 | Daily Dose 9 | Daily Dose 10 |
|---|---|---|---|---|---|---|---|---|---|---|
| 0 | 58 mg | 56 mg | 56 mg | 56 mg | 42 mg | 42 mg | 42 mg | 42 mg | 42 mg | 42 mg |
| 1 | 42 mg | 42 mg | 42 mg | 28 mg | 42 mg | 42 mg | 36 mg | 32 mg | 42 mg | 28 mg |
| 2 | 28 mg | 14 mg | 28 mg | 21 mg | 28 mg | 14 mg | 28 mg | 21 mg | 21 mg | 14 mg |

TABLE 2

Exemplary 3 day escalating dosing schedule

| Day | Daily Dose 1 | Daily Dose 2 | Daily Dose 3 | Daily Dose 4 | Daily Dose 5 | Daily Dose 6 | Daily Dose 7 | Daily Dose 8 | Daily Dose 9 | Daily Dose 10 |
|---|---|---|---|---|---|---|---|---|---|---|
| 0 | 7 mg | 7 mg | 7 mg | 14 mg | 14 mg | 14 mg | 21 mg | 28 mg | 14 mg | 14 mg |
| 1 | 14 mg | 14 mg | 21 mg | 28 mg | 28 mg | 42 mg | 42 mg | 42 mg | 42 mg | 28 mg |
| 2 | 28 mg | 21 mg | 28 mg | 42 mg | 32 mg | 42 mg | 42 mg | 42 mg | 52 mg | 58 mg |

TABLE 3

Exemplary 6 day diminishing dosing schedule

| Day | Daily Dose 1 | Daily Dose 2 | Daily Dose 3 | Daily Dose 4 | Daily Dose 5 | Daily Dose 6 | Daily Dose 7 | Daily Dose 8 | Daily Dose 9 | Daily Dose 10 |
|---|---|---|---|---|---|---|---|---|---|---|
| 0 | 58 mg | 56 mg | 56 mg | 42 mg | 42 mg | 42 mg | 42 mg | 42 mg | 42 mg | 42 mg |
| 1 | 42 mg | 42 mg | 42 mg | 28 mg | 42 mg | 42 mg | 36 mg | 32 mg | 42 mg | 28 mg |
| 2 | 28 mg | 42 mg | 28 mg | 21 mg | 42 mg | 42 mg | 28 mg | 21 mg | 21 mg | 21 mg |
| 3 | 21 mg | 28 mg | 21 mg | 14 mg | 28 mg | 28 mg | 21 mg | 21 mg | 21 mg | 14 mg |
| 4 | 14 mg | 21 mg | 14 mg | 14 mg | 14 mg | 14 mg | 21 mg | 14 mg | 14 mg | 7 mg |
| 5 | 14 mg | 14 mg | 7 mg | 14 mg | 14 mg | 7 mg | 14 mg | 14 mg | 7 mg | 7 mg |

TABLE 4

Exemplary 5 day diminishing dosing schedule

| Day | Daily Dose 1 | Daily Dose 2 | Daily Dose 3 | Daily Dose 4 | Daily Dose 5 | Daily Dose 6 | Daily Dose 7 | Daily Dose 8 | Daily Dose 9 | Daily Dose 10 |
|---|---|---|---|---|---|---|---|---|---|---|
| 0 | 58 mg | 56 mg | 56 mg | 56 mg | 56 mg | 42 mg | 42 mg | 42 mg | 42 mg | 42 mg |
| 1 | 42 mg | 42 mg | 42 mg | 28 mg | 28 mg | 42 mg | 28 mg | 42 mg | 42 mg | 28 mg |
| 2 | 28 mg | 28 mg | 28 mg | 21 mg | 21 mg | 42 mg | 28 mg | 21 mg | 42 mg | 21 mg |
| 3 | 21 mg | 28 mg | 28 mg | 14 mg | 14 mg | 28 mg | 21 mg | 21 mg | 28 mg | 14 mg |
| 4 | 14 mg | 21 mg | 14 mg | 14 mg | 7 mg | 14 mg | 14 mg | 14 mg | 14 mg | 7 mg |

In some embodiments, the dosing regimen may comprise an escalation dosing schedule, wherein on day 0, the daily dose is the lowest daily dose to be administered to the subject. On the last day or someday within the interval of treatment, the daily dose is escalated to the highest daily dose. In one embodiment, the subject is administered an anti-αβ TCR antibody or antibody fragment thereof until the subject's tacrolimus levels have reached a target level. In one embodiment, the subject is administered err anti-αβ TCR antibody or antibody fragment thereof daily for a minimum of 3 days or until the subject's tacrolimus levels have reached a target level. In one embodiment, the subject is administered an anti-αβ TCR antibody or antibody fragment thereof daily for a minimum of 4 days or until the subject's tacrolimus levels have reached a target level. In one embodiment, the subject is administered an anti-αβ TCR antibody or antibody fragment thereof daily for a minimum of 5 days or until the subject's tacrolimus levels have reached a target level. In one embodiment, the subject is administered an anti-αβ TCR antibody or antibody fragment thereof daily for a minimum of 6 days or until the subject's tacrolimus levels have reached a target level. In one embodiment, the subject is administered an anti-all TCR antibody or antibody fragment thereof daily for a maximum of 10 days. In some embodiments, the target level of tacrolimus is 8-15 ng/ml. In one embodiment, the escalation dosing regimen can comprise the following dosing schedules exemplified in Tables 5 and 6:

TABLE 5

Exemplary 6 day escalating dosing schedule

| Day | Daily Dose 1 | Daily Dose 2 | Daily Dose 3 | Daily Dose 4 | Daily Dose 5 | Daily Dose 6 | Daily Dose 7 | Daily Dose 8 | Daily Dose 9 | Daily Dose 10 |
|---|---|---|---|---|---|---|---|---|---|---|
| 0 | 7 mg  | 14 mg | 7 mg  | 14 mg | 7 mg  | 7 mg  | 7 mg  | 14 mg | 14 mg | 7 mg  |
| 1 | 14 mg | 21 mg | 14 mg | 21 mg | 14 mg | 14 mg | 14 mg | 21 mg | 21 mg | 14 mg |
| 2 | 21 mg | 28 mg | 32 mg | 28 mg | 28 mg | 28 mg | 21 mg | 28 mg | 28 mg | 21 mg |
| 3 | 28 mg | 42 mg | 48 mg | 42 mg | 42 mg | 42 mg | 28 mg | 28 mg | 42 mg | 28 mg |
| 4 | 36 mg | 52 mg | 58 mg | 56 mg | 56 mg | 54 mg | 42 mg | 32 mg | 42 mg | 42 mg |
| 5 | 58 mg | 58 mg | 58 mg | 56 mg | 56 mg | 54 mg | 54 mg | 42 mg | 42 mg | 42 mg |

TABLE 6

Exemplary 5 day escalating dosing schedule

| Day | Daily Dose 1 | Daily Dose 2 | Daily Dose 3 | Daily Dose 4 | Daily Dose 5 | Daily Dose 6 | Daily Dose 7 | Daily Dose 8 | Daily Dose 9 | Daily Dose 10 |
|---|---|---|---|---|---|---|---|---|---|---|
| 0 | 14 mg | 7 mg  | 14 mg | 7 mg  | 14 mg | 14 mg | 14 mg | 14 mg | 7 mg  | 7 mg  |
| 1 | 21 mg | 28 mg | 21 mg | 14 mg | 28 mg | 21 mg | 21 mg | 28 mg | 14 mg | 14 mg |
| 2 | 32 mg | 46 mg | 36 mg | 28 mg | 36 mg | 32 mg | 21 mg | 42 mg | 28 mg | 21 mg |
| 3 | 42 mg | 46 mg | 42 mg | 42 mg | 42 mg | 42 mg | 28 mg | 42 mg | 42 mg | 28 mg |
| 4 | 42 mg | 46 mg | 58 mg | 56 mg | 56 mg | 42 mg | 42 mg | 42 mg | 42 mg | 42 mg |

In some embodiments, the daily dose is the total daily dose, administered in one unit dose or multiple doses, for example, 2, 3 or 4 unit doses combined to arrive at the stated total daily dose.

In some embodiments, methods for treating an autoimmune disease, an inflammatory disease or a graft tissue rejection can include administering at least three separate doses of anti-αβ TCR antibodies (e.g., IgG or IgM), or anti-αβ TCR antibody fragments thereof, to a subject with an autoimmune disease, an inflammatory disease, an organ allograft transplant recipient, wherein the at least three separate doses are administered over three consecutive days, and wherein no two doses are administered on the same day. In other embodiments, the at least three separate doses comprises or consists of four separate doses, wherein the at least four separate doses are administered for four consecutive days, and wherein no two doses are administered on the same day. In particular embodiments, the at least three separate doses comprises or consists of five separate doses, wherein the at least five separate doses are administered for five consecutive days, and wherein no two doses are administered on the same day. In other embodiments, the at least three separate doses comprises or consists of six to fourteen separate doses, wherein the at least six to fourteen separate doses are administered for six to fourteen consecutive days, and wherein no two doses are administered on the same day.

In some embodiments, treating a subject with an autoimmune disease, an inflammatory disease or a graft tissue rejection can comprise administering at least a first dose of anti-αβ TCR antibodies (e.g., IgG or IgM), or anti-αβ TCR antibody fragments, to a subject, wherein the first dose is administered intravenously over at least 50 minutes or at least 70 minutes (e.g., 50-100 minutes; 70-200 minutes; 70-180 minutes; 70-140 minutes; or 70 . . . 140 . . . 180 . . . 200 minutes). In certain embodiments, the present invention provides methods of delaying or preventing allograft rejection comprising: administering at least a first dose of anti-αβ TCR antibodies (e.g., IgG or IgM), or anti-αβ TCR antibody fragments, to an allograft transplant recipient, wherein the first dose is administered intravenously at a rate of between 0.05 mg/minute and 0.35 mg/minute (e.g., 0.05 . . . 0.1 . . . 0.2 . . . 0.3 . . . 0.35 mg/minute).

In other embodiments, the at least a first dose comprises at least three separate doses, wherein the three separate doses are administered over three consecutive days, and wherein each of the three separate doses are administered intravenously over at least 50 minutes . . . 60 minutes . . . or at least 70 minutes. In further embodiments, the first dose is administered intravenously over at a substantially constant rate (e.g., a rate of between 0.05 mg/minute and 0.35 mg/minute). In certain embodiments, the first dose is administered in a high flow-rate vein.

The anti-αβ TCR antibodies and antibody fragments may be administered by any suitable means, including parenteral, non-parenteral, subcutaneous, topical, intraperitoneal, intrapulmonary, intranasal, and intralesional administration (e.g., for local immunosuppressive treatment). Parenteral infusions include, but are not limited to, intramuscular, intravenous, intra-arterial, intraperitoneal, or subcutaneous administration. In addition, anti-αβ TCR antibodies and antibody fragments may be administered by pulse infusion, particularly with declining doses.

The anti-αβ TCR antibodies and antibody fragments can be incorporated into pharmaceutical compositions suitable for administration to a subject. For example, the pharmaceutical composition may comprise anti-αβ TCR antibodies and antibody fragments and a pharmaceutically acceptable carrier. As used herein, "pharmaceutically acceptable carrier" includes solvents, dispersion media, coatings, antibacterial and antifungal agents, isotonic and absorption delaying agents, and the like that are physiologically compatible. Examples of pharmaceutically acceptable carriers include one or more of the following: water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the anti-αβ TCR antibodies and antibody fragments.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies.

Therapeutic compositions typically are sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody fragment) in the required amount in an appropriate solvent with one or a combination of ingredients enumerated above, as required, followed by sterile filtration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yield a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art (see, e.g., Sustained and Controlled Release Drug Delivery Systems. J. R. Robinson. ed., Marcel Dekker, Inc., New York, 1978).

The pharmaceutical compositions of the invention may include a "therapeutically effective amount" or a "prophylactically effective amount" of an antibody or antibody fragment of the invention. A "therapeutically effective amount" refers to an amount effective, at dosages and for periods of time necessary, to achieve the desired therapeutic result (e.g., prevent or reduce allograft rejection, treat, alleviate or prevent recurrence or occurrence of autoimmune and inflammatory symptoms and conditions). A therapeutically effective amount of the antibody or antibody fragment may vary according to factors such as the disease state, age, sex, and weight of the individual, and the ability of the antibody Of antibody fragment to elicit a desired response in the individual. A therapeutically effective amount is also one in which any toxic or detrimental effects of the anti-αβ TCR antibodies or antibody fragment are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

In certain embodiments, the present invention provides compositions comprising an isolated antibody comprising a polynucleotide sequence of SEQ ID NOs: 3, 4, and 5, and wherein the isolated antibody binds to αβ TCR. In certain embodiments, the present invention provides compositions comprising an antibody which binds to a αβ TCR and competitively inhibits binding of the monoclonal antibody T10B9.1A-31 to the αβ TCR for the treatment of autoimmune diseases and disorders, inflammatory diseases or disorders and transplant tissue rejection or GVHD as described herein.

In certain embodiments, the present invention provides compositions comprising: isolated humanized monoclonal antibodies or fragments thereof comprising: i) at least one of the three complementary determining regions (CDRs) from the light chain variable region from the TOL101 antibody, ii) at least one of the three complementary determining regions (CDRs) from the heavy chain variable region from the TOL101 antibody, and iii) the constant regions from a human antibody. In further embodiments, the isolated humanized monoclonal antibodies or fragments thereof comprise: i) at least one, or at least two, or all three, of the three complementary determining regions (CDRs) from the light chain variable region from the TOL101 antibody, and ii) at least one, or at least two, or all three, of the three complementary determining regions (CDRs) from the heavy chain variable region from the TOL101 antibody.

In some embodiments, the present invention provides compositions comprising: isolated humanized monoclonal antibodies or fragments thereof comprising: i) the three complementary determining regions (CDRs) from the light chain variable region from the TOL101 antibody, ii) the complementary determining regions (CDRs) from the heavy chain variable region from the TOL101 antibody, and iii) the constant regions from a human antibody. In further embodiments, the humanized monoclonal antibodies or fragments thereof, are lyphilized. In other embodiments, the compositions further comprise a physiologically tolerable buffer. In particular embodiments, the compositions further comprise or consist of at least one, two, or three of the following: i) sterile water; ii) L-arginine about 100 mM L-arginine or 10-900 mM); iii) citrate (e.g., about 5 mM citrate, or about 1-25 mM citrate); iv) mannitol (e.g., about 4% mannitol (w/v) or about 1 to 30% w/v mannitol); and v) TWEEN or other non-ionic detergent (e.g., about 0.01%, TWEEN 80, pH 7.0). In further embodiments, a humanized monoclonal TOL101 antibody or fragments thereof, is present in the composition at between 14 mg and 52 mg, preferably between 28 mg and 52 mg, or present in the composition at 28 mg, 30 mg, 32 mg, 34 mg, 35 mg, 36 mg, 38 mg, 40 mg, 42 mg, 44 mg, 46 mg, 48 mg, or 50 mg.

Other Uses of Anti-$\alpha\beta$ TCR Antibodies

The therapeutic effects of the anti-$\alpha\beta$ TCR antibodies of the invention can be examined in in vitro assays and using in vivo animal models. A variety of well-known animal models can be used to further understand the role of the anti-$\alpha\beta$ TCR antibodies identified herein in the development and pathogenesis of, for instance, immune related disease or cancer, and to test the efficacy of the candidate therapeutic agents. The in vivo nature of such models makes them particularly predictive of responses in human patients. Animal models of immune related diseases include both non-recombinant and recombinant (transgenic) animals Non-recombinant animal models include, for example, rodent, e.g., murine models. Such models can be generated by introducing cells into syngeneic mice using standard techniques, e.g. subcutaneous injection, tail vein injection, spleen implantation, intraperitoneal implantation, and implantation under the renal capsule.

Animal models, for example, graft-versus-host disease, are known. Graft-versus-host disease occurs when immunocompetent cells are transplanted into immunosuppressed or tolerant patients. The donor cells recognize and respond to host antigens. The response can vary from life threatening severe inflammation to mild cases of diarrhea and weight loss. Graft-versus-host disease models provide a means of assessing T-cell reactivity against MHC antigens and minor transplant antigens. A suitable procedure is described in detail in Current Protocols in Immunology, Unit 4.3; said procedure is incorporated herein by reference in its entirety.

An animal model for skin allograft rejection is a means of testing the ability of T-cells to mediate in vivo tissue destruction which is indicative of and a measure of their role in anti-viral and tumor immunity. The most common and accepted models use murine grafts. Repeated experiments have shown that skin allograft rejection is mediated by T-cells, helper T-cells and killer-effector T-cells, and not antibodies. (Auchincloss, H. Jr. and Sachs, D. H., Fundamental Immunology, 2nd ed. W. E. Paul ed., Raven Press, NY, 1989, 889-992). A suitable procedure is described in detail in Current Protocols in Immunology, Unit 4.4. Other transplant rejection models which can be used to test the compositions of the invention are the allogeneic heart transplant models described by Tanabe, M. et al., Transplantation, (1994) 58:23 and Tinubu, S. A. et al., J. Immunol., (1994) 4330-4338.

Animal models for delayed type hypersensitivity provides an assay of cell mediated immune function as well. Delayed type hypersensitivity reactions are a T-cell mediated in vivo immune response characterized by inflammation which does not reach a peak until after a period of time has elapsed after challenge with an antigen. These reactions also occur in tissue specific autoimmune diseases such as multiple sclerosis (MS) and experimental autoimmune encephalomyelitis (EAE, a model for MS). A suitable procedure is described in detail in Current Protocols in Immunology, unit 4.5.

An animal model for arthritis is collagen-induced arthritis. This model shares clinical, histological and immunological characteristics of human autoimmune rheumatoid arthritis and is an acceptable model for human autoimmune arthritis. Mouse and rat models are characterized by synovitis, erosion of cartilage and subchondral bone. The anti-$\alpha\beta$ TCR antibodies of the invention can be tested for activity against autoimmune arthritis using the protocols described in Current Protocols in Immunology, above, units 15.5. See also the model using a monoclonal antibody to CD18 and VLA-4 integrins described in Issekutz, A. C. et al., Immunology, (1996) 88:569.

A model of asthma has been described in which antigen-induced airway hyper-reactivity, pulmonary eosinophilia and inflammation are induced by sensitizing an animal with ovalbumin and then challenging the animal with the same protein delivered by aerosol. Several animal models (guinea pig, rat, non-human primate) show symptoms similar to atopic asthma in humans upon challenge with aerosol antigens. Murine models have many of the features of human asthma. Suitable procedures to test the compositions of the invention for activity and effectiveness in the treatment of asthma are described by Wolyniec, W. W. et al., Am. J. Respir. Cell Mol. Biol., (1998) 18:777 and the references cited therein.

Additionally, the anti-$\alpha\beta$ TCR antibodies of the invention can be tested on animal models for psoriasis-like diseases. The anti-$\alpha\beta$ TCR antibodies of the invention can be tested in the scid/scid mouse model described by Scion, M. P. et al., Nat. Med., (1997) 3:183, in which the mice demonstrate histopathologic skin lesions resembling psoriasis. Another suitable model is the human skin/scid mouse chimera prepared as described by Nickoloff, B, J. et al., Am. J. Path., (1995) 146:580.

Methods for Selectively Inhibiting a (TCR+) T-Cell Immune Response

In some embodiments, the present invention provides a method for inhibiting or selectively inhibiting a ($\alpha\beta$ TCR$^+$) T-cell immune response. As used herein, the term "selectively inhibiting" or "inhibiting" generally refers to inhibition of at least one activation pathway of the all TCR$^+$ T-cell after exposure of a $\alpha\beta$ TCR$^+$ T-cell to an anti-$\alpha\beta$ TCR antibody or antibody fragment thereof of the present invention. "Selectively inhibiting" or "inhibiting" may also refer to inhibition of downstream effects of T cell activation such as proliferation and cytokine production.

As described above, selective inhibition of a (TCR+) T-cell immune response involves reduction or suppression of signaling components in all TCR$^+$ T-cells, (for example, human CD4$^+$ T$_{helper\ or\ memory}$ cells or CD8$^+$ T$_{effector}$ cells), that may lead to reduced or complete cessation of proliferation and/or production of proinflammatory cytokines such as Tumor Necrosis Factor-alpha (TNF-$\alpha$); interferon-gamma (IFN-$\gamma$); or interleukins associated with STAT activation, for example, IL-2, IL-4, IL-5, IL-6, IL-9 and/or IL-13. In various treatment methods employed herein, administering a therapeutically effective amount of an anti-$\alpha\beta$ TCR antibody or antibody fragment thereof results in a decreased expression or release of proinflammatory cytokines from said TCR+ T-cell as when compared to the activation of the TCR+ T-cell exposed to a cognate antigen in the context of MHC and in the absence of the anti-$\alpha\beta$ TCR antibody or antibody fragment thereof. Furthermore, the selective inhibition results in an $\alpha\beta$ TCR+ T-cell that is not depleted, but merely loses the expression of CD3, (for example, at least 3 doses of anti-$\alpha\beta$ TCR antibodies, or anti-$\alpha\beta$ TCR antibody fragments, is sufficient to reduce the CD3+ count in the allograft transplant recipient to less than 25 cells per mm³), and continues to express CD2. Thus, the anti-αβ TCR antibodies or fragments thereof of the present invention suppress T cell activation, including proliferation and production of proinflammatory cytokines, without inducing cell depletion, unlike other anti-T cell antibodies, such as OKT3, which deplete T-cells from circulation and may lead to severely immuno-compromised subjects.

Assays

In some embodiments, the anti-αβ TCR antibodies and antibody fragments thereof can be used in a screening assay to identify therapeutic compounds that mimic anti-up TCR antibodies and bind to anti-αβ TCR and cause functional deactivation of the TCR.

In one embodiment, the method includes assay steps for identifying a therapeutic compound that suppresses, represses or inactivates/deactivates TCR+ T-cell activation. The method includes the step of: contacting a αβ T-cell receptor (all TCR) or fragment thereof with an anti-αβ TCR antibody or antibody fragment thereof under conditions operable to form a TCR-anti-αβ TCR complex. The assay can be performed in any assay reaction container, wells, in tubes, or on solid substrates, provided that the assay conditions are conducive for the formation of a TCR-anti-αβ TCR antibody complex. In some embodiments, the reagents are added in liquid form suspended in an appropriate buffer. The αβ T-cell receptor can be isolated or purified from human T-cells sorted with the aid of a flow cytometry cell sorter.

In general terms, the second step includes contacting the TCR-anti-αβ TCR complex with a candidate compound. A candidate compound can include, but is not limited to: nucleic acids, peptides, proteins, (including antibodies as described herein), sugars, polysaccharides, glycoproteins, lipids, and small organic molecules. A "candidate compound" is a compound that can be tested in a screening assay. In one embodiment, a candidate compound can include antibodies or antibody fragments thereof if the candidate compound binds to a αβ T-cell receptor specifically, as compared to the absence of the candidate compound or a negative control protein or antibody (for example, Bovine Serum Albumin, or anti-BSA antibodies), that candidate compound can be said to be a "lead compound" which may be validated using assays capable of demonstrating αβ T-cell receptor deactivation, including reduction or cessation of cytokine production of the identified compound, or can be used as potential or actual therapeutic or active agent that possesses αβ T-cell receptor deactivation activity suitable for the treatment of an autoimmune, inflammatory, or tissue rejection disease or condition, such as diabetes mellitus type I and autoimmune or inflammatory neurodegenerative diseases, for example, multiple sclerosis, Parkinson's disease, or amyotrophic lateral sclerosis. The term "small organic molecules" typically refers to molecules of a size comparable to those organic molecules generally used in pharmaceuticals. Small organic molecules generally excludes biological macromolecules (e.g., proteins, nucleic acids, etc.). Preferred small organic molecules range in size up to about 5,000 Da. more preferably up to 2,000 Da. and most preferably up to about 1,000 Da.

Conventionally, new chemical entities with useful properties are generated by identifying a candidate compound having some desirable property or activity, creating variants of the candidate compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In some embodiments, high throughput screening methods involve providing a library containing a large number of potential therapeutic compounds (candidate compounds). Such "combinatorial chemical libraries" are then screened in one or more assays, as described herein to identify those library members (particular chemical species or subclasses) that display a desired characteristic activity.

A combinatorial chemical library, or chemical library, is a collection of diverse chemical compounds generated by either chemical synthesis or biological synthesis by combining a number of chemical "building blocks" such as reagents. For example, a linear combinatorial chemical library such as a polypeptide (e.g., mutein) library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, systematic, combinatorial mixing of 100 interchangeable chemical building blocks results in the theoretical synthesis of 100 million tetrameric compounds or 10 billion pentameric compounds.

Preparation of combinatorial chemical libraries are well known to those of skill in the art, Such combinatorial chemical libraries include, but are not limited to, peptide libraries (see, e.g., U.S. Pat. No. 5,010,175. Peptide synthesis is by no means the only approach envisioned and intended for use with the present invention. Other chemistries for generating chemical diversity libraries can also be used. Such chemistries include, but are not limited to: peptoids (per Publication No WO 91/19735, 26 Dec. 1991), encoded peptides (PCT Publication WO 93/20242, 14 Oct. 1993), random bio-oligomers (PCT Publication WO 92/00091, 9 Jan. 1992), benzodiazepines (U.S. Pat. No. 5,288,514), diversomers such as hydantoins, benzodiazepines and dipeptides, vinylogous polypeptides, nonpeptidal peptidomimetics with Beta-D-Glucose scaffolding, analogous organic syntheses of small compound libraries, oligocarbamates, and/or peptidyl phosphonates. See, generally, nucleic acid libraries (see, e.g., Strategene, Corp.), peptide nucleic acid libraries (see, e.g., U.S. Pat. No. 5,539,083) antibody libraries (see, e.g., PCT/US96/10287), carbohydrate libraries (see, e.g., U.S. Pat. No. 5,593,853), and small organic molecule libraries (see, e.g., benzodiazepines, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholine compounds U.S. Pat. No. 5,506,337, benzodiazepines U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). A number of well-known robotic systems have also been developed for solution phase chemistries. These systems include, but are not limited to, automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist and the Venture™ platform, an ultra-high-throughput synthesizer that can run between 576 and 9,600 simultaneous reactions from start to finish (see Advanced ChemTech, Inc, Louisville, Ky., USA). Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd Moscow, RU, 3D Pharmaceuticals, Exton, Pa., Martek Biosciences, Columbia, Md., etc.).

In some embodiments, the third step of the assay method includes determining the ability of said candidate compound to modulate the binding of the anti-$\alpha\beta$ TCR antibody or antibody fragment thereof to said TCR or fragment thereof, and wherein the modulation of the binding of said anti-all TCR antibody or antibody fragment thereof to said TCR or fragment thereof and failure to activate a resting T-cell indicates that said candidate compound is a therapeutic compound. The determination of whether the candidate compound can modulate the binding of the anti-$\alpha\beta$ TCR antibody or antibody fragment thereof to the TCR or fragment thereof can be accomplished in many ways. Modulation of the binding between the anti-$\alpha\beta$ TCR antibody or antibody fragment thereof to the TCR or fragment thereof can be accomplished by a competitive binding assay. In such an assay, the TCR can be adhered to a solid substrate, for example, on the surface of a 96-well ELISA plate, Varying amounts of the anti-$\alpha\beta$ TCR antibody or antibody fragment thereof can be added to the well in a control sample. In a test sample, the equivalent conditions to the control reaction are performed with the exception that varying amounts of a candidate compound is added contemporaneously with or subsequent to the addition of the anti-$\alpha\beta$ TCR antibody or antibody fragment thereof. The test and control wells are then washed to remove unbound anti-$\alpha\beta$ TCR antibody or antibody fragment thereof. Then the amount of bound anti-$\alpha\beta$ TCR antibody or antibody fragment thereof can be measured and compared to the corresponding control sample. If the candidate compound competitively inhibits binding of the anti-$\alpha\beta$ TCR antibody or antibody fragment thereof to the TCR, the candidate compound is then further tested to determine whether the candidate compound can activate a resting $\alpha\beta$ T-cell in the presence of an anti-CD3 antibody. This can be done by contacting one or more $\alpha\beta$ TCR$^+$ T-cells; with anti-CD3 antibody operable to bind to CD3 on the one or more $\alpha\beta$ TCR$^+$ T-cells, or a superantigen; and adding a candidate compound that modulates the binding of an anti-$\alpha\beta$ TCR antibody or antibody fragment thereof to a $\alpha\beta$ TCR or fragment thereof; and compare the extent or rate of $\alpha\beta$ TCR$^+$ T-cell activation occurring in the presence or absence of the tested candidate compound. The candidate compound is a therapeutic compound if the candidate compound does not increase the extent or rate of $\alpha\beta$ TCR$^+$ T-cell activation in the presence of the anti-CD3 antibody compared to the extent or rate of $\alpha\beta$ TCR$^+$ T-cell activation that occurs in the absence of the candidate compound.

EXAMPLES

The following Examples are presented in order to provide certain exemplary embodiments of the present invention and are not intended to limit the scope thereof.

Example 1

Treatment and Evaluation of Humans Treated with TOL101 or Chimeric TOL101

TOL101 is produced by the hybridoma. TOL101 MCB and is a murine IgM monoclonal antibody (specifically, IgMκ) which binds to human $\alpha\beta$ TCR.

Exemplary TOL101 and TOL101 Chimeric Antibody Formulation

TOL101 and chimeric TOL101 can be made as a lyophilized product that is formulated for reconstitution in sterile water for injection (SWFI) followed by dilution in saline prior to IV administration. The vialed product can be reconstituted in 3 mL SWFI to provide a final formulation of 50-150 in M L-arginine (e.g., 50 mM . . . 75 mM . . . 100 mM . . . 125 mM . . . 150 mM), 1-10 mM citrate (e.g., 1.0 mM . . . 2.0 mM . . . 3.0 mM . . . 4.0 mM . . . 5.0 mM . . . 6.0 mM . . . 7.0 mM . . . 8.0 mM . . . 9.0 mM . . . 10 mM), 2-8% mannitol (w/v) (e.g., 2% . . . 3% . . . 4% . . . 5% . . . 6% . . . 7% . . . or 8%), 0.005-0.05% Tween 80, pH 7.0 (e.g., 0.005% . . . 0.01% . . . 0.02% . . . 0.03% . . . or 0.05%).

Preparation of TOL101 and Chimeric TOL101

TOL101 and chimeric TOL101 can be reconstituted and diluted for intravenous (IV) administration. TOL101/chimeric TOL101 vials (e.g., with 14 mg of lyophilized antibody) can be sealed under vacuum. TOL101 and chimeric TOL101 can be reconstituted according to the following steps:

1. Calculate the number of vials needed (e.g., 1 vial for a 0.28 mg, 1.4 mg, 7 mg or a 14 mg dose, 2 vials for a 28 mg dose, et cetera);
2. Allow each vial to reach room temperature before reconstitution;
3. Aseptically remove caps, exposing rubber stoppers;
4. Clean stoppers with germicidal or alcohol swabs;
5. Insert a hypodermic needle into the vial to relieve internal pressure of the vial;
6. Aseptically reconstitute each vial with 3 mL SWFI using a second needle, then remove both needles;
7, Gently roll vial in hands at a 45 degree angle for 60 seconds. Ensure that the top of the vial is not in contact with material. Preferably, do not shake or invert the vial during reconstitution. Avoid foaming the material.
8. Allow vial to sit undisturbed for 3 minutes until any bubbles are eliminated; and
9. Gently roll vial in hands a second time for 60 seconds, or until contents are homogeneous.

Reconstituted solution should be inspected for particulate matter. If particulate matter does not disappear entirely, the vial should be segregated and not used. Reconstituted TOL101 or chimeric TOL101 can be diluted to 50 mL per vial with normal saline (NS) (see Table 7 below) into an IV infusion bag (Polyvinyl chloride, PVC bag). If a partial vial is to be used (i.e., 0.28 mg, 1.4 mg, or 7 mg), the entire vial should be reconstituted with 3 mL SWFI as described above, and the appropriate volume (i.e., 0.06 mL (60 µl). 0.3 mL, or 1.5 mL respectively) of the reconstituted TOL101/chimeric TOL101 should be transferred to the IV infusion bag. The IV bag should be inverted gently to mix the solution prior to infusion via a calibrated infusion pump.

Exemplary Rate of Infusion

The particular dose of TOL101 or chimeric TOL101 can be administered by slow intravenous infusion at a constant rate of 0.004 mg/min for 0.28 mg doses, 0.02 mg/min for 1.4 mg doses, 0.1 mg/min for 7 and 14 mg doses and, 0.2 mg/min for 28 mg doses, and 0.3 mg/min for doses of 42 mg or higher (see Table 7 below). Therefore, in this Example, TOL101 or chimeric TOL101 will not be administered over less than 70 minutes at any dose. If any intermediate doses are tested, the slower of the rates can be used (e.g., if an a rate of 0.2 mg/min was used for 28 mg doses and a rate of 0.3 mg/min was used for a dose of 42 mg and an intermediate dose is to be tested, then a dose of 35 mg can be administered at a rate of 0.2 mg/min). TOL101 or chimeric TOL101 is preferably administered into a high-flow vein. The IV line should be flushed slowly with approximately 25 mL of NS at the end of infusion.

TABLE 7

Rate and Total Duration of Infusion of TOL101 and Chimeric TOL101 at Each Dose Level

| Dose (mg) | # vials to reconstitute with SWFI (3 ml/vial) | Volume of reconstituted TOL101 to transfer to IV bag | Total dilution (mL) | Rate of infusion (mg/min) | Duration of infusion (min) |
|---|---|---|---|---|---|
| 0.28 | 1 | 0.06 mL | 50 | 0.004 | 70 |
| 1.4 | 1 | 0.3 mL | 50 | 0.02 | 70 |
| 7 | 1 | 1.5 mL | 50 | 0.1 | 70 |
| 14 | 1 | 3 mL | 50 | 0.1 | 140 |
| 28 | 2 | 6 mL | 100 | 0.2 | 140 |
| 42 | 3 | 9 mL | 150 | 0.3 | 140 |
| 56 | 4 | 12 mL | 200 | 0.3 | 180 |

Example 2

Treatment of Human Transplant Patients

This example describes the treatment of human kidney transplant patients with TOL101 monoclonal antibody, and testing these patients for CD3 count at various time points. The depletion and/or modulation of T cells (as determined by the CD3 biomarker) is important at the initial stages of organ transplantation as it prevents acute rejection. In addition, it also allows for the delayed application of maintenance immune suppression agents, which are known to be toxic to transplanted organs, especially in the case of kidney transplants. It has been determined through the experience of doctors that 50 (CD3+ counts/mm$^3$) represents an upper threshold that T cells need to be lowered to provide the best long term outcome. In this example, the kidney transplant patients were infused over the course of at least 6 days according the schedule in Table 8 below. Three different cohorts were tested with two patients in each cohort. The dosages tested were 0.28 mg, 1.4 mg, 7.0 mg of TOL101 antibody. The doses were given intravenously over 70 minutes. Each patient was given one dose each day over a total of 5 days, with the first dose being at the time of transplant surgery. The first dose was given in the operating room beginning after the subject was anesthetized and before unclamping (reperfusion of the allograft).

Diphenhydramine (50 mg IV) was administered prior to the first two doses of TOL101 and intravenous steroids were administered prior to the first three doses of TOL101. Subsequent doses of TOL101 were infused after oral steroid administration. Tacrolimus was also administered starting within the first 6 days post-transplant and for the duration of the study. Tacrolimus was administered at doses designed to reach and maintain a therapeutic range of 8-15 ng/mL for the first month post-transplant, and to maintain a therapeutic range of 6-12 ng/mL thereafter. Mycophenolate mofetil was administered the day of, or the day following, transplant and for the duration of the study at a maximum dose of 1000 mg BID.

TABLE 8

CD3 counts in kidney transplant patients treated with TOL101

| Subject ID | Study Drug | Dose (mg) | Time Point | CD3 Count |
|---|---|---|---|---|
| 1 | TOL101 | 0.28 | Baseline | 434.59 |
| 1 | TOL101 | 0.28 | Day 0 - End of Infusion | 24.62 |
| 1 | TOL101 | 0.28 | Day 0 - 2 Hrs Post Infusion | 64.14 |
| 1 | TOL101 | 0.28 | Day 0 - 4 Hrs Post Infusion | 57.77 |
| 1 | TOL101 | 0.28 | Day 0 - 8 Hrs Post Infusion | 112.09 |
| 1 | TOL101 | 0.28 | Day 1 Prior to Infusion | 121.81 |
| 1 | TOL101 | 0.28 | Day 2 Prior to Infusion | 125.74 |
| 1 | TOL101 | 0.28 | Day 3 Prior to Infusion | 151.04 |
| 1 | TOL101 | 0.28 | Day 4 - Prior to Infusion | 347.68 |
| 1 | TOL101 | 0.28 | Day 4 - End of Infusion | 16.20 |
| 1 | TOL101 | 0.28 | Day 4 - 2 Hrs Post Infusion | 16.58 |
| 1 | TOL101 | 0.28 | Day 4- 4 Hrs Post Infusion | 42.70 |
| 1 | TOL101 | 0.28 | Day 4 - 6-8 Hrs Post Infusion | 67.30 |
| 1 | TOL101 | 0.28 | Day 5 - Prior to Infusion | 147.66 |
| 1 | TOL101 | 0.28 | Last Dose F/U | 869.97 |
| 1 | TOL101 | 0.28 | Day 14 | 555.56 |
| 2 | TOL101 | 0.28 | Baseline | 529.18 |
| 2 | TOL101 | 0.28 | Day 0 - End of Infusion | 23.54 |
| 2 | TOL101 | 0.28 | Day 0 - 2 Hrs Post Infusion | 70.58 |
| 2 | TOL101 | 0.28 | Day 0 - 4 Hrs Post Infusion | 120.88 |
| 2 | TOL101 | 0.28 | Day 0 - 8 Hrs Post Infusion | 114.62 |
| 2 | TOL101 | 0.28 | Day 1 Prior to Infusion | 130.00 |
| 2 | TOL101 | 0.28 | Day 2 Prior to Infusion | 236.55 |
| 2 | TOL101 | 0.28 | Day 3 Prior to Infusion | 275.43 |
| 2 | TOL101 | 0.28 | Day 4 - Prior to Infusion | 191.32 |
| 2 | TOL101 | 0.28 | Day 5 - Prior to Infusion | 88.00 |
| 2 | TOL101 | 0.28 | Day 5 - End of Infusion | 18.97 |
| 2 | TOL101 | 0.28 | Day 5 - 2 Hrs Post Infusion | 33.96 |
| 2 | TOL101 | 0.28 | Day 5 - 4 Hrs Post Infusion | 77.40 |
| 2 | TOL101 | 0.28 | Day 5 - 6-8 Hrs Post Infusion | 84.48 |
| 2 | TOL101 | 0.28 | Last Dose F/U | 209.75 |
| 2 | TOL101 | 0.28 | Day 14 | 411.87 |
| 3 | TOL101 | 1.4 | Baseline | 158.34 |
| 3 | TOL101 | 1.4 | Day 0 - End of Infusion | (Hemolyzed) |
| 3 | TOL101 | 1.4 | Day 0 - 2 Hrs Post Infusion | (Hemolyzed) |
| 3 | TOL101 | 1.4 | Day 0 - 4 Hrs Post Infusion | (Hemolyzed) |
| 3 | TOL101 | 1.4 | Day 0 - 8 Hrs Post Infusion | 20.67 |
| 3 | TOL101 | 1.4 | Day 1 Prior to Infusion | 47.56 |
| 3 | TOL101 | 1.4 | Day 2 Prior to Infusion | (Hemolyzed) |
| 3 | TOL101 | 1.4 | Day 3 Prior to Infusion | (Hemolyzed) |
| 3 | TOL101 | 1.4 | Day 4 - Prior to Infusion | 506.12 |
| 3 | TOL101 | 1.4 | Day 4 - End of Infusion | 138.45 |
| 3 | TOL101 | 1.4 | Day 4 - 2 Hrs Post Infusion | (Hemolyzed) |
| 3 | TOL101 | 1.4 | Day 4- 4 Hrs Post Infusion | 148.84 |
| 3 | TOL101 | 1.4 | Day 4 - 6-8 Hrs Post Infusion | 212.37 |
| 3 | TOL101 | 1.4 | Day 5 - Prior to Infusion | 439.18 |
| 3 | TOL101 | 1.4 | Day 6 - Prior to Infusion | (Hemolyzed) |
| 3 | TOL101 | 1.4 | Last Dose F/U | 306.92 |
| 3 | TOL101 | 1.4 | Day 14 | 106.46 |
| 4 | TOL101 | 1.4 | Baseline | 315.92 |
| 4 | TOL101 | 1.4 | Day 0 - End of Infusion | 11.30 |
| 4 | TOL101 | 1.4 | Day 0 - 2 Hrs Post Infusion | 4.24 |
| 4 | TOL101 | 1.4 | Day 0 - 4 Hrs Post Infusion | 1.75 |
| 4 | TOL101 | 1.4 | Day 0 - 8 Hrs Post Infusion | 9.33 |
| 4 | TOL101 | 1.4 | Day 1 Prior to Infusion | 176.71 |
| 4 | TOL101 | 1.4 | Day 2 Prior to Infusion | 255.70 |
| 4 | TOL101 | 1.4 | Day 3 Prior to Infusion | 438.36 |
| 4 | TOL101 | 1.4 | Day 4 - Prior to Infusion | 454.13 |
| 4 | TOL101 | 1.4 | Day 5 - Prior to Infusion | 531.29 |
| 4 | TOL101 | 1.4 | Day 5 - End of Infusion | 13.91 |
| 4 | TOL101 | 1.4 | Day 5 - 2 Hrs Post Infusion | 30.86 |
| 4 | TOL101 | 1.4 | Day 5- 4 Hrs Post Infusion | 45.49 |
| 4 | TOL101 | 1.4 | Day 5 - 6-8 Hrs Post Infusion | 66.77 |
| 4 | TOL101 | 1.4 | Last Dose F/U | 206.52 |
| 4 | TOL101 | 1.4 | Day 14 | 353.77 |
| 5 | TOL101 | 7 | Baseline | 381.40 |
| 5 | TOL101 | 7 | Day 0 - End of Infusion | 2.25 |
| 5 | TOL101 | 7 | Day 0 - 2 Hrs Post Infusion | 2.84 |
| 5 | TOL101 | 7 | Day 0 - 4 Hrs Post Infusion | 1.12 |
| 5 | TOL101 | 7 | Day 0 - 8 Hrs Post Infusion | 5.83 |
| 5 | TOL101 | 7 | Day 1 Prior to Infusion | 30.92 |
| 5 | TOL101 | 7 | Day 2 Prior to Infusion | 72.43 |
| 5 | TOL101 | 7 | Day 3 Prior to Infusion | ND |
| 5 | TOL101 | 7 | Day 4 - Prior to Infusion | 383.69 |
| 5 | TOL101 | 7 | Day 4 - End of Infusion | 252.40 |

TABLE 8-continued

CD3 counts in kidney transplant patients treated with TOL101

| Subject ID | Study Drug | Dose (mg) | Time Point | CD3 Count |
|---|---|---|---|---|
| 5 | TOL101 | 7 | Day 4 - 2 Hrs Post Infusion | 261.86 |
| 5 | TOL101 | 7 | Day 4- 4 Hrs Post Infusion | 122.00 |
| 5 | TOL101 | 7 | Day 4 - 6-8 Hrs Post Infusion | 131.71 |
| 5 | TOL101 | 7 | Day 5 - Prior to Infusion | 451.23 |
| 5 | TOL101 | 7 | Day 6 - Prior to Infusion | 238.85 |
| 5 | TOL101 | 7 | Day 7 - Prior to Infusion | 147.38 |
| 5 | TOL101 | 7 | Last Dose F/U | (Hemolyzed) |
| 5 | TOL101 | 7 | Day 14 | 220.22 |
| 6 | TOL101 | 7 | Baseline | (Hemolyzed) |
| 6 | TOL101 | 7 | Day 0 - End of Infusion | (Hemolyzed) |
| 6 | TOL101 | 7 | Day 0 - 2 Hrs Post Infusion | (Hemolyzed) |
| 6 | TOL101 | 7 | Day 0 - 4 Hrs Post Infusion | 0.39 |
| 6 | TOL101 | 7 | Day 0 - 8 Hrs Post Infusion | 1.46 |
| 6 | TOL101 | 7 | Day 1 Prior to Infusion | 6.72 |
| 6 | TOL101 | 7 | Day 2 Prior to Infusion | 12.76 |
| 6 | TOL101 | 7 | Day 3 Prior to Infusion | 26.17 |
| 6 | TOL101 | 7 | Day 4 - Prior to Infusion | 13.50 |
| 6 | TOL101 | 7 | Day 4 - End of Infusion | 1.55 |
| 6 | TOL101 | 7 | Day 4 - 2 Hrs Post Infusion | 2.23 |
| 6 | TOL101 | 7 | Day 4- 4 Hrs Post Infusion | 4.18 |
| 6 | TOL101 | 7 | Day 4 - 6-8 Hrs Post Infusion | 3.97 |
| 6 | TOL101 | 7 | Day 5 - Prior to Infusion | 14.87 |
| 6 | TOL101 | 7 | Last Dose F/U | 52.19 |
| 6 | TOL101 | 7 | Day 14 | 209.33 |

The results of the study showed that the administration of TOL101 reduces CD3+ T cell counts in kidney transplant patients in a dose-dependent manner.

Example 3

TOL101 Selectively Inhibits T-Cells

Figure 1:
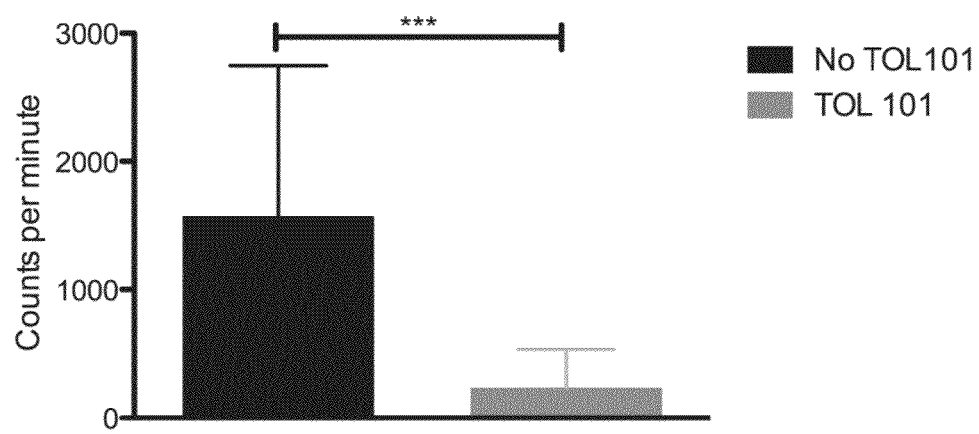
FIG. 1 depicts a bar graph illustrating that TOL101 suppresses proliferation in one-way mixed lymphocyte reaction (MLR).

To determine whether the anti-αβ TCR antibody TOL101 suppresses proliferation of T-cells in vitro, an experiment was performed to determine proliferation effects of TOL101 in a one-way MRL reaction. PBMCs were isolated from buffy coats of three healthy donors. Buffy coats were layered over a Ficol gradient to enrich for lymphocytes. Stimulator cells were then irradiated at 3000 rads. Stimulator and responder cells were co-cultured for 6 days at a ratio of 2:1 ((4×10$^5$) stimulator cells to 2×10$^5$ responder cells). Combinations for cells were as follows: a unit of blood from subject No. 1+a unit of irradiated blood from subject No. 2, a unit of blood from subject No. 1+a unit of irradiated blood from subject No. 3, a unit of blood from subject No. 2+a unit of irradiated blood from subject No. 1+a unit of blood from subject No. 2+a unit of irradiated blood from subject No. 3, a unit of blood from subject No. 3+a unit of irradiated blood from subject No. 1, a unit of blood from subject No. 3+a unit of irradiated blood from subject No. 2, TOL101 was added at time of culture at concentration of 9 μg/mL. Tritiated thymidine H$^3$ was added 5 days into culture and plates were harvested and counted on day 6. FIG. 1 shows representative data of 2 independent experiments, ***=p>0.001. As shown in FIG. 1, TOL101 significantly suppresses proliferation of T cells, directly indicating inhibition of the allo-immune response, when compared to the control.

Figure 2:
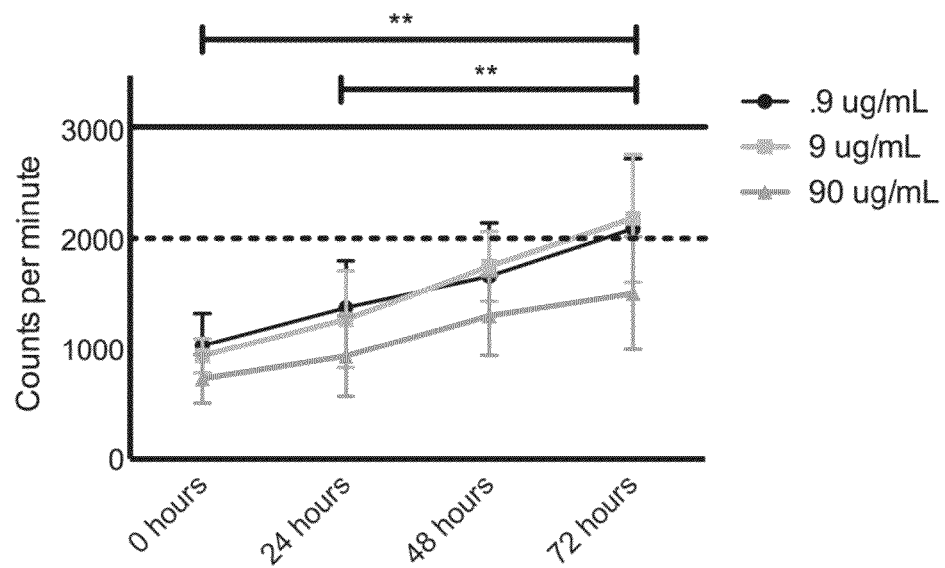
FIG. 2 depicts a line graph of a time course of T-cell proliferation in a one way MLR in the presence of TOL101 at varying concentrations.

In another experiment, TOL101 was shown to be particularly effective during the first 24 hours of the in vitro MLR reaction. PBMCs were isolated from huffy coats of three healthy donors, Buffy coats were layered over a Ficol gradient to enrich for lymphocytes. Stimulator cells were then irradiated at 3000 rads. Stimulator and responder cells were co-cultured for 6 days at a ratio of 2:1 (4×10$^5$ stimulator cells to 2×10$^5$ responder cells). Combinations for cells were as follows: a unit of blood from subject No. 1+unit of irradiated blood from subject No. 2, a unit of blood from subject No. 1+a unit of irradiated blood from subject No. 3, a unit of blood from subject No. 2+a unit of irradiated blood from subject No. 1, a unit of blood from subject No. 2+a unit of irradiated blood from subject No. 3, a unit of blood from subject No. 3+a unit of irradiated blood from subject No. 1, a unit of blood from subject No. 3+a unit of irradiated blood from subject No. 2. TOL101 was added at times 0 hours, 24 hours, 48 hours, and 72 hours. Concentrations of TOL101 added were 0.9 μg/mL, 9 μg/mL and 90 μg/mL. Tritiated thymidine H$^3$ was added 5 days into culture and plates were harvested and counted on day 6. As illustrated in FIG. 2, the solid line represents positive control proliferation of cultures with a CD3 antibody (OKT3) added at 9 μg/mL. Dashed line represents proliferation from cultures with no addition of TOL101. **=p>0.05. As can be seen from FIG. 2, the suppression of proliferation was observed to be greatest between the period of time of 0 hours to 24 hours.

Figure 3:
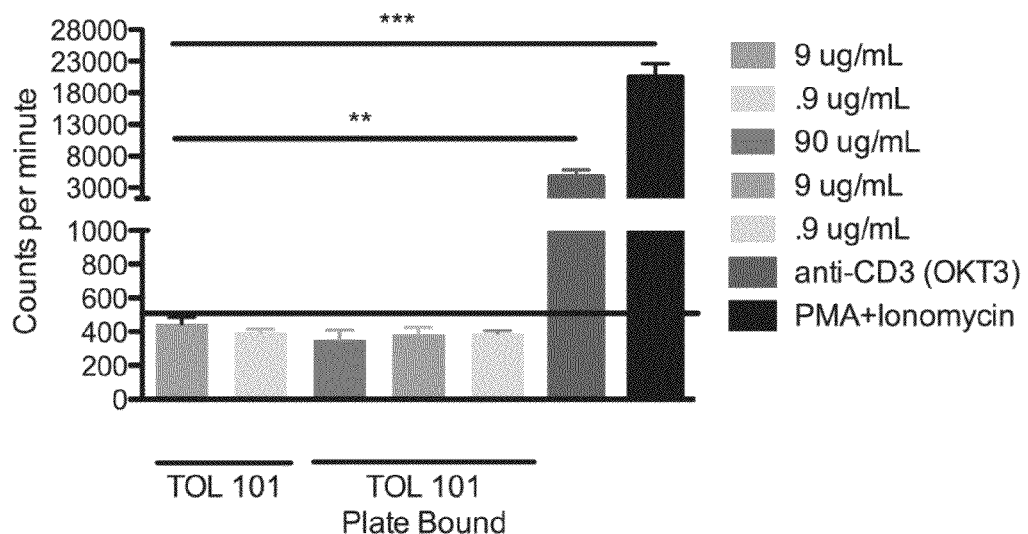
FIG. 3 depicts a bar graph of T-cell proliferation in the presence of TOL101 in a free form versus cross-linked at varying concentrations.

In another experiment, TOL101 was added to a liquid solution or plated onto a surface to measure the effect of cross-linking of TOL101 on T-cell proliferation compared to a control activation antibody anti-CD3 (OKT3). PBMCs were isolated from buffy coats of three healthy donors. Buffy coats were layered over a Ficol gradient to enrich for lymphocytes. Lymphoctyes were cultured at a density of 2×10$^5$ cells/well. Cells were cultured with either soluble TOL101 (9.9 μg/mL) or plate bound TOL101 (90, 9.9 μg/mL), while other cells were cultured with a CD3 antibody (OKT3 9 μg/mL) or PMA/ionomycin as positive controls. Tritiated thymidine H$^3$ was added 5 days into culture and plates were harvested and counted on day 6. As shown in FIG. 3, the solid line represents background proliferation, =p>0.05, *=p>0.001. Unlike anti-CD3, T10B9, and other anti-TCR antibodies (Brown et al. Clinical Transplantation 10; 607-613 [1996]), cross-linking of TOL101, even at the highest concentration of 90 μg/mL, does not cause it to become mitogenic (i.e. induce proliferation of T cells). This is a surprising and clinically relevant as it reflects the potential for safe utilization of TOL101 in clinical subjects.

Figure 4:
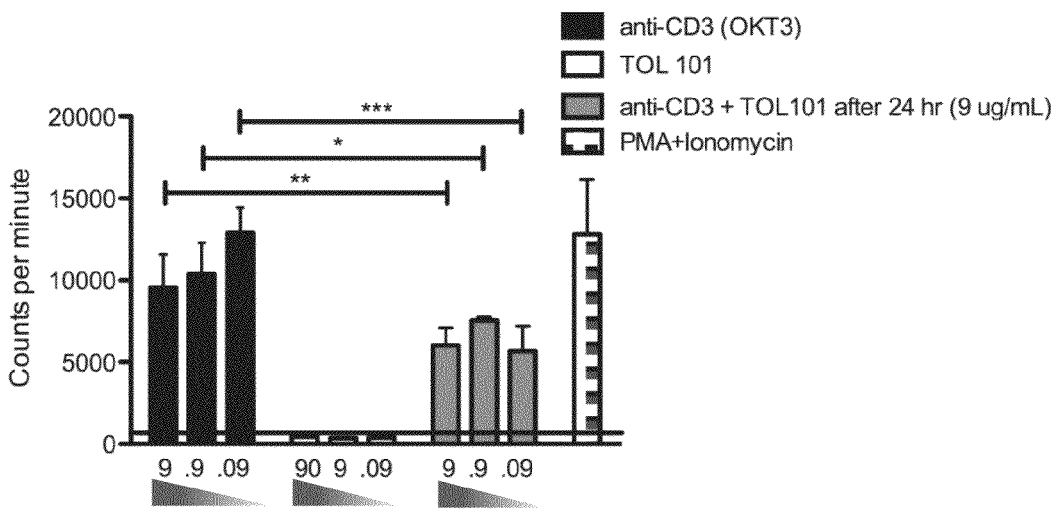
FIG. 4 depicts a bar graph depicting TOL101 mediated suppression of anti-CD3 mediated T-cell proliferation.

In another experiment, the suppressive activity of TOL101 against T cells stimulated with anti-CD3 was determined. The recognition mechanism(s) of the T cell receptor (TCR) are the α and β chains, which engage the complex of peptide and MHC. The genetic and cellular mechanisms involved result in the creation of millions of different α and β chains, providing broad pathogen coverage. The non-polymorphic components of the TCR, namely, CD3, γ, δ, and ε, and the TCR ζ chain dimer, interact with the α and β chain recognition components. There are no known intra-cellular signaling components to the α and β chains of the TCR. Rather it is believed that CD3 contains the signaling machinery use by the TCR to activate T cells. For example, the CD3 molecules are integral TCR components, not only required for appropriate TCR expression, but also contain a unique motif the ITAM (immunoreceptor-based tyrosine activation motif) in their intracellular/cytosolic components of these non-polymorphic molecules. These ITAMS, contained within the CD3, are the signaling machinery used by the TCR to activate T cells. The process through which activation of the αβ TCR results in CD3 mediated signaling is unknown. However, it was previously believed that an αβ TCR signal must occur through CD3. As such, the use of anti-CD3 antibodies circumvents the need for a αβ TCR activating signal. In this example PBMCs were isolated from huffy coats of three healthy donors. Buffy coats were layered over a Ficol gradient to enrich for lymphocytes. Lymphoctyes were cultured at a density of 2e5 cells/well. Cells were cultured with soluble TOL101 (9, 0.9 μg/mL), or with anti-CD3 (OKT3 9, 0.9, 0.09 μg/mL) or PMA/ionomycin as positive controls. At 24 hours, TOL101 (9 μg/mL) was added to one set of the OKT3 stimulated cells. Tritiated thymidine $H^3$ was added 5 days into culture and plates were harvested and counted on day 6. As shown in FIG. 4, surprisingly, TOL101 not only does not induce proliferation, but also ameliorates or reverses anti-CD3 induced proliferation of T-cells in vitro. *=p>0.01, =p>0.05, *=p>0.001.

Figure 5:
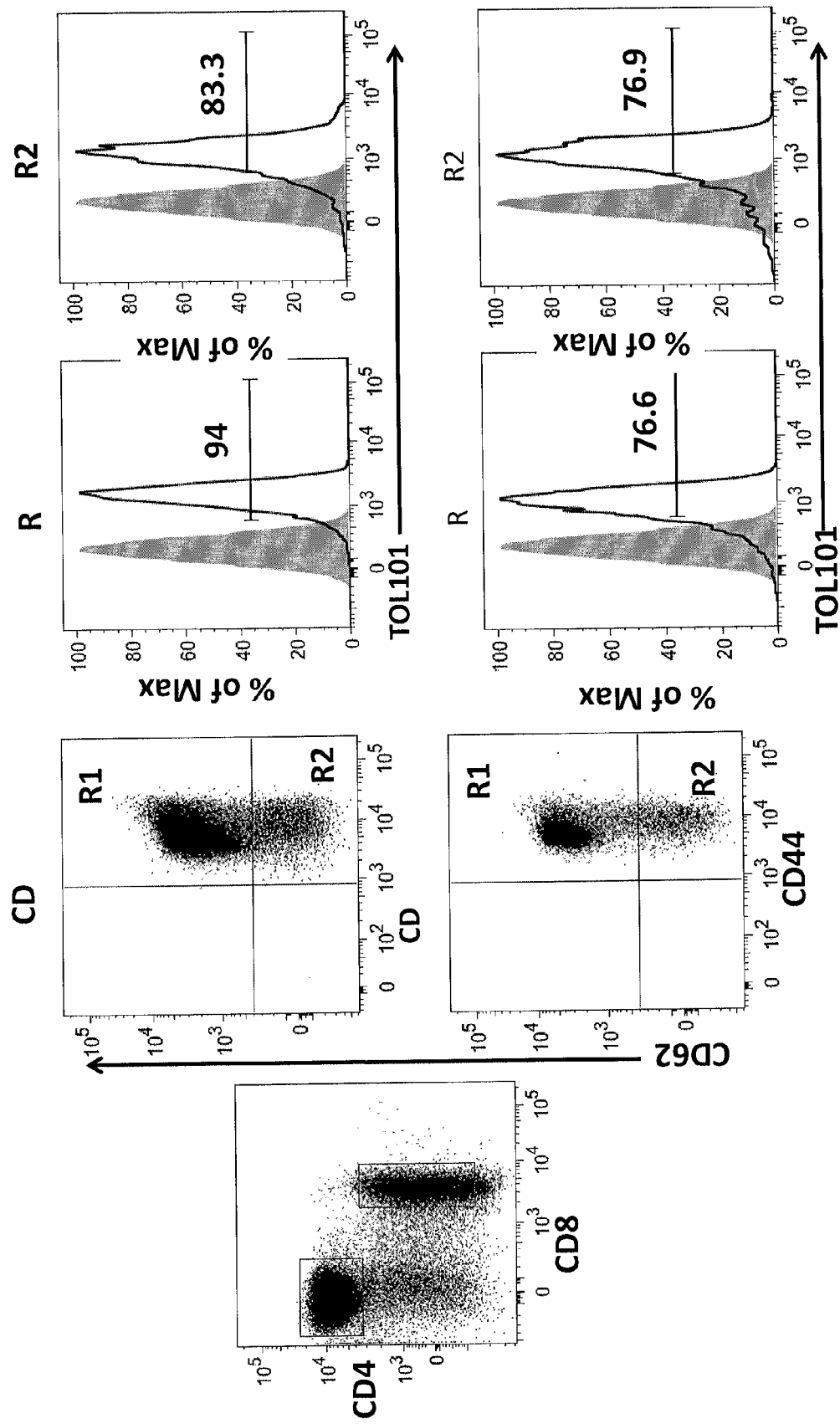
FIG. 5 depicts flow-cytometry pictograms illustrating the specificity of TOL101 to αβ TCR+ T-cells with an activated and naive phenotype.

In another experiment, the specificity of binding of TOL101 was measured in a population of mixed lymphocytes, PBMCs were isolated from huffy coats of three healthy donors. Buffy coats were layered over a Ficol gradient to enrich for lymphocytes. Cells were blocked for 30 minutes at 4° C. with human AB serum. Cells were then stained with following antibodies for 30 minutes at 4° C.: TOL101+anti mouse IgM, CD3, CD4, CD8, CD2, CD69 and CD44. Cells were washed and run on a BD FACS Canto II. Data analyzed by Flow Jo. Data as shown in FIG. 5 is representative of 6 patients. As shown in FIG. 5, the staining profile not only shows the specificity of TOL101 to T cells, but also illustrates that TOL101 binds to T cells irrespective of their activation state (e.g., binding to CD62L high and low expressors, indicative of activated and naive T cells, respectively).

Figure 6:
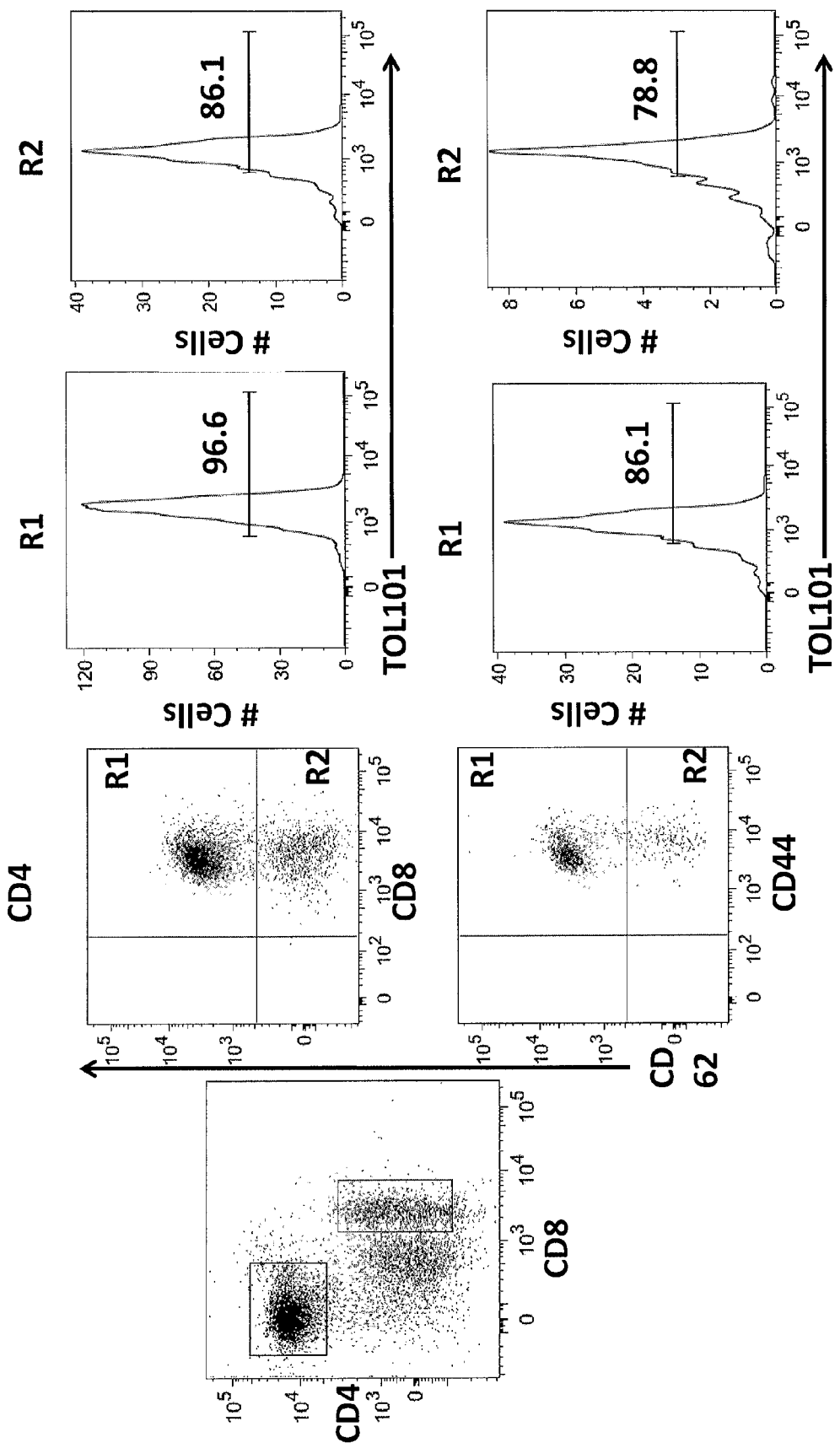
FIG. 6 depicts flow-cytometry pictograms illustrating the specificity of TOL101 to activated αβ TCP T-cells subsets in a one-way mixed lymphocyte reaction.

In another experiment, TOL101 was shown to bind to activated T cells, as shown in FIG. 6. Briefly, PBMCs were isolated from buffy coats of three healthy donors. Buffy coats were layered over a Ficol gradient to enrich for lymphocytes. Stimulator cells were then irradiated at 3000 rads. Stimulator and responder cells were co-cultured for 6 days at a ratio of 2:1 ($4\times10^5$ stimulator cells to $2\times10^5$ responder cells). Combinations for cells were as follows: a unit of blood from subject No. 1+a unit of irradiated blood from subject No. 2; a unit of blood from subject No. 1+a unit of irradiated blood from subject No. 3; a unit of blood from subject No. 2+a unit of irradiated blood from subject No. 1; a unit of blood from subject No. 2+a unit of irradiated blood from subject No. 3; a unit of blood from subject No. 3+a unit of irradiated blood from subject No. 1; and a unit of blood from subject No. 3+a unit of irradiated blood from subject No. 2. Cells were analyzed on day 6 of culture. Cells were blocked for 30 minutes at 4° C. with human AB serum, then stained with the following antibodies for 30 minutes at 4° C.: TOL101+anti mouse IgM, CD3, CD4, CD8, CD2, CD69 and CD44. Cells were washed and run on a BD FACS Canto II. Data were analyzed by Flow Jo. The results of the study further confirm TOL101's specificity for T Surprisingly, TOL101 bound to activated T cells, despite the fact that the TCR is believed to be downregulated after T cell activation. Thus, unlike other T cell antibodies, TOL101 has the capability of binding to T cells no matter their activation status.

Figure 7:
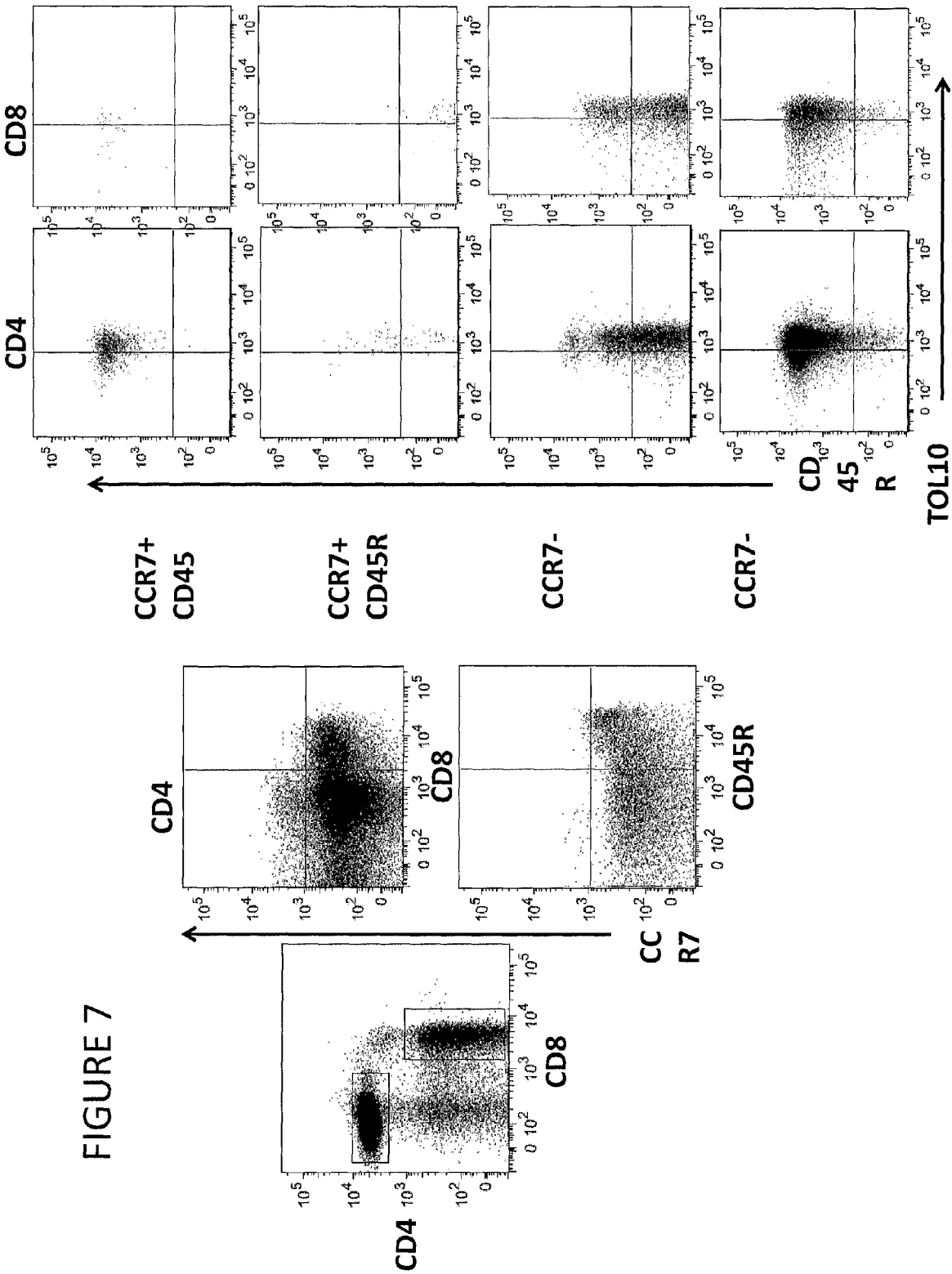
FIG. 7 depicts flow-cytometry pictograms illustrating the specificity of TOL101 to memory subsets αβ TCR+ T-cells from freshly isolated peripheral blood mononuclear cells.

In addition to showing that TOL101 binds to activated T-cells, further experiments were conducted to determine whether TOL101 could bind to specialized memory subsets of T-cells. PBMCs were isolated from buffy coats of three healthy donors. Buffy coats were layered over a Ficol gradient to enrich for lymphocytes. Cells were blocked for 30 minutes at 4° C. with human AB serum. Cells were then stained with following antibodies for 30 minutes at 4° C.: TOL101+anti mouse IgM, CD3, CD4, CD8, CD2, CD62L, CD45RA, CD45RO. Cells were washed and run on a BD FACS Canto U. Data were analyzed by Flow Jo and are representative of 6 patients from 2 independent experiments. As shown in FIG. 7, anti-αβ TCR antibody TOL101 binds to both CD4 and CD8 T-cell memory subsets.

Figure 8:
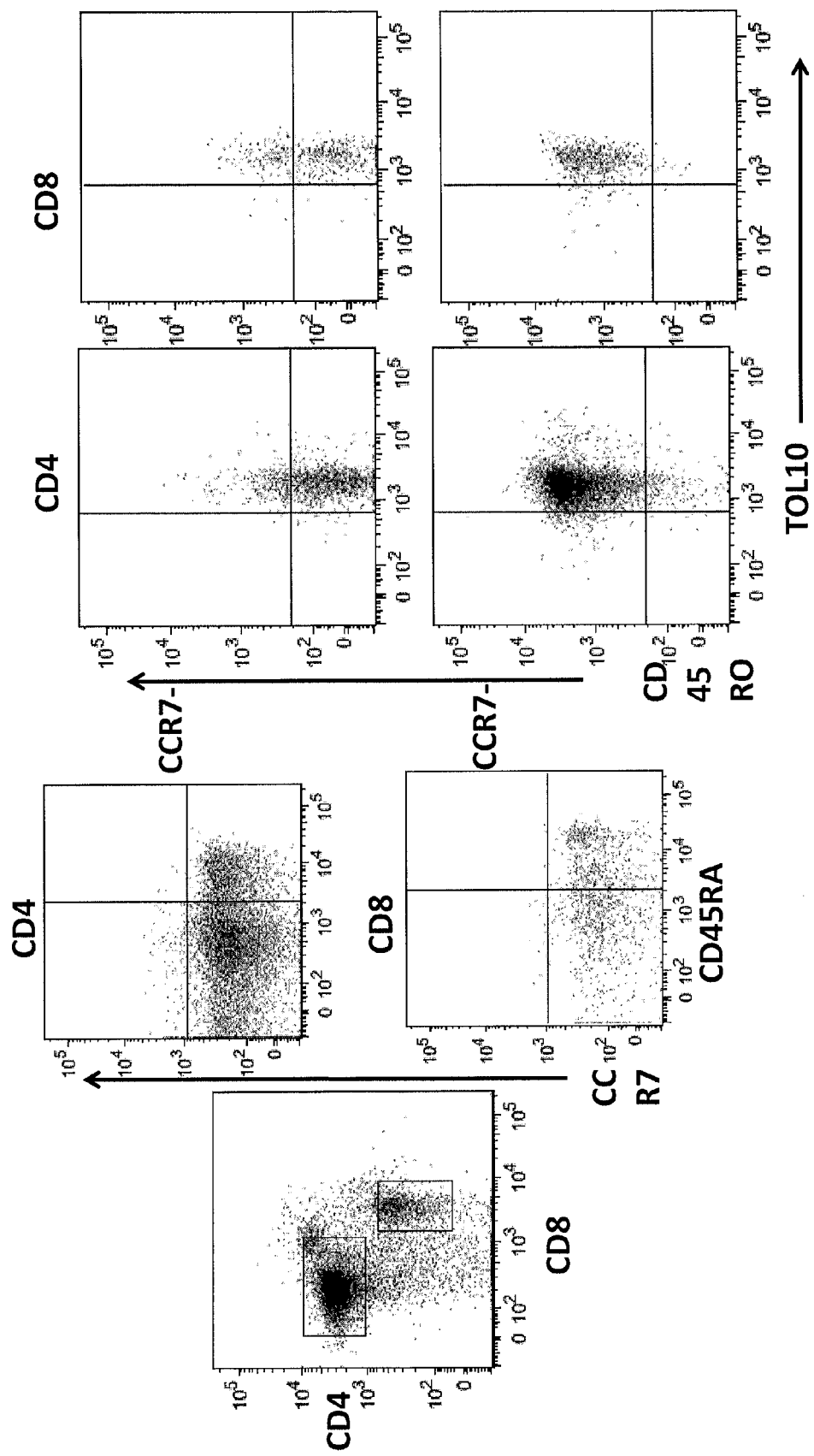
FIG. 8 depicts flow-cytometry pictograms illustrating the specificity of TOL101 to the memory subset αβ T-cells of freshly isolated peripheral blood mononuclear cells after stimulation in a one-way mixed lymphocyte reaction.

To further examine the binding of TOL101 to memory subsets, in another experiment, PBMCs were isolated from huffy coats of three healthy donors. Buffy coats were layered over a Ficol gradient to enrich for lymphocytes. Stimulator cells were then irradiated at 3000 rads. Stimulator and responder cells were co-cultured for 6 days at a ratio of 2:1 ($4\times10^5$ stimulator cells to $2\times10^5$ responder cells). Combinations for cells were as follows: a unit of blood from subject No. 1+a unit of irradiated blood from subject No. 2; a unit of blood from subject No. 1+a unit of irradiated blood from subject No. 3; a unit of blood from subject No. 2+a unit of irradiated blood from subject No. 1; a unit of blood from subject No. 2+a unit of irradiated blood from subject No. 3; a unit of blood from subject No. 3+a unit of irradiated blood from subject No. 1; and a unit of blood from subject No. 3+a unit of irradiated blood from subject No. 2. Cells were analyzed on day 6 of culture. Cells were blocked for 30 minutes at 4° C.: with human AB serum. Cells were then stained with following antibodies for 30 minutes at 4° C.: TOL101+anti mouse IgM, CD3, CD4, CD8, CD2, CD62L, CD45RA, CD45RO. Cells were washed and run on a BD FACS Canto Data analyzed by Flow Jo. As shown in FIG. 8, TOL101 binds to memory and activated T subsets of PBMCs after one-way MLR reactions.

Figure 9:
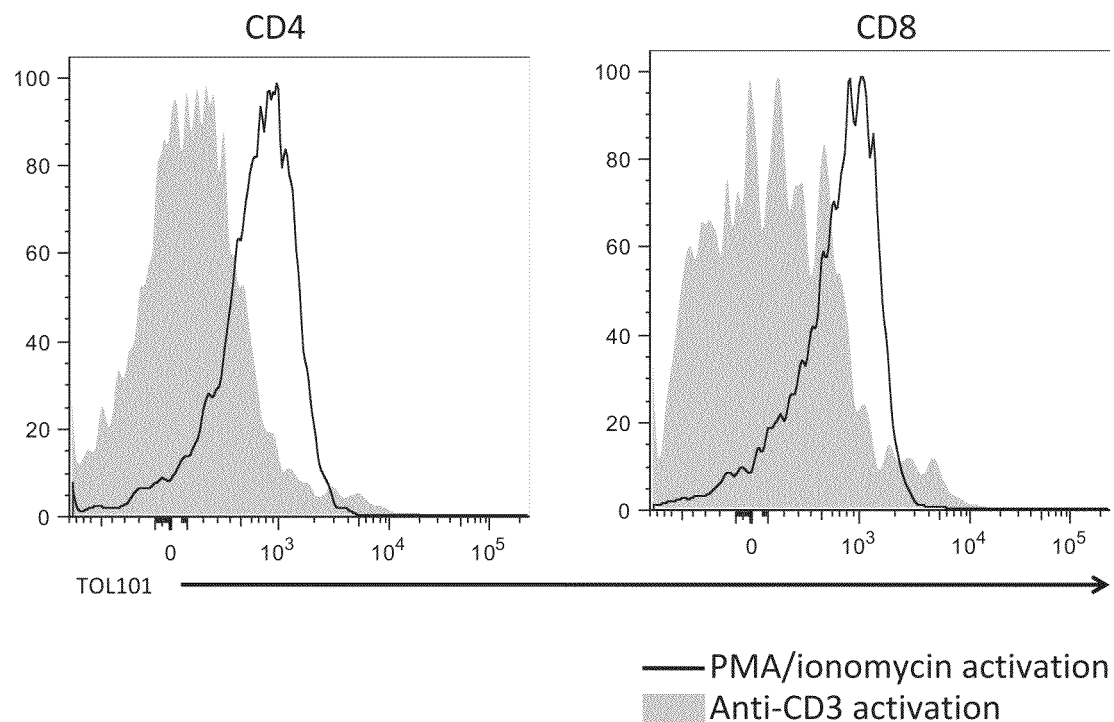
FIG. 9 depicts flow-cytometry pictograms illustrating diminished binding of TOL101 after anti-CD3 activation of freshly isolated peripheral blood mononuclear cells.

In another experiment, the binding characteristics of TOL101 were measured in cells that were previously activated using anti-CD3 antibodies. PBMCs were isolated from huffy coats of three healthy donors. Buffy coats were layered over a Ficol gradient to enrich for lymphocytes. Anti-CD3 (9 μg/mL) or PMI/ionomycin was added at time of culture to cells from each donor. Cells were analyzed on day 6 of culture. Cells were blocked for 30 minutes at 4° C. with human AB serum and stained with TOL101. Cells were washed and run on a BD FACS Canto II, and data were analyzed by Flow Jo. As shown in FIG. 9, TOL101 bound to both CD3 activated cells and, to a greater extent, PMA/ionomycin activated cells.

Figure 10:
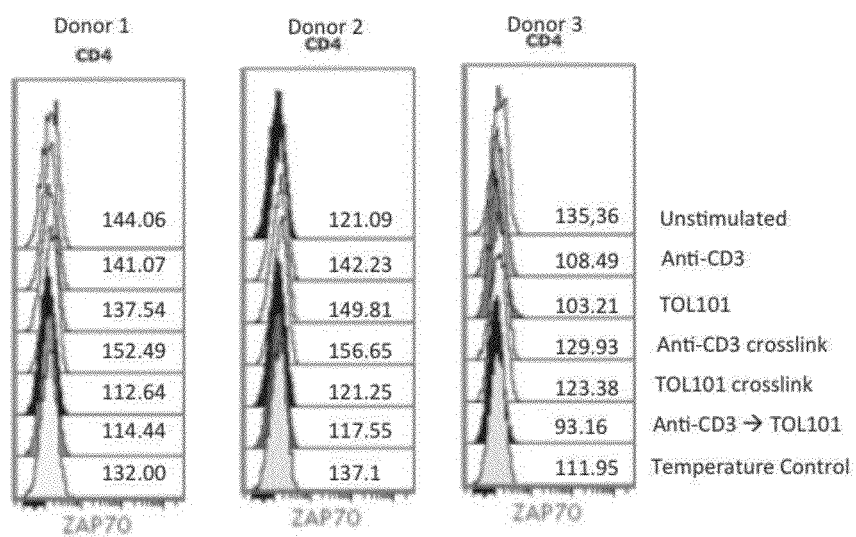
FIG. 10 depicts a histogram of ZAP70 phosphorylation in T-cells and the ability of TOL101 to reduce anti-CD3 mediated ZAP70 phosphorylation.

In another experiment, TOL101 was tested to determine its effect on the phosphorylation of a key activation and signaling component ZAP70. Fresh blood drawn from three healthy donors was stimulated to analyze phosphorylation after activation, according to the following conditions. Unstimulated: 15 min at 37° C.; anti-CD3 TOL101: anti-CD3 15 min at 4° C., aIG 15 min at 37° C., TOL101 15 min at 4° C., aIgM 15 min at 37° C.; anti-CD3 crosslink: anti-CD3 15 min at 4° C., aIG 15 min at 37° C.; anti-CD3: anti-CD3 15 min at 37° C.; TOL101 crosslink: TOL101 15 min at 4° C., aIgM 15 min at 37° C.; and TOL101: TOL101 15 min at 37° C. Antibodies were added at a concentration of 9 μg/mL. After stimulation, cells were fixed, permeabilized, and stained with a T cell antibody cocktail and anti-pZap70 (BD Phosflow T cell Activation Kit-Human). Cells were analyzed on BD FACS Canto II within 4 hours of staining. Histograms of Zap70 phosphorylation and raw fluorescence intensity values are shown in FIG. 10. ZAP70 phosphorylation is diminished in T-cells exposed to anti-CD3 followed by TOL101 24 hours later. Raw values for phosphorylation of ZAP70 are shown in FIG. 10. As described above, TCR mediated T cell activation is the result of ITAM mediated downstream signaling. ZAP-70, a protein tyrosine kinase, contains SRC homology 2 domains (SH2) which bind to the CD3 ITAM domains. The initial activation of ZAP70 is followed by phosphorylation of adaptor proteins and enzymes, ultimately culminating in the activation of transcription factors such as nuclear factor of activated cells (NEAT), FOS, JUN, and nuclear transcription factor kB (NFKB). Without wishing to be bound by theory, the ability for TOL101 to reduce anti-CD3 induced phosphorylated ZAP-70 suggests that binding of TOL101 to its epitope specifically results in T cell down regulation, potentially through protein tyrosine phosphatases such as, for example, PTPN22, CD45, CD148, SHP-1 and SIT, or through an unknown adaptor protein that links the TCR with cell signaling cascades without the need for CD3. Without wishing to be bound by any particular theory, this protein may act similarly to CD81 and CD19 in B cell receptor signaling.

Figure 11:
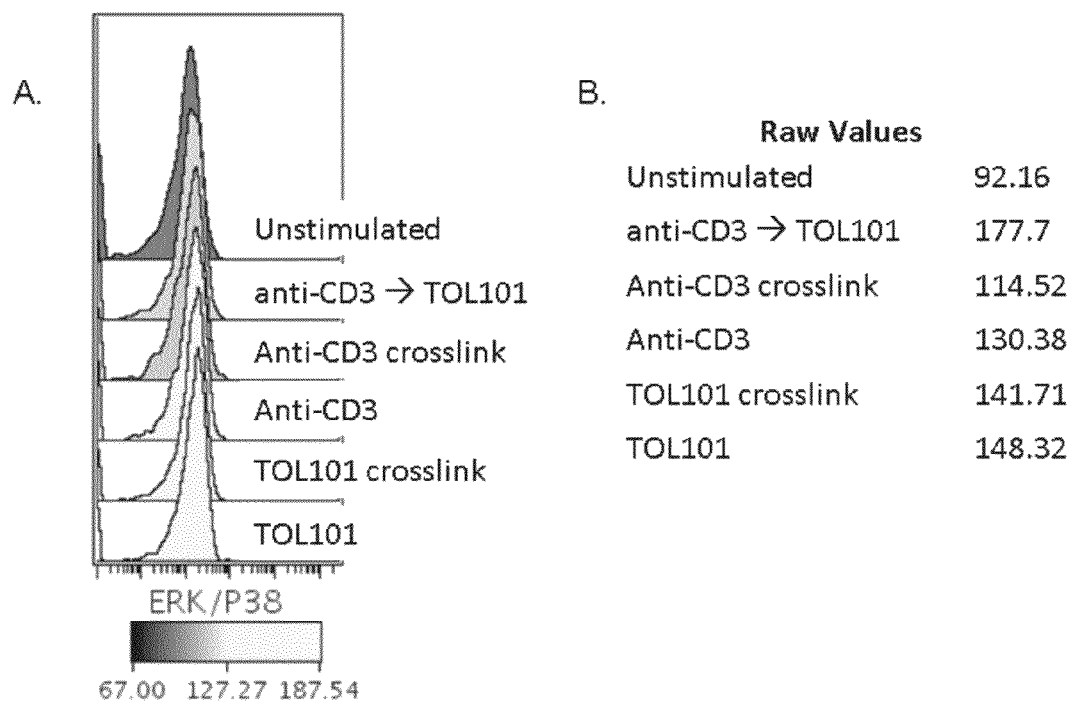
FIG. 11A depicts a histogram of ERK/p38 phosphorylation T-cells under varying conditions and the ability for TOL101 to induce phosphorylated ERK anti-CD3 treated T cells.
FIG. 11B shows the raw values of ERK/p38 phosphorylation under each condition.

In another experiment, TOL101 was tested to determine its effect on the phosphorylation of a key signaling component ERK. Fresh blood drawn from healthy donor was stimulated to analyze phosphorylation after activation under the following conditions. Unstimulated: 15 min at 37° C.; anti-CD3→TOL101: anti-CD3 15 min at 4° C., aIG 15 arum at 37° C., TOL101 15 min at 4° C., aIgM 15 min at 37° C.; anti-CD3 crosslink: anti-CD3 15 min at 4° C., aIG 15 min at 37° C.; anti-CD3: anti-CD3 15 min at 37° C.; TOL101 crosslink: TOL101 15 min at 4° C., aIgM 15 min at 37° C.; and TOL101: TOL101 15 min at 37° C. Antibodies were added at concentrations of 9 μg/mL. After stimulation, cells were fixed, permeabilized, and stained with a T cell antibody cocktail and anti-pERK/p38 (BD Phosflow T cell Activation Kit-Human). Cells were analyzed on BD FACS Canto II within 4 hours of staining A histogram of pERK/p38 phosphorylation (FIG. 11A) and mean fluorescence intensity values (FIG. 11B) are shown. As can be seen in FIG. 11, ERK/p38 phosphorylation is increased in anti-CD3 treated T-cells that are exposed to TOL101 24 hours after anti-CD3 stimulation. Raw values for phosphorylation of pERK/p38 are shown in FIG. 11B. Mitogen activated protein kinases, including ERK, coordinately regulate cell proliferation, differentiation, motility, and survival. TCR stimulation without co-stimulation (in the form of CD28 stimulation for example), usually results in T cell anergy and apoptosis. Thus, the finding that TOL101 induced signaling triggers a survival pathway is surprising. Without wishing to be bound by theory, these data further support the existence of a novel signaling pathway induced by binding of TOL101 to human αβ TCR.

Figure 12:
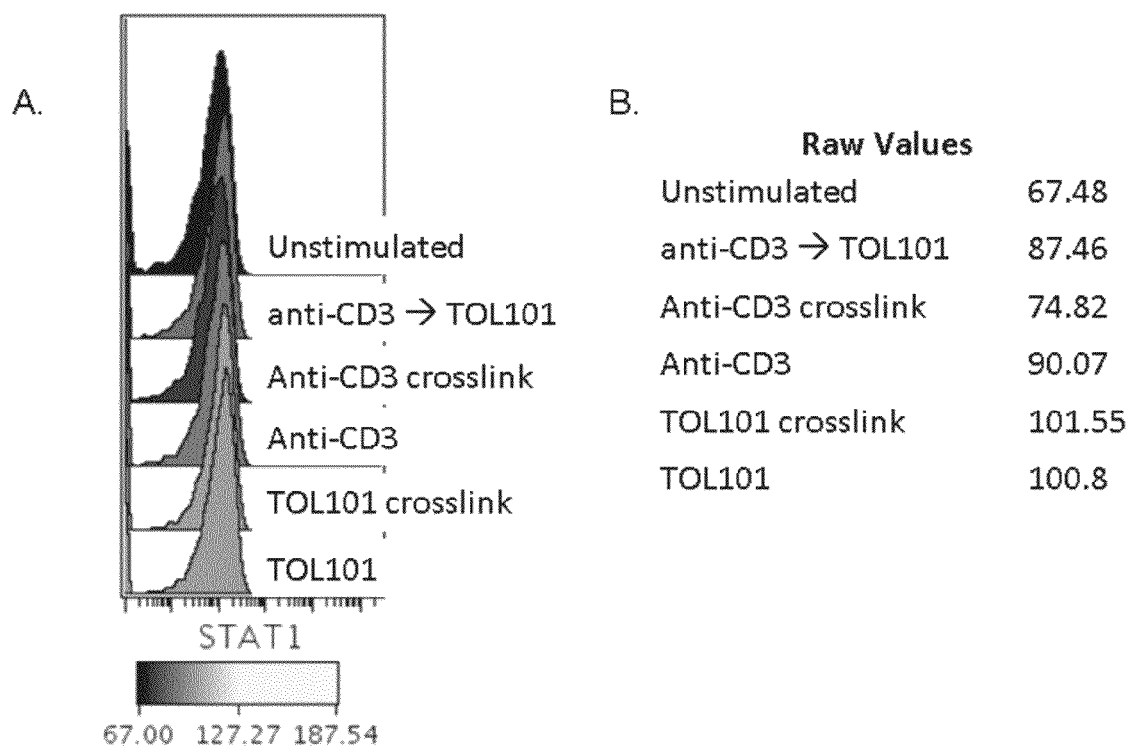
FIG. 12A depicts a histogram of STAT1 phosphorylation T-cells in the presence and absence of anti-CD3 and/or TOL101.
FIG. 12B shows the raw values of ERK/p38 phosphorylation under each condition.

In another experiment, TOL101 was tested to determine its effect on the phosphorylation of a key signaling component STAT1. Fresh blood drawn from healthy donor was stimulated to analyze phosphorylation after activation under the following conditions. Unstimulated: 15 min at 37° C.; anti-CD3→TOL101: anti-CD3 15 min at 4° C., aIG 15 min at 37° C., TOL101 15 min at 4° C., aIgM 15 min at 37° C.; anti-CD3 crosslink: anti-CD3 15 min at 4° C., aIG 15 min at 37° C.; anti-CD3: anti-CD3 15 min at 37° C.; TOL101 crosslink: TOL101 15 min at 4° C., aIgM 15 min at 37° C.; and TOL101: TOL101 15 min at 37° C. Antibodies were added at concentrations of 9 μg/mL. After stimulation, cells were fixed, permeabilized, and stained with a T cell antibody cocktail and anti-STAT1 (BD Phosflow T cell Activation Kit-Human). Cells were analyzed on BD FACS Canto II within 4 hours of staining. a histogram of STAT1 phosphorylation (FIG. 12A) and the mean fluorescence intensity values (FIG. 12B) are shown. As can be seen in FIG. 12, STAT1 phosphorylation is increased when T-cells are exposed to TOL101. Since STAT1 binding cytokines (such as type II interferon) are associated with T cell proliferation and activation, the elevation of phosphorylated STAT1 upon binding of TOL101 was unexpected. Without wishing to be bound by theory, the data suggest a role for STAT1 that is beyond the previously described role of STAT1 in T cell activation. Raw values for phosphorylation of STAT1 are shown in FIG. 12B.

Figure 13:
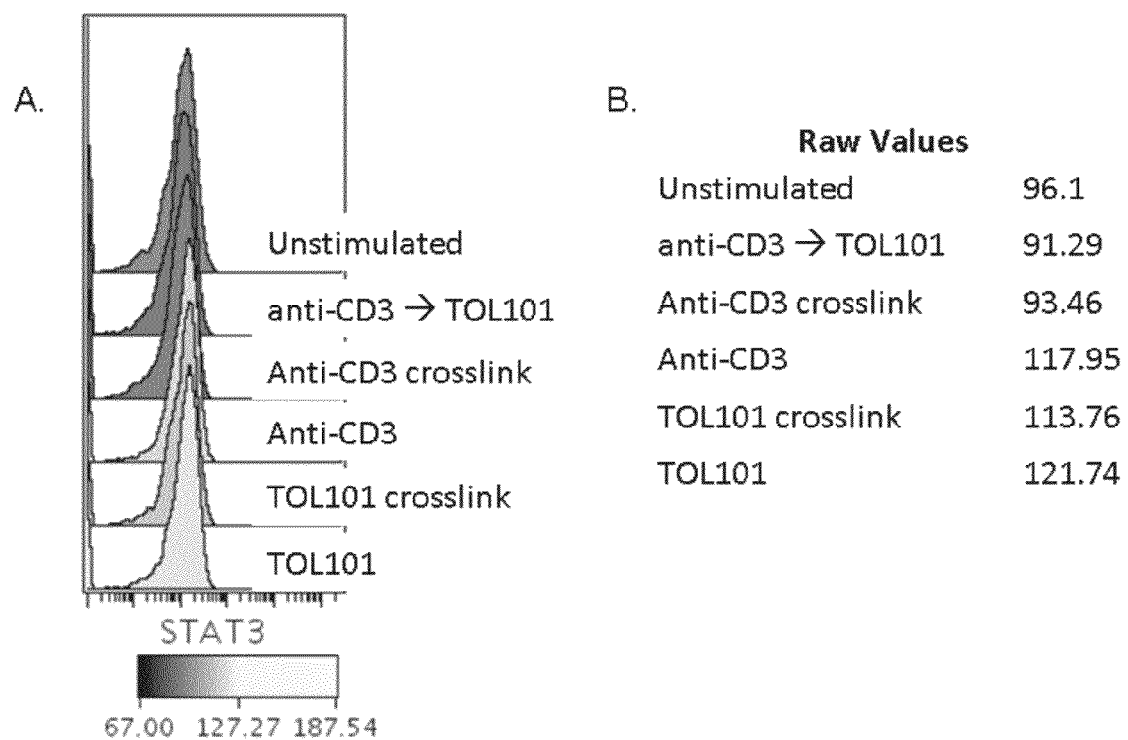
FIG. 13A depicts a histogram of STAT3 phosphorylation T-cells in the presence and absence of anti-CD3 and/or TOL101.
FIG. 13B shows the raw values of ERK/p38 phosphorylation under each condition.

In another experiment, TOL101 was tested to determine its effect on the phosphorylation of a key signaling component STAT3, Fresh blood drawn from healthy donor was stimulated to analyze phosphorylation after activation under the following conditions. Unstimulated: 15 min at 37° C.; anti-CD3→TOL101: anti-CD3 15 min at 4° C., aIG 15 min at 37° C., TOL101 15 min at 4° C., aIgM 15 min at 37° C.; anti-CD3 crosslink: anti-CD3 15 min at 4° C., aIG 15 min at 37° C.; anti-CD3: anti-CD3 15 min at 37° C.; TOL101 crosslink: TOL101 15 min at 4° C., aIgM 15 min at 37° C.; and TOL101: TOL101 15 min at 37° C. Antibodies were added at concentrations of 9 μg/mL. After stimulation, cells were fixed, permeabilized, and stained with T cell antibody cocktail and anti-STAT3 (BD Phosflow T cell Activation Kit-Human). Cells were analyzed on BD FACS Canto II within 4 hours of staining. A histogram of STAT3 phosphorylation (FIG. 13A) and mean fluorescence intensity (FIG. 13B) values are shown. As can be seen in FIG. 13, STAT3 phosphorylation increased comparably in anti-CD3 and TOL101-treated T cells. Raw values for phosphorylation of STAT3 are shown in FIG. 13B.

Figure 14:
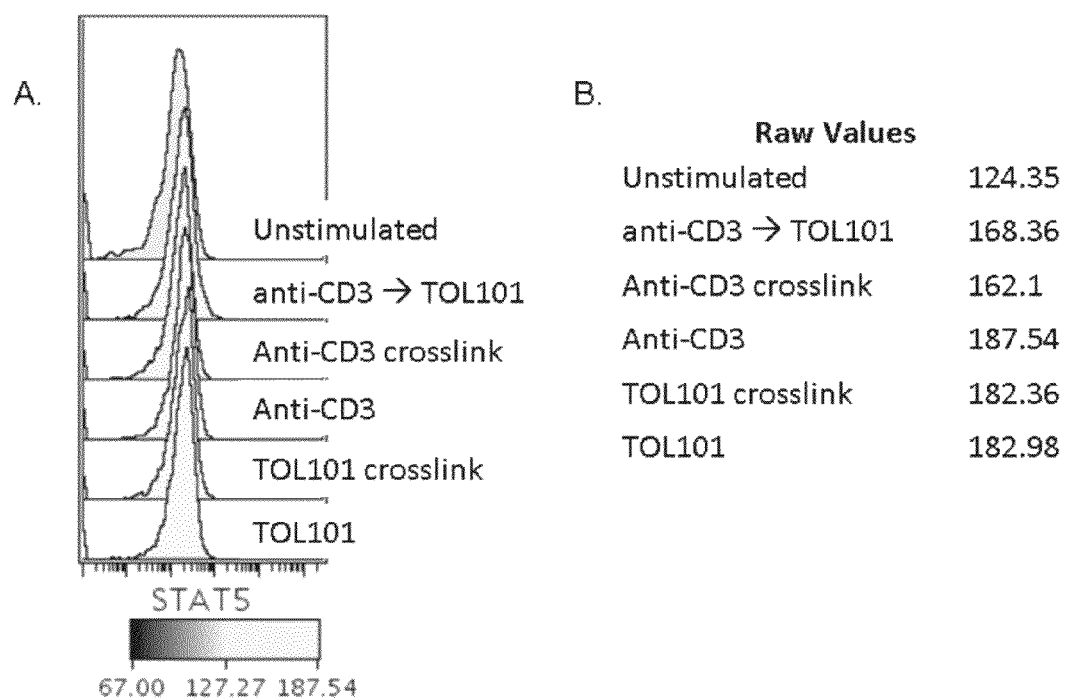
FIG. 14A depicts a histogram of STAT5 phosphorylation T-cells in the presence and absence of anti-CD3 and/or TOL101.
FIG. 14B shows the raw values of ERK/p38 phosphorylation under each condition.

In another experiment, TOL101 was tested to determine its effect on the phosphorylation of a key signaling component STAT5. Fresh blood drawn from healthy donor was stimulated to analyze phosphorylation after activation under the following conditions. Unstimulated: 15 min at 37° C.; anti-CD3→TOL101: anti-CD3 15 min at 4° C., aIG 15 min at 37° C., TOL101 15 min at 4° C., aIgM 15 min at 37° C.; anti-CD3 crosslink: anti-CD3 15 mire at 4° C., aIG 15 mire at 37° C.; anti-CD3; anti-CD3 15 min at 37° C.; TOL101 crosslink: TOL101 15 min at 4° C., aIgM 15 min at 37° C.; and TOL101: TOL101 15 min at 37° C. Antibodies were added at concentrations of 9 μg/mL. After stimulation, cells were fixed, permeabilized, and stained with T cell antibody cocktail and anti-STAT5 (BD Phosflow T cell Activation Kit-Hunan). Cells were analyzed on BD FACS Canto II within 4 hours of staining. A histogram of STAT5 phosphorylation (FIG. 14A) and mean fluorescence intensity values (FIG. 14B) are shown. As can be seen in FIG. 14, STAT5 phosphorylation is increased when T-cells are exposed to TOL101 and/or anti-CD3. Raw values for phosphorylation of STAT5 are shown in FIG. 14B.

Figure 15:
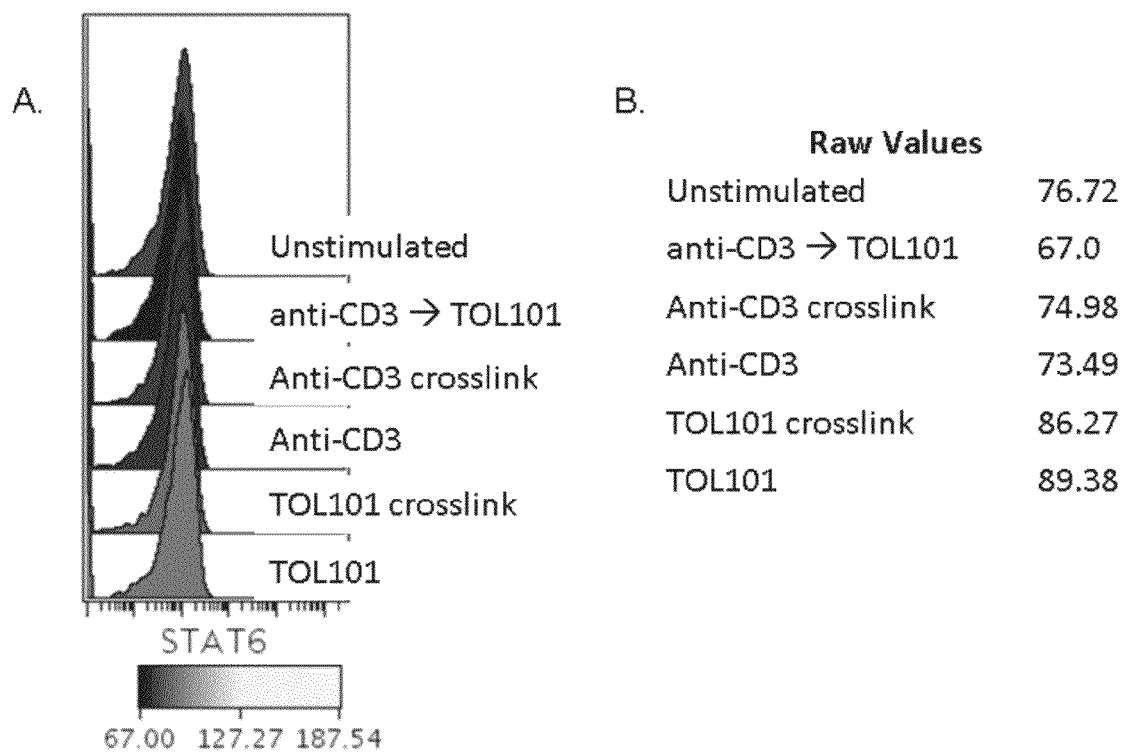
FIG. 15A depicts a histogram of STAT6 phosphorylation T-cells in the presence and absence of anti-CD3 and/or TOL101.
FIG. 15B shows the raw values of ERK/p38 phosphorylation under each condition.

In another experiment, TOL101 was tested to determine its effect on the phosphorylation of a key signaling component STATE. Fresh blood drawn from healthy donor was stimulated to analyze phosphorylation after activation under the following conditions. Unstimulated: 15 min at 37° C.; anti-CD3→TOL101: anti-CD3 15 min at 4° C., aIG 15 min at 37° C., TOL101 15 min at 4° C., aIgM 15 min at 37° C.; anti-CD3 crosslink: anti-CD3 15 min at 4° C., aIG 15 min at 37° C.; anti-CD3: anti-CD3 15 min at 37° C.; TOL101 crosslink: TOL101 15 min at 4° C., aIgM 15 min at 37° C.; and TOL101: TOL101 15 min at 37° C. Antibodies were added at concentrations of 9 μg/mL. After stimulation, cells were fixed, permeabilized, and stained with T cell antibody cocktail and anti-STATE (BD Phosflow T cell Activation Kit-Human). Cells were analyzed on BD FACS Canto II within 4 hours of staining. A histogram of STAT6 phosphorylation (FIG. 15A) and mean fluorescence intensity values (FIG. 15B) are shown. As can be seen in FIG. 15, STAT6 phosphorylation is reduced in anti-CD3 treated T cells, when they are subsequently exposed to TOL101. Raw values for phosphorylation of STAT6 are shown in FIG. 15B.

Example 4

TOL101 Escalation Trial in Renal Transplant Patients

Figure 19:
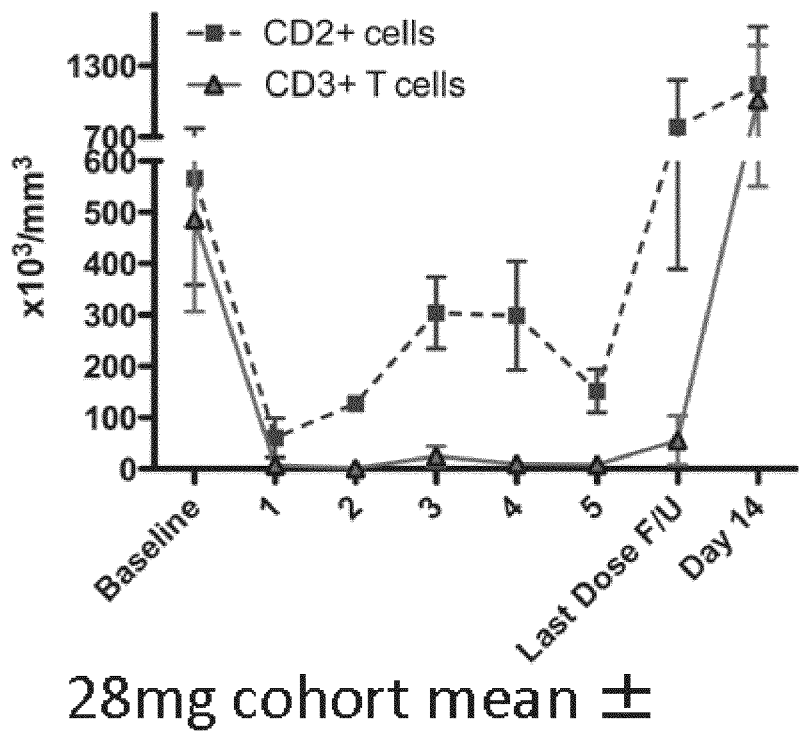
FIG. 19 depicts a line graph representing the T-cell response at 28 mg TOL101 therapy over a two week period, showing the presence of T cells devoid of a TCR complex during the dosing period.
Figure 20:
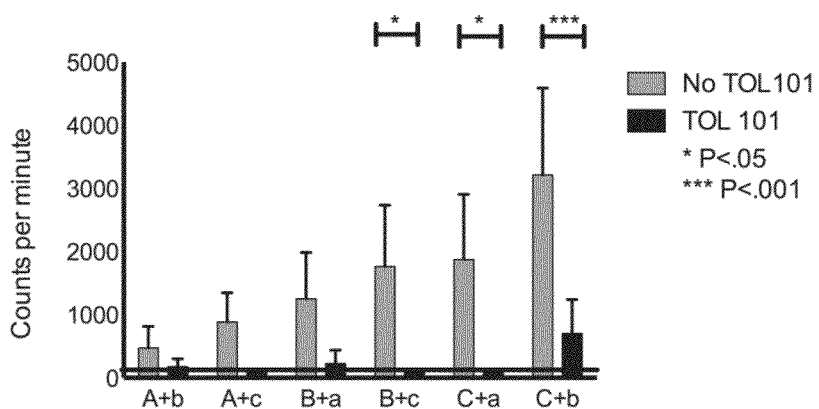
FIG. 20 depicts a bar graph of suppression of anti-alloantigen response in vitro in the presence of TOL101.
Figure 21:
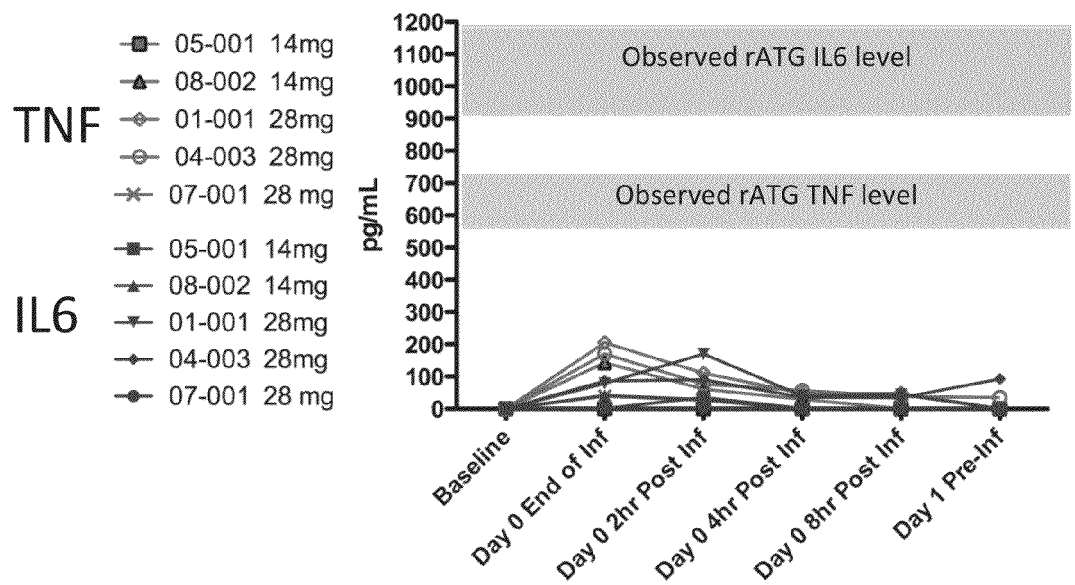
FIG. 21 depicts a line graph of a cytokine release assay using samples obtained from patients infused with TOL101 when compared to historical rATG data at multiple time points.

In a second study of TOL101 administered to first time kidney transplant recipients, standard measures of safety and dosing were measured. The second study has a modified adaptive design including an initial dose-escalation component followed by a randomized active control component. The first part of the study (Part A) is planned to enroll between 4-14 cohorts (2-6 subjects per cohort) at successively higher dose levels with the goal of identifying two potential therapeutic dose levels (PTD-A & PTD-B). Part B, if required, is designed to evaluated TOL101 in a larger number of renal transplant subjects, using a randomized, parallel arm design with Thymoglobulin as the standard of care comparator, and accruing safety and some efficacy data in the target population, renal transplant patients. Thymoglobulin was chosen as the active comparator because it is the most commonly used induction agent for prevention of acute renal allograft rejection in the US and is the standard of care in many centers participating in this study. TOL101 dosing was pegged to trough tacrolimus levels. The trial summary is provided in FIG. 16.

globulin. In addition to broad T-cell inactivation, the 28 mg cohort data showed that TOL101 reduced CD3 expression without depleting T cells, as determined by the presence of CD3− CD2+ T-cells. (FIG. 19). While TOL101 may be non-depletional, it is strongly capable of inhibiting the alloreactive response in mixed lymphocyte reactions. This mechanism of action results in strong prevention of the anti-alloantigen response in-vitro (See FIG. 20). The infusion of TOL101 did not trigger any significant cytokine release syndrome symptoms, or strong production of TNF-α or IL-6, further supporting the clinical safety profile outlined above in Table 9. Levels of TNF-α and IL-6 (shown in FIG. 21), as well as IL-1β, IFNγ and IL-2 (not shown) are being determined at multiple time points after infusion. Minimal amounts of these cytokines have been detected in TOL101 treated subjects. TNF-α and IL-6 have been detected at very low levels, especially when compared to historical rATG data. No cytokine

TABLE 9

Safety and Side Effects After Dosing With TOL101

| Measurement | TOL101 Dose | | | | |
|---|---|---|---|---|---|
| | 0.28 mg (n = 2) | 1.4 mg (n = 2) | 7 mg (n = 2) | 14 mg (n = 2) | 28 mg (n = 3) |
| Infusion Reactions Symptoms | 0 | 4/14 doses Mild nausea & moderate Pruritus | 0 | 1/14 doses Mild rash | 5/20 doses Mild/moderate Tachycardia, headache, hypertension, pruritus |
| Drug Related SAE's | 0 | 0 | 0 | 0 | 1* |
| Infections & Malignancies | BK Virus D 90 114,000 copies | None Reported | UTI Infection | None Reported | Nosocomial Pneumonia |
| Biopsy proven acute rejection | Grade 1 A acute T cell rejection D 34 Post TX | 0 | 0 | 0 | 0 |

| Hematology 28 mg cohort-compared at days 0, 1, 2, 3, 4, 5, 6, 14 and 28 post transplant | | | |
|---|---|---|---|
| Hematocrit | No change from pre-op baseline | Lymphocytes | First dose reduction |
| Hemoglobin | No change from pre-op baseline | Neutrophils | Elevated after transplant |
| Eosinophils | No change from pre-op baseline | Platelets | No change from pre-op baseline |
| Basophils | No change from pre-op baseline | RBC | No change from pre-op baseline |
| Monocytes | No change from pre-op baseline | WBC | No change from pre-op baseline |

Testing of TOL101 at 0.28, 1.4, 7, 14, 28, 32 and 42 mg per day for 5-8 days as well as an escalating strategy starting at either 14 or 21 mg through 28 and 42 mg per day have been assessed. The first cohorts are summarized in FIG. 17. From a safety perspective, TOL101 has been well tolerated. Infusion reactions reported to date have been mild and easily managed (Table 9). Importantly, no acute rejections have been reported at dose levels at which T-cell modulation appeared to be at or near therapeutic levels. Hematological parameters also support a strong safety profile for TOL101 (Table 9). Examination of the pharmacodynamic effect of TOL101 in these patients shows a strong CD3 modulation which increases with TOL101 dose (FIG. 18). The pharmacodynamic target of <50 T-cells/mm³ was achieved in the 28 mg cohort. Unlike alemtuzumab and Thymoglobulin, patients treated with TOL101 show modulation of memory T-cells and naive T-cells, which may increase efficacy of TOL101 relative to currently used agents. Furthermore, unlike other TCR targeting drugs, TOL101 does not reduce the overall white blood cell count (indicating that TOL101 functions through a non-depletional mechanism), nor does it impact thrombocytes levels, a common side-effect of thymorelease syndrome has been reported. In addition, the anti-inflammatory cytokine IL-10 increases upon infusion with TOL101.

The data presented herein supports the safety and efficacy of TOL101, Taken together with the in vitro data presented above, the results of the study show that TOL101 inhibits activation of T cells, including proliferation and production of inflammatory cytokines, without inducing T cell depletion. Furthermore, important elements, such as TOL101's ability to modulate all subsets of TCR+ T cells including those with a memory phenotype, and its non-depletional mechanism of action, are likely to combine to provide better anti-rejection therapy as well as reduce the risk of post-transplant lymphoproliferative disorder (PTLD, a form of malignancy). In conclusion, treatment of subjects with TOL101 results in therapeutic efficacy as determined by CD3+ cell counts reduced to below 25 mm³, CD2+ T-cells emerge with no αβ TCR/CD3, thus resulting in inactivation of αβ-TCR+ T-cells without depleting these cells. Lack of a TCR equates to a non-functional T-cell.

Figure 22:
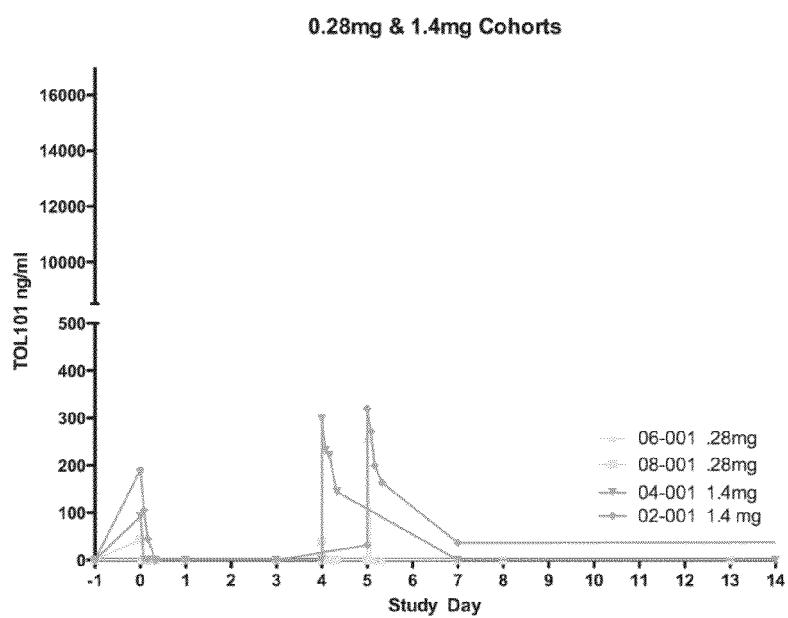
FIG. 22 depicts a line graph of a time course of bioavailability of TOL101 at 0.28 and 1.4 mg dosages over a period of time; results are displayed as plasma levels of TOL101.
Figure 23:
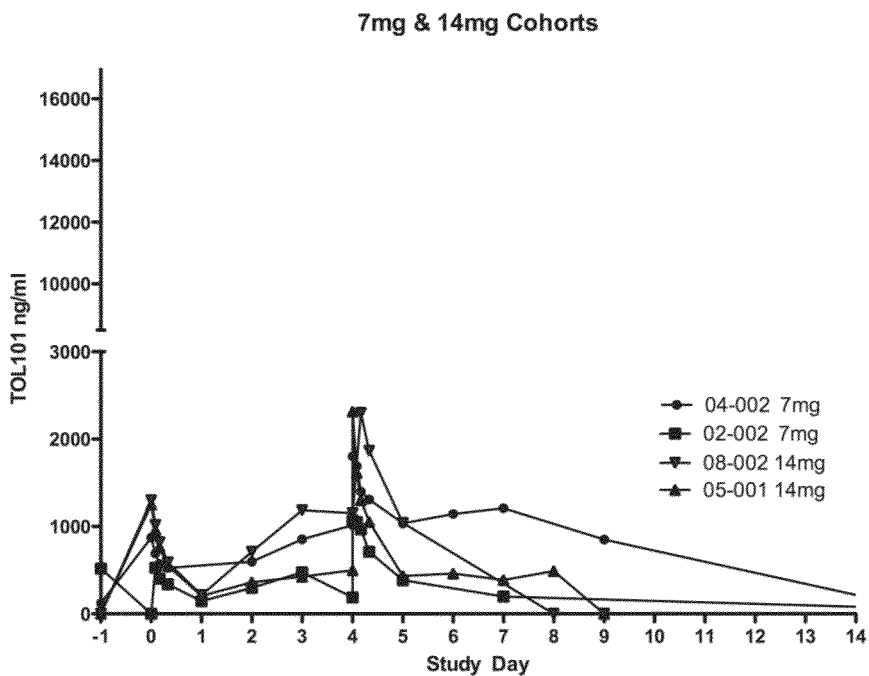
FIG. 23 depicts a line graph of a time course of bioavailability of TOL101 at 7 and 14 mg dosages over a period of time; results are displayed as plasma levels of TOL101.
Figure 24:
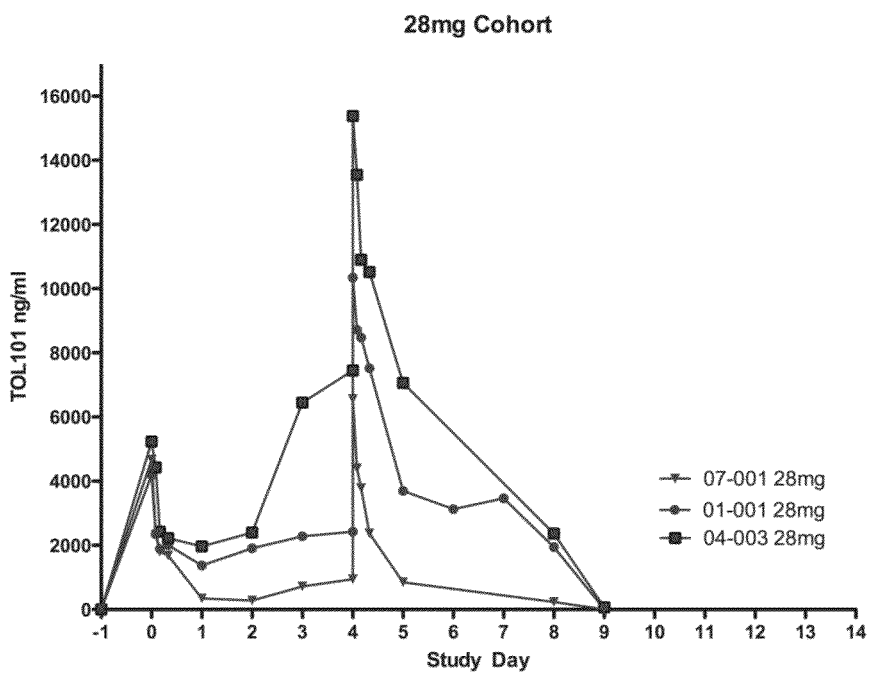
FIG. 24 depicts a line graph of a time course of bioavailability of TOL101 at a 28 mg dosage over a period of time; results are displayed as plasma levels of TOL101.

As shown in FIGS. 22-24, dose escalation of TOL101 shows increased bioavailability (with concomitant increases in AUC), increased serum half-life, and no appreciable anti-mouse antibody reactions in the treated subject. TOL101 dose escalation has occurred with a promising safety profile. TOL101 induced dose dependent T-cell modulation without inducing significant cytokine release or other serious adverse events (SAEs). Immune monitoring shows specific targeting and mechanism of action to be functionally inactivating without depleting. The data supports the potential of TOL101 to provide increased specificity and long-term safety index over currently used induction agents.

Figure 17:
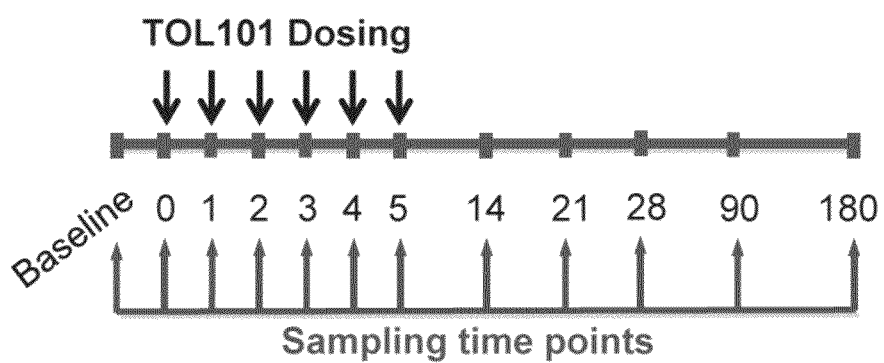
FIG. 17 depicts a schematic representation of dosing schedules for the treatment protocol of FIG. 16.
Figure 18:
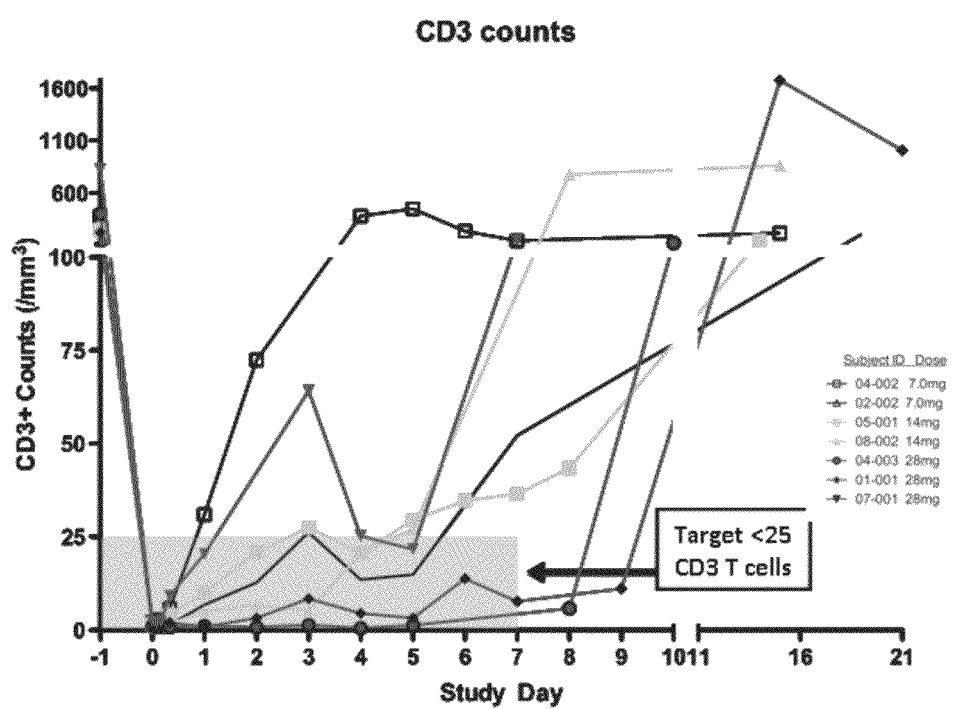
FIG. 18 depicts a line graph of a time course of human patient CD3 counts in the presence of TOL101 at varying concentrations.
Figure 25:
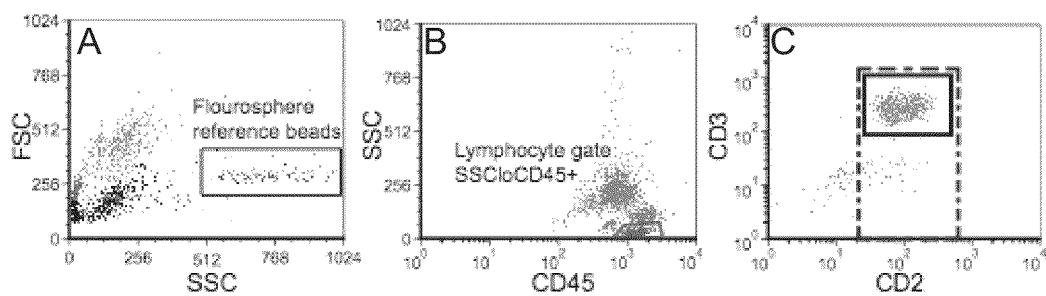
FIG. 25 depicts flow cytometry results of T-cell counts obtained from whole blood using the Beckman Coulter Flow-Count Flourospheres procedure. Gated results are indicative of CD2, CD3 and CD45 expression after incubation with TOL101.
Figure 26:
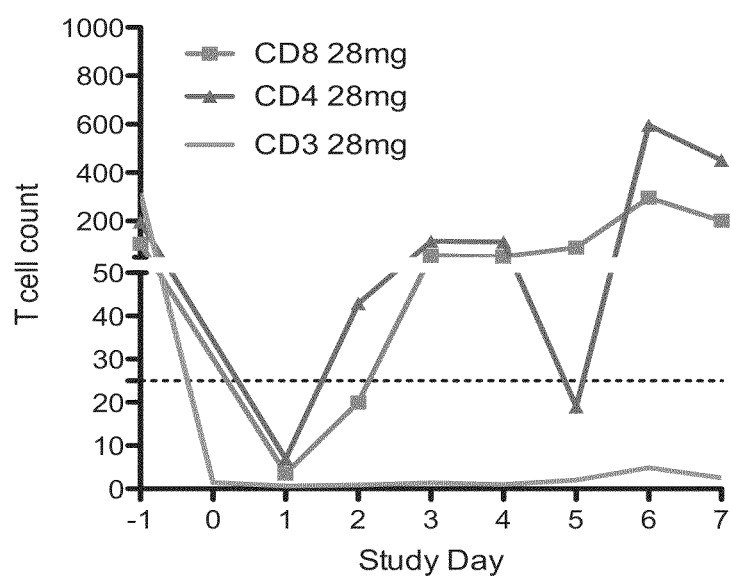
FIG. 26 depicts a line graph illustrating T-cell phenotype expression marker CD3, CD4 and CD8 changes over a period of time after exposure with TOL101.
Figure 27:
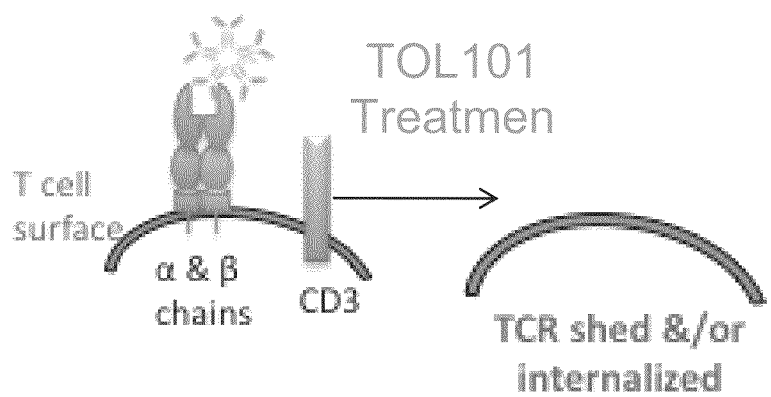
FIG. 27 is a schematic representation of the mechanism of action of TOL101 with respect to αβ TCR+ T-cells. The schematic shows that TOL101 causes the removal of the TCR complex from the cell surface without depleting the cells.

After administration of TOL101 using the dosing schedule shown in FIG. 17, flow cytometry was used to determine T-cell counts from whole blood using the Beckman Coulter Flow-Count Fluorospheres procedure. T-cell phenotype analysis is conducted on Ficoll separated samples. In the current study, the expression profiles of CD3, CD4, CD8, CD45RA and CD45RO are provided in the present example as shown in FIGS. 25-27. All procedures are performed at a central laboratory. In addition to these proteins, the following parameters were also measured: CD3 counts and immunophenotyping, cytokine production (IL-2, IL-6, TNF-α, and IFN-γ) analysis, HAMA analysis and standard hematological analysis.

As shown in FIG. 25, flow cytometry analysis after TOL101 therapy was performed and shown in FIGS. 25A-25C. Gating strategy for CD3 counts was elected, showing bead standards (25A), Lymphocyte gating (25B) and CD2 vs. CD3 gating (25C). Note CD3 counts given by solid box. TOL101 was shown to reduce the CD3 count in a dose-dependent manner. The data presented herein support removal of the TCR complex from the cell surface without depleting the cells as shown in FIG. 26. Similar to the CD2+ data shown in FIG. 19, while the percentage of cells expressing CD3 was dramatically reduced after treatment with TOL101, the numbers of CD4+ and CD8+ cells remained at normal levels, as shown in FIG. 26. A proposed a mechanism for CD3 depletion following administration of TOL101 is schematically represented in FIG. 27.

Example 5

TOL101 Escalation Study

A clinical experiment was designed to test the efficacy of an escalation dosing protocol. Escalation dosing may be used to prevent or ameliorate potential side effects, such as rashes in patients dosed with a TCR down modulation agent such as TOL101 antibody. For example, a rash may be the result of αβ TCR stimulation and subsequent release of preformed stores, such as granzyme or perforin, among many others. The rationale, although not necessary to understand the present invention, is believed to include using low doses of TOL101 antibody to trigger T-cell release of preformed stores at a level below the threshold that would trigger any clinical obvious symptoms, followed by higher doses of TOL101 antibody to complete the TCR down modulation after pre-formed stores have been exhausted, thereby preventing clinical symptoms such as a rash. To test this hypothesis, TOL101 antibody was administered using the following dosing strategy:

TABLE 10

Dosing strategy

| Day | Dose |
| --- | --- |
| 0 | 14 mg |
| 1 | 21 mg |
| 2 | 28 mg |

TABLE 10-continued

Dosing strategy

| Day | Dose |
| --- | --- |
| 3 | 42 mg |
| 4 | 42 mg |
| 5 | 42 mg |

2 patients were initially enrolled into this dosing strategy. Both patients displayed excellent T-cell modulation, however, none of the dosed patients developed any form of rash or other potential serious adverse event. Together, these data show a novel way to dose biologics in an attempt to reduce rash development and other serious adverse events. In addition, the dosing strategy shown in Table 10 can be useful in administering a biologic or antibody (including anti-αβ TCR antibodies like TOL1.01) in patients suffering from a wide-range of diseases including, but not limited to, an autoimmune disease, an inflammatory disease, or a graft tissue rejection (for example, a renal transplantation rejection reaction).

Example 6

Induction and/or Upregulation of Treg Cells Upon Escalating TOL101 Dosing

In an experiment to determine clinical hematological outcomes after tissue transplantation and administration of TOL101, patients were dosed with TOL101 in either a constant dosing regimen (i.e., patients were administered the same dosage of TOL101 mAb, e.g., 0.28 mg/day, 1.4 mg/day, 7 mg/day, 14 mg/day, 28 mg/day, or 32 mg/day on each day of the dosing regimen) or an escalation dosing regimen comprising: 14 mg at day 1, 21 mg at day 2, 28 mg at day 3, 42 mg at day 4, 42 mg at day 5, and 42 mg at day 6. T-cells, vital signs and other biochemical parameters were analyzed. In addition to TOL101 antibody, background therapies also administered included:

1. intravenous Methylprednisolone, 500 mg prior to TOL101 dose 1 and 125-250 mg prior to dose 2 and 3.
2. Oral Prednisone, 100 mg prior to dose 4, after which steroids were tapered down to 20-30 mg by day 14
3. Intravenous Benadryl prior to the first 2 doses (50 mg)
4. Daily doses of tacrolimus to begin no sooner than 6 hours after transplant and no later than 6 days after transplant
5. Daily doses of Mycofenolate Mofetil to begin on the day of or the day following transplant The first dose of TOL101 was given in the operating room beginning after the subject was anesthetized and before unclamping (reperfusion of the allograft).

In this study, the pharmacodynamic target was T-cell counts below 25 cells/mm$^3$. This pharmacodynamic target is considered sufficient to provide the required T cell modulation to prevent transplant rejection. The escalating dosing regimen significantly reduced the CD3 count from baseline (Table 11).

TABLE 11

Example Patient T-cell counts (ID 07-006 & 07-007)

Patient ID 07-006

| Day | Concurrent Therapy | Dose (mg) | T cell count (mm$^3$) |
| --- | --- | --- | --- |
| 0 | MMF<br>IV Steroid | 14 | 501.81 |

TABLE 11-continued

Example Patient T-cell counts (ID 07-006 & 07-007)

| | | | |
|---|---|---|---|
| 1 | Benadryl MMF IV Steroid | 21 | 6.41 |
| 2 | Benadryl Tacrolimus MMF IV Steroid | 28 | 4.37 |
| 3 | Tacrolimus MMF Oral Steroid | 42 | 3.27 |
| 4 | Tacrolimus MMF Oral Steroid | 42 | 8.47 |
| 5 | Tacrolimus MMF Oral Steroid | 42 | 3.74 |
| Last Dose Follow Up (Day 7) | Tacrolimus MMF Oral Steroid Tacrolimus | N/A | 6.92 |

Patient ID 07-007

| Day | Concurrent Therapy | Dose | T cell count |
|---|---|---|---|
| 0 | MMF IV Steroid Benadryl | 14 | 232.94 |
| 1 | MMF IV Steroid Benadryl Tacrolimus | 21 | 9.29 |
| 2 | MMF IV Steroid Tacrolimus | 28 | 4.79 |
| 3 | MMF Oral Steroid Tacrolimus | 42 | 9.11 |
| 4 | MMF Oral Steroid Tacrolimus | 42 | 13.16 |
| 5 | MMF Oral Steroid Tacrolimus | 42 | 5.16 |
| Last Dose Follow Up (Day 7) | MMF Oral Steroid Tacrolimus | N/A | |

Figure 28:
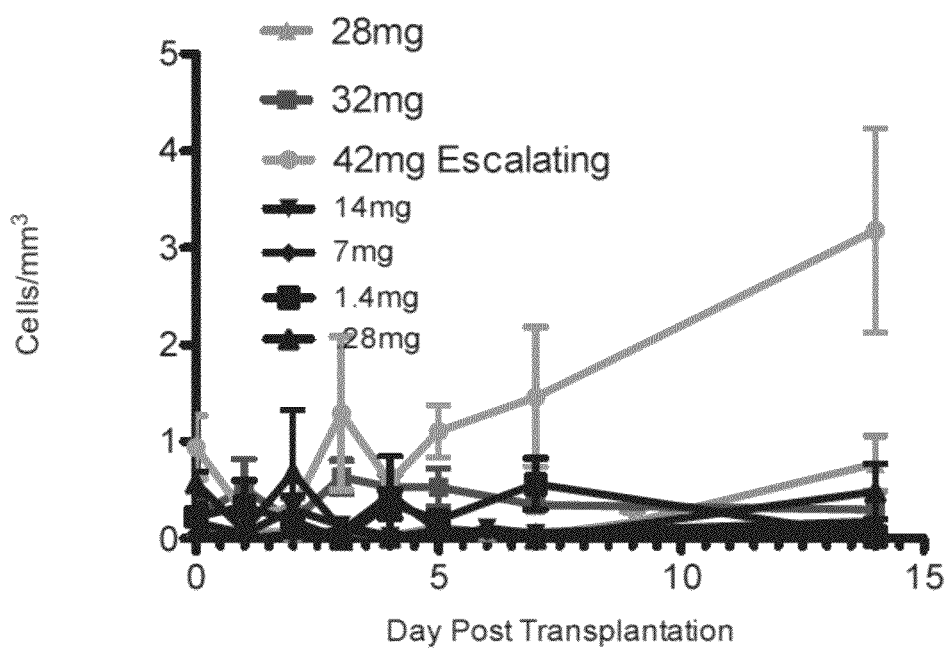
FIG. 28 is a line graph demonstrating Treg induction in clinical study patients that received a dose escalating regimen of TOL101.

Measurements of Treg (CD2+ CD4+ CD25+ FOXP3+ CD127lo) from each patient was performed on each day up until day 14 post transplantation. The results are shown in FIG. 28. Surprisingly, Tregs were induced in patients receiving the escalated dosing regimen, but were not induced in patients receiving the same dose on each day of treatment, even in those patients receiving a dose as high as 32 mg/day.

During the adaptive immune response, in general, interaction and communication between the MHC/peptide complex on Antigen Presenting Cells (APCs) and the T cell receptor (TCR) of T effector cells leads to activation and the secretion of pro-inflammatory cytokines such as IL-4, and IFN-γ. On the other hand the activation of natural T-regulatory T-cells (Treg T-cells) leads to the expression of the immune suppressive cytokines IL-10 and TG-β, among others. These cytokines act directly on nearby effector T cells leading in some cases to anergy or apoptosis. In other cases regulatory cytokines and chemokines convert effector T cells to T regulatory phenotypes; this process is referred here as "induced" or "adaptive" tolerance. T cell epitopes that are capable of binding to MHC molecules and engaging and activating circulating Treg T-cells are referred to as Treg epitopes. As used herein, the various methods for treatment and for upregulating cellular numbers of Treg T-cells generally refer to functional Treg T-cells, for example, those Treg T-cells expressing surface markers $CD2^+$ $CD4^+$ $CD25^+$ $FOXP3^+$ and $CD127^{lo}$.

Initial self/non-self discrimination occurs in the thymus during neonatal development where medullary epithelial cells express specific self protein epitopes to immature T cells. T cells recognizing self antigens with high affinity are deleted, but autoreactive T cells with moderate affinity sometimes avoid deletion and can be converted to so called natural Treg-T-cells. These natural Treg T-cells are exported to the periphery and provide for constant suppression of autoimmunity. Natural Treg T-cells are a critical component of immune regulation and self tolerance.

Self tolerance is regulated by a complex interplay between T cells, B cells, cytokines and surface receptors. T regulatory immune responses counterbalance T effector immune response to protein antigens (whether self or foreign). A tilt of the balance toward the autoreactive side, either by increasing the number or function of autoreactive T effector cells or by diminishing the number or function of Treg T-cells, is manifested as autoimmunity.

A second form of tolerance occurs in the periphery where mature T cells are converted to an "adaptive" Treg T-cell phenotype upon activation via their T cell receptor in the presence of IL-10 and TGF-β, usually supplied by bystander Treg T-cells. The possible roles for these "adaptive" Treg T-cells include dampening immune response following the successful clearance of an invading pathogen as a means of controlling excessive inflammation as might be caused by an allergic reaction or low level chronic infection, or possibly to facilitate co-existence with beneficial symbiotic bacteria and viruses. "Adaptive" Treg T-cells may also play a role in managing the life cycle of human antibodies that have undergone somatic hypermutation.

Treg T-cells are also instrumental in B cell tolerance. B cells express a single low affinity Fc receptor, FcγRIIB on their cell surface. This receptor contains the immunoreceptor tyrosine-based inhibition motif sequence (ITIM) in its cytoplasmic domain. Co-ligation of FCγRIIB and the BCR by immune complexes act to trigger the tyrosine phosphorylation of the ITIM leading to the recruitment of the inositol phosphatase, SHIP, which inhibits BCR-triggered proliferation by interfering with the activation of MAP kinases and blocks phagocytosis by the dissociation of Burton's tyrosine kinase (Btk) from the cell membrane, which inhibits calcium influx into the cell. FcγRIIB can also induce apoptosis independent of the ITIM. Upon homo-aggregation of FcRIIB by ICs, the association of Btk with the cell membrane is enhanced triggering an apoptotic response. Expression of FcγRIIB is highly variable and cytokine dependent. IL-4 and IL-10, which are expressed by activated Th2 and Treg T-cells, have been shown to act synergistically to enhance FcγRIIB expression thus aiding in the suppression of a humoral response.

The present invention provides unexpected and surprising therapeutic upregulation of Treg T-cells in patients that are administered with anti-αβ TCR antibody TOL101, using a specific escalation dose regimen in patients. Without wishing to be bound by any particular theory, it is believed that using a low dose TOL101 antibody in a patient who is experiencing or will experience some allo- or auto-reactive response will elicit a cascade of novel signaling events (involving ZAP70 down regulation, AKT and ERK modulation, as well as potential calcium flux), as well as the production of a low level of IL2. This belief is supported by the studies in patients with vasculitis induced by the hepatitis C virus which have reduced levels of Treg T-cells (Saadoun, D. et al. N. Engl. J.

Figure 29:
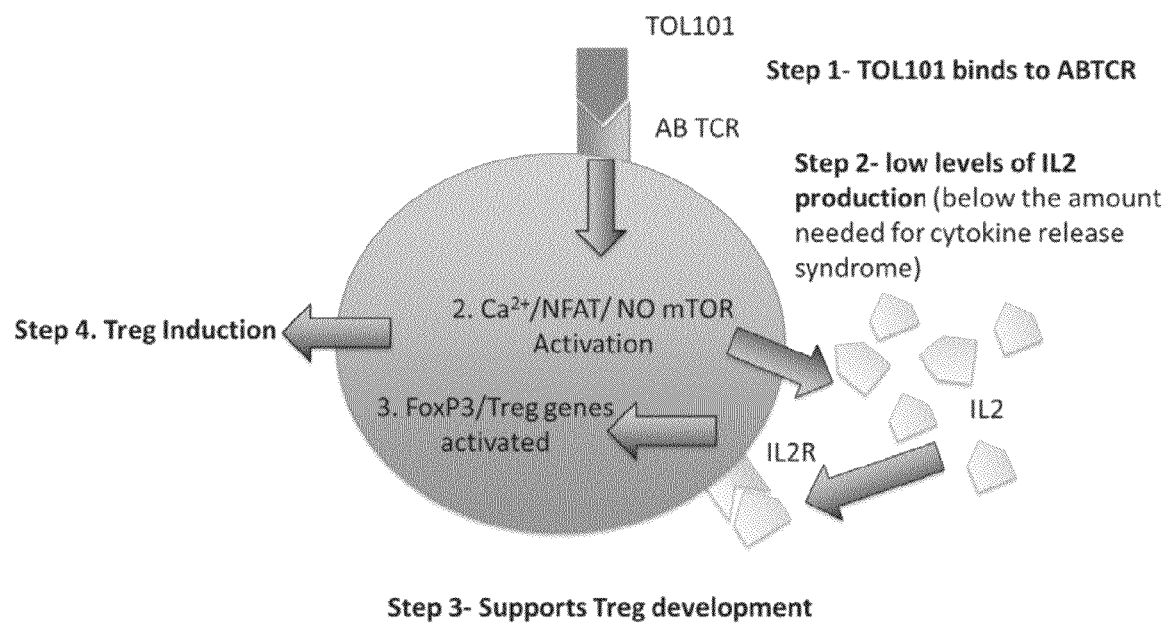
FIG. 29 is a schematic of the initial steps of TOL101 binding and inducing Tregs.
Figure 30:
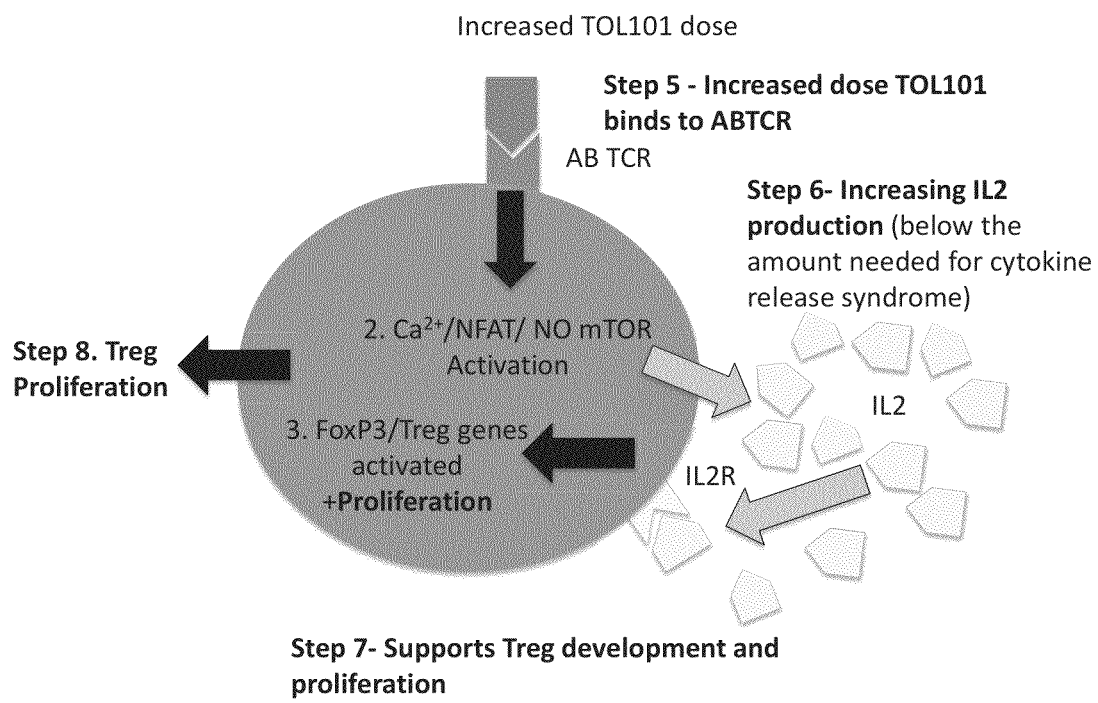
FIG. 30 is a schematic continued from FIG. 29, showing a potential pathway through which TOL101 induces Tregs when it is given in a dose escalating regimen.

Med, 365(22) 2067-2077). As shown in Saadoun et al., low level IL2 stimulates Treg T-cell induction. Over a few days the Treg genes are functional with Treg phenotype in place. Without wishing to be bound by theory, it is believed that as the TOL101 mAb dose is increased, as exemplified in the present disclosure, not only is there a localized increase in/L2, but a set of unique transcription factors are initiated that supports the expansion of Treg T-cells in vivo. It is worth noting that the levels of IL2 produced in response to the administration of TOL101 mAb are lower than normally considered needed for classical T-cell activation and proliferation. As such, while IL2 is being produced and supporting Treg T-cell expansion, the levels of IL-2 are lower than those required to induce cytokine release syndrome. It is possible at this point to exploit specific Treg-cells to suppress unwanted immune responses and to induce adaptive Treg T-cells to suppress alloreactive and autoimmune responses challenged with self-antigen. A schematic representation is shown in FIGS. 29 and 30. This discovery has implications for the design of therapeutic regimens and antigen-specific therapies for transplantation, protein therapeutics, allergy, chronic infection, autoimmunity and vaccine design. Administration of TOL101 mAb in the specific escalation dosing regimen described herein can be used to augment and increase cellular numbers of Treg T-cells which in turn can be used to suppress effector immune response. In some embodiments, TOL101 mAb is administered to the patient before, at or after the onset of symptoms of autoimmune disease or before, at or after tissue transplantation. In some embodiments, administration of TOL101 mAb in a transplantation procedure commences at the time of transplantation. i.e. on the same day, hence day 1 of the dosing schedule is the day of transplantation. In other embodiments, TOL101 may be administered to a subject that has previously received a tissue transplant. In some embodiments the escalation dosing regimen comprises administering TOL101 to the subject at 14 mg at day 1, 21 mg at day 2, 26 mg at day 3, 42 mg at day 4, and 42 mg at day 5. In other embodiments, the escalation dosing regimen comprises administering TOL101 to the subject at 14 mg at day 1, 21 mg at day 2, 26 mg at day 3, 42 mg at day 4, 42 mg at day 5, and 42 mg at day 6. In some embodiments, the escalated dosing of TOL101 as described herein over a 5 or 6 day period is performed only once, as it is believed that a one time escalation dosing of TOL101 mAb is exemplified for induction dosing.

The administration of anti-αβ TCR antibody TOL101 using an escalation dosage regimen described herein is useful in the selective engagement and activation of Treg T-cells. It is demonstrated herein that certain pre-existing populations of Treg T-cells can be engaged, activated and applied to the suppression of unwanted immune responses in both systemic and limited, disease specific, contexts. Specific diseases that may benefit from pre-symptomatic dosing, contemporaneous dosing or post-symptomatic dosing using an escalation regime described herein can include, but not limited to: asthma, allergy, allergic airway inflammation, allergic encephalomyelitis, autoimmune arthritis, rheumatoid arthritis, Juvenile rheumatoid arthritis, reactive arthritis, psoriatic arthritis, sacroiliitis, isolated acute anterior uveitis, undifferentiated spondyloarthropathy, Type I Diabetes Mellitus, Multiple Sclerosis, Systemic Lupus Erythematosus, glomerulonephritis, Hashimoto's thyroiditis, Graves' disease, Scleroderma, Immune Dysregulation Polyendocrinopathy Enteropathy X-linked syndrome (IPEX syndrome), Celiac disease, Coombs-positive hemolytic anemia, autoimmune thrombocytopenia, autoimmune neutropenia, Crohn's disease, inflammatory bowel disease, ulcerative colitis, ankylosing spondylitis, Sjogren's syndrome, psoriasis, contact dermatitis, Goodpasture's syndrome, Addison's disease, Wegener's granulomatosis, tubular nephropathy, Primary biliary cirrhosis, Sclerosing cholangitis, Autoimmune hepatitis, Polymyalgia Rheumatica, Bechet's disease, Guillain-Barre syndrome, various vasculitides, uveoretinitis, thyroditis, myasthenia gravis, immunoglobulin nephropathies, myocarditis, and progressive systemic sclerosis.

In some embodiments, the therapeutic methods provided herein for upregulating Treg T-cell levels provide a therapeutic benefit to a subject in need thereof. In some embodiments, the methods and/or the upregulation of Treg T-cells provide for upregulation of Treg T-cells above the subject's baseline level of said Treg T-cells. Baseline levels can be determined prior to administration of the therapeutic mAb TOL101. In some embodiments, upregulation of Treg T-cells generally refers to increasing the number of local or systemically circulating Treg cells that are CD2+ CD4+ CD25+ FOXP3+ CD127lo for the particular subject that are above 5% of the baseline level, or are above 10%, or are above 1.5%, or are above 20%, or are above 25%, or are above 30%, or are above 50% of the baseline concentration of CD2+ CD4+ CD25+ FOXP3+ CD127lo Treg T-cells prior to the escalation dosing of TOL101. The upregulation of Treg T-cells are nonetheless, therapeutically effective in blocking, preventing, treating or suppressing any one or more symptoms or conditions associated with alloreactive. T-cells, or for inhibiting cytotoxic T-cell (CTL) activity, or immunosuppressing an alloresponse, or inhibiting an autoimmune response, or inhibiting, preventing or blocking an alloresponse or an autoimmune response prior to, during or subsequent to tissue transplantation, or inhibiting, suppressing or blocking graft vs. host disease, or preventing, treating or suppressing an autoimmune response in an inflammatory disease, or autoimmune disease. In some embodiments, the subject, for example, a human or other mammalian subject can be assessed prior to treatment to determine their general medical condition to establish any preexisting autoimmune disease or predilection for auto- or allo-tissue rejection. In this embodiment, blood from the subject is drawn and T-cells and other white blood cell counts are made. These can also include the concentration of pre-treatment Treg T-cells and other markers of alloreaction or tissue rejection, and autoimmune disease relevant to the prognosis or medical treatment to be performed. In some embodiments, the concentration of Treg T-cells per milliliter of whole blood present in the subject is determined prior to commencing the dosing schedule to obtain a baseline level of CD2+ CD4+ CD25+ FOXP3+CD127lo Treg T-cells per milliliter of whole blood in the subject. During and upon completion of the escalation dosing of TOL101 mAB, routine blood draws can be made to determine the numbers of CD2+ CD4+ CD25+ FOXP3+ CD Treg T-cells per milliliter of whole blood in the subject to confirm upregulation of Treg T-cells using standard immunological techniques, for example, flow cytometry using 1, 2 or 3 color immunofluorescence staining specific for cell surface markers of Treg T-cells phenotypically expressing CD2+ CD4+ CD25+ FOXP3+ CD12710 cell surface markers.

Example 7

TOL101 Safety and Efficacy

The TOL101 clinical study in kidney transplant patients was conducted as described above in Example 6.

Safety Parameters.

Multiple safety parameters were monitored including general clinical safety measurements such as aberrant vital signs, physical signs and symptoms, and serum chemistry or hematology. Events were classified as adverse events (AE) or serious adverse events (SAE) according to organ system using Good Clinical Practice guidelines. Adverse event coding was done using the Medra dictionary. Subjects who suffered the same event more than once were recorded as suffering one event. Subjects who have more than one adverse event within a system organ class were counted only once in that system organ class. Immune safety parameters including symptoms that may suggest cytokine release syndrome were monitored. In addition, serum levels of TNF, Interferon-γ, Interleukin 6 (IL6), interleukin 1B (IL1) and interleukin 2 (IL2) were determined at 0, 2, 8 and 24 hours after the first dose. Cytokines were measured using luminex technology. Nitric oxide levels were also determined using calorometric assay at 0, 2, 8 and 24 hours after the first dose as well as on day 4. Human anti-mouse antibody was determined at baseline, day 14 and day 28, using sandwich ELISA. TOL101 was used as the primary antibody.

The incidence of malignancies including lymphoproliferative disorder was collected. In addition viremia for CMV (days 28, 90, and 180), BKV (days 90 and 180) and EBV (days 28, 90, and 180) was performed using PCR detection. The incidence of other serious or opportunistic infections was also collected.

Efficacy Parameters.

Clinical efficacy, was determined by the pharmacodynamic effect of TOL101 on $CD3^+$ T lymphocyte counts. Successful T cell modulation was considered present in patients with sustained CD3+ T cell numbers below 25 CD3+ counts per $mm^3$, although a decrease of CD3 counts of 90% from baseline is believed sufficient, for the continuous dosing interval. In addition, the traditional triple endpoint including patient survival, graft survival and Biopsy-Proven Acute Rejection (BPAR) at 6 months was determined. Delayed graft function was defined as the need for dialysis within the first week post transplant. Renal function was determined by estimated Glomerular Filtration Rate (GFR) at each study visit (MDRD method), with measured GFR determined by iothalamate clearance at day 180. The urine protein to creatinine ratio as well as Donor-Specific Antibody (DSA) was measured at day 90 and day 180.

Maintenance Immune Suppression.

Maintenance immunosuppression consisted of oral or IV Mycofenolate Mofetil (MMF; minimum 750 mg twice daily) was initiated on the day of transplant. Tacrolimus was initiated between Study Day 1 and Study Day 6, depending on the condition of the subject. The starting dose of tacrolimus was 0.1-0.2 mg/kg. Subsequent doses of tacrolimus were individualized to maintain whole blood $C_0$ levels in the range of 8-15 ng/mL for the first month post-transplant. Minimum tacrolimus $C_0$ level measurements were done daily during TOL101 administration, weekly month one, and on Days 90 and 180.

The initial dose of corticosteroids was 500 mg at transplantation, 250 mg on day 2, 125 mg on day 3 at d 0.5 mg/kg from day 4, tapered to 5-10 mg/day by month 1 and to ≧5 mg/day at day 45 until month 6.

Anti-Infective Prophylaxis.

Oral valganciclovir (Valcyte®) was recommended in CMV+ recipients or in recipients of kidneys from CMV+ donors. Oral trimethoprim/sulfamethoxazole (TMP/SMX; Septra SS®/Bactrim®) was required for 6 months for prophylaxis of *Pneumocystis carinii* pneumonia (PCP).

Administration of TOL101.

TOL101 was provided in 14 mg lyophilized vials (Tolera Therapeutics, Inc Kalamazoo, Mich., USA). Subjects received at least six daily doses of TOL101, beginning in the operating room on Day 0, through a central venous catheter. This study was designed to test ascending doses of TOL101, using CD3 T cell counts as the primary marker of efficacy, as outlined in Table 12. Due to the potential immune stimulatory capacity of TCR targeting antibodies, the initial TOL101 dose used was 1/10 of the calculated Minimum Adverse Biological Effect Level (MABEL), which was 0.28 mg. Further safety considerations included a 24-hour hold between patients and regular data safety monitoring board review of patient data. CD3 counts were measured at a central facility (Neogenomics; Orange County, Calif.) using the Beckman Coulter CD3 flow cytometry kit. A dose was considered to be efficacious if CD3 counts were <25 T cells per $mm^3$ throughout the dosing period. TOL101 dosing was ceased after a minimum of 6 doses, if the tacrolimus $C_0$ levels were therapeutic (8-15 ng/mL).

Pharmacokinetics.

Serum concentrations of TOL101 were measured daily at several time points after administration of Dose #1 (Day 0), Dose #4, the last dose, and on Day 14. A sandwich ELISA for mouse IgM was utilized (ABS laboratories, Colombia M1). A population pharmacokinetic model was developed for TOL101 by fitting a compartmental model to a pooled data set that includes data from all observations and doses from all subjects. Modeling will take into account any changes in the dose or infusion rate within or among doses. Models will be parameterized in terms of the appropriate number of clearances (CL) and volumes of distribution (V); elimination half-life (t½) will be estimated from the fitted parameters. Population modeling will be performed using NONMEM Version 7.0 or higher. Covariates (age, body size, gender, race, etc.) will be incorporated into the model based on improvement in the objective function and/or quality-of-fit graphics. Graphics of observed and model-predicted serum concentrations will be prepared using R Version 2.10 or higher.

Statistics.

The number of subjects per cohort is not based on statistical considerations but intended to provide safety and PD data sufficient to escalate to the next dose level, Frequency tables have been presented for all infections, AEs, all AEs by maximum severity, drug-related AEs, SAEs, and AEs resulting in study drug discontinuation. For quantitative laboratory tests, summary statistics are presented at each time point. Frequency tables will be presented summarizing the counts of subjects exhibiting cytokine release syndrome. Both measured and estimated GFR will be summarized with descriptive statistics. Delayed graft function and episodes of BPAR will be summarized in frequency tables. For the urine protein to creatinine ratio and the DSA assessments, summary statistics will be presented for the values obtained at Day 90 and Day 180/EOS. Patient and graft survival will be analyzed using the Kaplan-Meier product limit procedure and the log-rank test to compare survival curves.

Results

Patient Characteristics.

Patient enrollment began in February 2010 and ended April 2012 with enrollment at 6 centers in the United States. A total of 28 patients were enrolled into this Phase 2a study, with subjects entered into cohorts of escalating TOL101 dose as shown in Table 12. Enrollment represented a broad cross section of patients (Table 13). The mean donor age was 40 years of age: 24 subjects received kidneys from living donors, and 4 subjects received kidneys from cadaveric donors. The mean recipient age was 44 years, with 79% of these patients being male. Subjects were primary renal transplant recipients with low to moderate risk for rejection. Importantly, the risk profile of the patients enrolled increased with dose. Patients in the first 4 cohorts were generally of lower immunological risk. The final dose escalation cohort included 4 deceased donor transplants and 3 African American recipients. The most common causes of End Stage Renal Disease (ERSD) were polycystic kidney disease (33%) and Glomerulonephritis (33%).

TABLE 12

TOL101 Dosing Cohorts

| Cohort | Dose (mg/patient) | Sample Size |
|---|---|---|
| 1 | 0.28 | 2 |
| 2 | 2.4 | 2 |
| 3 | 7 | 2 |
| 4 | 14 | 2 |
| 5 | 28 | 6 |
| 6 | 32 | 4 |
| 7 | 42 | 4 |
| 8 | D 0- 14<br>D 1- 21<br>D 2- 28<br>D 3- 42<br>D 4- 42<br>D 5- 42 | 6 |

TABLE 13

Patient Demographics and Baseline Characteristics

| | Recipients | Donors |
|---|---|---|
| Primary/Re-transplants | 28/0 | NA |
| Age at transplant, mean (years) | 44.4 | 40 |
| Gender, n (%) | | |
| Male | 22 (79) | 13 (46) |
| Female | 6 (21) | 15 (54) |
| Race, n (%) | | |
| White | 21 (75) | 21 (75) |
| Black | 5 (18) | 5 (18) |
| Asian | 1 (3.5) | 0 |
| Other | 1 (3.5) | 2 (7) |
| Cause of Renal Failure, n (%) | | |
| Hypertensive Nephrosclerosis | 4 (14) | N/A |
| Polycystic Kidney Disease | 7 (25) | |
| Diabetes | 4 (14) | N/A |
| IgA Nephropathy | 5 (18) | N/A |
| Focal Segmental Glomerulonephritis | 3 (11) | N/A |
| Other | 5 (18) | N/A |
| Type of Donor, n (%) | | |
| Living, related | NA | 13 (46) |
| Living, unrelated | NA | 11 (39) |
| Deceased | NA | 4 (15) |
| HLA Mismatch, n (%) | | |
| 0 | 0 (0) | N/A |
| 1 | 2 (7) | N/A |
| 2 | 1 (4) | N/A |
| 3 | 9 (32) | N/A |
| 4 | 3 (11) | N/A |
| >5 | 13 (46) | N/A |
| Panel-reactive Antibody at Baseline | | |
| Mean (%) | 4% | N/A |
| ≧20, n (%) | 1 (25%) | N/A |
| Donor Specific Antibody | | |
| Month 3 | 0/28 (0) | N/A |
| Month 6 | 0/28 (0) | N/A |
| Cold-ischemia Time | | |
| Mean (hours) | 3 ± 5 | N/A |
| Delayed Graft Function | | |
| Deceased Donor, n (%) | 0 | N/A |
| Living Donor, n (%) | 0 | N/A |
| Pretransplant CMV Antibody Status, n (%) | | |
| Positive | 9 (33) | 12 (48) |
| Negative | 19 (67) | 13 (52) |
| Pretransplant CMV Antibody Match, n (%) | | |
| Donor+/Recipient− | 2 (7) | N/A |
| Donor+/Recipient+ | 7 (25) | N/A |
| Donor−/Recipient− | 13 (46) | N/A |
| Donor−/Recipient+ | 6 (21) | N/A |

Serious Adverse Events.

35 Serious Adverse Events (SAEs) have been reported in 11 subjects (Table 14). No deaths were observed. All but 1 SAE was considered to be "unrelated" to study drug. The possibly related SAE was a nosocomial pneumonia. Other SAE's were associated with surgery and other non-TOL101 related issues.

TABLE 14

Serious Adverse Events (SAEs)

| Serious Adverse Event | Patients, n (%) |
|---|---|
| All | 11 (39.3) |
| Blood & Lymphatic Disorders | |
| Leukopenia | 1 (3.6) |
| General Disorders & Administration Site Disorders | |
| Chest Pain | 2 (7.1) |
| Pyrexia | 1 (3.6) |
| *Escherichia* bacteremia | 1 (3.6) |
| Foiliculitis | 1 (3.6) |
| Metabolic & Nutritional Disorders | |
| Dehydration | 2 (7.1) |
| Gastrointestinal Disorders | |
| Pancreatitis | 2 (7.1) |
| Acute Pancreatitis | 1 (3.6) |
| Retroperitoneal hematoma | 1 (3.6) |
| Constipation | 1 (3.6) |
| Gastritis | 2 (7.1) |
| *Clostridium difficile* colitis | 1 (3.6) |
| Nervous System | |
| Transient Ischemic Attack | 1 (3.6) |
| Reproductive System | |
| Dysmenorrhea | 1 (3.6) |
| Respiratory System | |
| Atelectasis | 1 (3.6) |
| Pneumonia | 1 (3.6) |
| Urogenital System | |
| Renal Artery Stenosis | 1 (3.6) |
| Renal Hematoma | 1 (3.6) |
| Vascular | |
| Hypertension | 1 (3.6) |

Adverse Events (AEs).

A total of 521 AEs have been reported in 28 subjects, including 29 AEs in 18 subjects that were reported to be "possibly," "probably," or "definitely" related to TOL101. AEs that occurred in ≧15% of patients are shown in Table)$_5$. The majority of AEs were reported in the 28, 32, and 42 mg dose cohorts. Three subjects discontinued drug due to an AE (urticarial rash and puritis); each of these were in the 42 mg dose group. The most commonly reported related AE was a rash, as shown in Table 15. The observed rashes were variably described as urticarial, red, raised, hives, and/or weal like, in no case was the rash determined to be necrotic or long-lasting, and it never progressed to more severe manifestations.

TABLE 15

Commonly Occurring Adverse Events

| Adverse Event | Patients, n (%) |
|---|---|
| All | 18 (100) |
| Blood & Lymphatic Disorders | |
| Anemia | 5 (17.9) |
| Leukopenia | 5 (17.9) |
| General Disorders & Administration Site Disorders | |
| Fatigue | 7 (25) |
| Oedema peripheral | 5 (17.9) |
| Incision site pain | 5 (17.9) |
| Procedural pain | 5 (17.9) |
| Metabolic & Nutritional Disorders | |
| Dehydration | 2 (7.1) |
| Hyperglycemia | 10 (35.7) |
| Hyperkalaemia | 5 (17.9) |
| Hypomagnesaemia | 16 (57.1) |
| Hypophosphataemia | 9 (32.1) |
| Hyperlipidaemia | 5 (17.9) |

TABLE 15-continued

Commonly Occurring Adverse Events

| Adverse Event | Patients, n (%) |
|---|---|
| Gastrointestinal Disorders | |
| Constipation | 11 (39.3) |
| Diarrhoea | 12 (42.9) |
| Nausea | 28 (50) |
| Vomiting | 6 (21.4) |
| Nervous System | |
| Tremor | 10 (35.7) |
| Skin & subcutaneous tissue | |
| Pruritus | 9 (32.1) |
| Urticaria | 5 (17.9) |
| Vascular | |
| Hypertension | 9 (32.1) |
| Hypotension | 7 (25) |

In most but not all patients that experienced a rash, the rash occurred after the first dose of TOL101 (Table 16). In all cases, the rash disappeared on its own or after treatment with diphenhydramine, typically within a few hours. The rash did not recur at any dose level except the 42 mg, cohort. When it did recur, typically it was less intense, and did not preclude continued TOL101 dosing. Without wishing to be bound by theory, one potential cause for the observed rash was considered to be release from T cells of pre-formed non-classical soluble mediators with vasodilation potential. Since these were considered to be preformed, a dose escalation strategy was employed with the goal of exhausting these T cell stores and reducing rash incidence. As shown in Table 16, the utilization of a dose escalation protocol allowed for 42 mg dosing with reduced rash incidence. Overall, the results of the study indicated that TOL101 could be safely administered. In particular, the escalating dosing strategy was associated with minimal adverse effects.

TABLE 16

Incidence of Rash.

| Treatment Group (mg TOL101) | Patient | Dose 1 | Dose 2 | Dose 3 | Dose 4 | Dose 5 | Dose 6 | Dose 7 | Dose 8 |
|---|---|---|---|---|---|---|---|---|---|
| 0.28 mg | 06-001 | | | | | | | | |
| | 08-001 | | | | | | | | |
| 1.4 mg | 02-001 | | | | | | | | |
| | 04-001 | | | | | | | | |
| 7.0 mg | 02-002 | | | | | | | | |
| | 04-002 | | | | | | | | |
| 14.0 mg | 05-001 | | | | | | | | |
| | 08-002 | | | | | | | | |
| 28.0 mg | 01-001 | | | | | | | | |
| | 04-003 | | | | | | | | |
| | 07-001 | | | | | | | | |
| | 03-001 | | | | | | | | |
| | 07-003 | | | | | | | | |
| | 07-004 | | | | | | | | |
| 32.0 mg | 03-002 | | | | | | | | |
| | 08-004 | | | | | | | | |
| | 12-001 | | | | | | | | |
| | 07-005 | | | | | | | | |

TABLE 16-continued

| | | | | | | | | | |
|---|---|---|---|---|---|---|---|---|---|
| 42 mg | 06-002 | ■ | ■ | □ | □ | □ | □ | □ | □ |
| | 07-002 | ■ | ▨ | ▨ | ■ | ▨ | ▨ | □ | □ |
| | 04-004 | ■ | ■ | □ | □ | □ | □ | □ | □ |
| | 08-003 | ■ | ■ | □ | □ | □ | □ | □ | □ |
| 42 mg Escalation | 07-006 | 14 mg | 21 mg | 28 mg | 42 mg | 42 mg | 42 mg | □ | □ |
| | 07-007 | 14 mg | 21 mg | 28 mg | 42 mg | 42 mg | 42 mg | □ | □ |
| | 07-008 | 14 mg | 21 mg | 28 mg | 42 mg | 42 mg | 42 mg | □ | □ |
| | 08-005 | 14 mg | 21 mg | 28 mg | 42 mg | 42 mg | 42 mg | □ | □ |
| | 07-009 | 14 mg | 21 mg | 28 mg | 42 mg | 42 mg | 42 mg | □ | □ |
| | 02-003 | 14 mg | 21 mg | 28 mg | 42 mg | 42 mg | 42 mg | □ | □ |

Light gray squares indicate no rash was observed after dosing;
black squares indicate a rash was observed after dosing;
open squares indicate no dose was administered on the indicated day.

Infections and Malignancies.

No malignancies have been reported to date in subjects who received TOL101. Table 17 outlines all the infections observed in the study. Only one significant infection was considered to be potentially associated with TOL101, a nosocomial pneumonia, as described above. However, no culture was taken from this patient and as such a definitive diagnosis and causative agent cannot be identified. Skin associated infections were predominately incisional wound bacterial infections, with one case of folliculitis reported. Three cases of BK virus viremia were detected, two of which emerged shortly after thymoglobulin rescue in patients suffering acute rejection episodes. Other important infections such as CMV, EBV or opportunistic *pneumocystis* pneumonia were not observed.

TABLE 17

Infections and Malignancies

| Infections | Patients, n (%) |
|---|---|
| Bacterial | |
| UTI | 1 (3.5) |
| Skin | 5 (17.9) |
| Pneumonia | 1 (3.5) |
| Sepsis | 1 (3.5) |
| Viral | |
| CMV | 0 (0) |
| BK | 3 (10.7) |
| EBV | 0 (0) |
| Fungal | |
| *Candida* | 0 (0) |
| other | 0 (0) |
| Opportunistic | |
| PCP | 0 (0) |
| Cancer | |
| PTLD | 0 (0) |
| Solid Organ | 0 (0) |

Immunological Safety Parameters.

Figure 31:
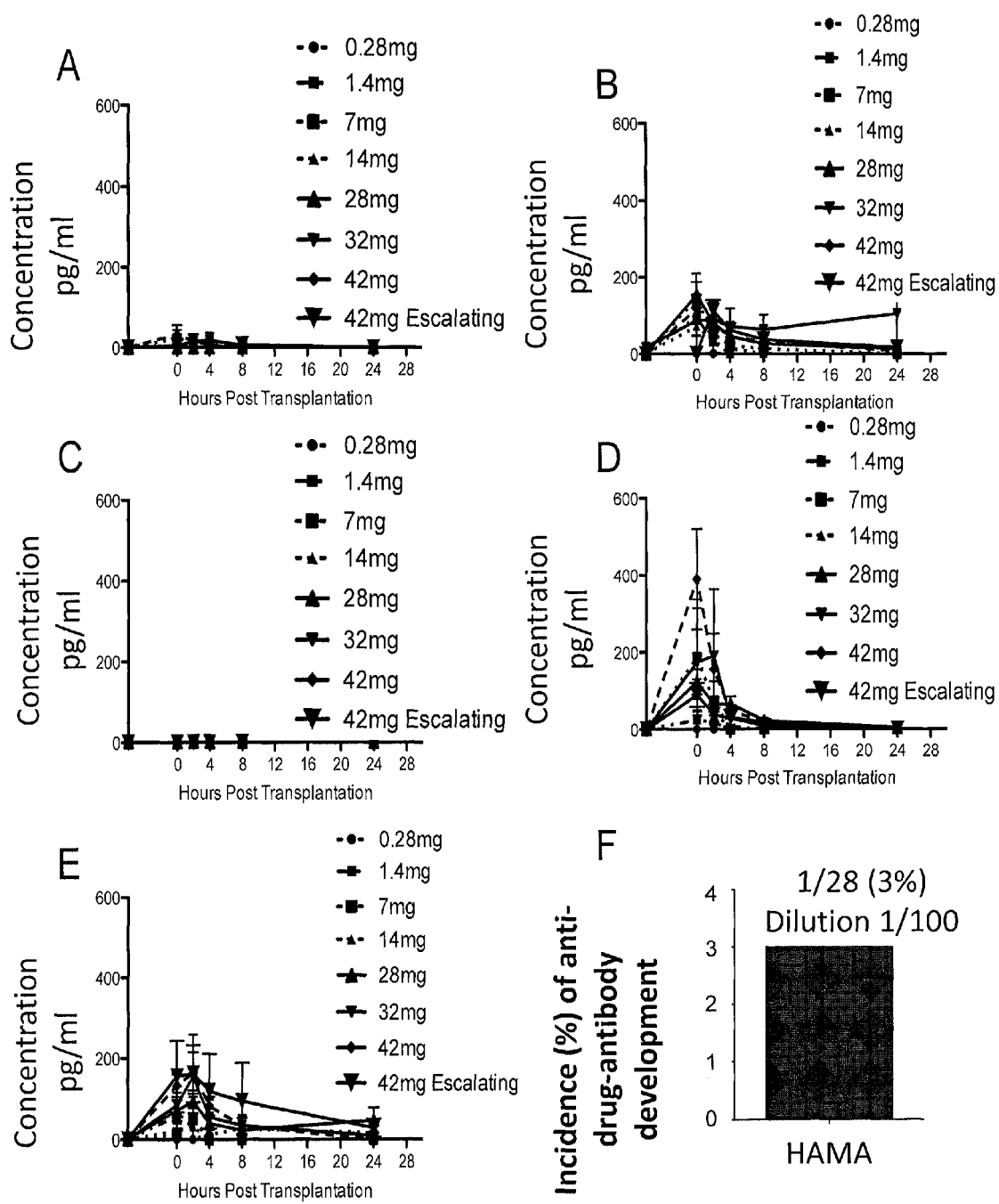

As noted in the AE tables, symptoms associated with cytokine release syndrome were not commonly observed. The lack of symptoms was supported by the low levels of TNF, IFN-γ, IL6, IL1β and IL2 (FIG. 31 A-E), which were either not detected or detected at low levels relative to those described in patients given rATG. Furthermore, another potentially inflammatory marker, indicative of infusion reactions, includes the production of nitric oxide (NO). NO was not detected in any TOL101 treated patient. As TOL101 is a murine antibody, the detection of HAMA was an important part of the study. Samples were assessed for HAMA development at days 0, 14 and 28 post transplant. In all but one patient, no HAMA was detected (FIG. 31F). The titer for the one patient with a positive HAMA sample was 1/100. The low incidence of HAMA was a surprising result, as other anti-TCR antibodies or CD3 antibodies, including T10B9, OKT3 and BMA-031, induced HAMA in greater than 30% of patients, with some studies reporting 80% incidence of HAMA (Waid et al. Transplantation 64; 274-281 [1997]). Without wishing to be bound by theory, it is believed that the low incidence of HAMA is reflective of the novel mechanism of action of the antibody and/or the post-translational modifications of the antibody (such as glycosylation).

Pharmacodynamic CD3 Modulation.

Peripheral blood CD3 T cell counts were measured daily during dosing. Dosing of TOL101 was administered once per day for a minimum of 5 days (six doses), or until therapeutic tacrolimus levels were reached (8-15 ng/ml). In 6 patients, more than 6 doses of TOL101 were required; however, none of these were in cohorts whereby TOL101 met the CD3 suppression target. In all patients, a primary reduction in leukocyte counts, including CD3 expressing cells, was observed immediately after transplant. This is commonly observed in patients receiving intravenous steroid infusion. Within 48-72 hours circulating CD3 counts increased above the $25/mm^3$ target in patients receiving 0.28, 1.4, 7 and 14 mg TOL101 (FIG. 32). In the 28 mg cohort, CD3 counts remained under $25/mm^3$, with the exception of one patient who experienced a spike in CD3 numbers on day 3. Whilst 28 mg appeared to be a promising dose regimen, the one potential outlier triggered escalation of TOL101 to 32 mg and 42 mg. At both of these dosing regimens robust CD3 suppression was achieved; however, a rash was observed in 50% and 100% of patients in the 32mer and 42 mg cohorts, respectively. Without wishing to be bound by theory, it was determined that the rash may be a result of pre-formed T cell soluble mediator release. Thus, a dose escalation strategy focused on exhausting these stores at sub-symptomatic levels was implemented. In this dosing regimen, dosing was initiated at 14 mg and rapidly escalated to 42 mg by the fourth dose. This dosing regimen not only reduced the propensity for rash development but also resulted in robust CD3 suppression, meeting the pharmacodynamic target.

Recovery of CD3 expression after TOL101 dosing was observed to occur in all patients by day 14 (FIG. 32). This recovery points to a non-depletional mechanism of action, which is also supported by the observation that there was no decrease in white blood cell counts during dosing.

Pharmacokinetics.

Similar to OKT3 and other anti-TCR therapies, elimination of TOL101 is thought to be predominately mediated through binding to its target protein. Examination of the pharmacokinetics show that in those cohorts whereby robust CD3 suppression was achieved (i.e., 28, 32, 42 mg and dose escalation cohorts; FIG. 31G), the half-life of TOL101 ranged from 23 to 29 hours (Table 18), Peak concentrations of TOL101 were achieved after 3 days of dosing, potentially indicating target saturation at this time point.

TABLE 18

Pharmacokinetics Summary
Pharmacokinetic Summary

| 28 mg Cohort (n = 6) | | 32 mg Cohort (n = 4) | | 42 mg escalating doses (n = 6) | |
|---|---|---|---|---|---|
| Primary | | | | | |
| CL (mL/h) | 244 ± 144 | CL (mL/h) | 201 ± 58.6 | CL (mL/h) | 216 ± 46.4 |
| Secondary | | | | | |
| T½ (hr) | 22.8 ± 6.34 | T½ (hr) | 25.5 ± 11.1 | T½ (hr) | 29.8 ± 18.8 |
| Peak concentration (pg/ml) | | | | | |
| Day 0 end infusion | 4.2 ± 1.1 | Day 0 end infusion | 5.7 ± 1.7 | Day 0 end infusion | 1.7 ± 1.1 |
| Day 4 end infusion | 9.6 ± 3.4 | Day 4 end infusion | 9.4 ± 2.8 | Day 4 end infusion | 10.3 ± 2.8 |

Efficacy Composite Triple Endpoint.

There were no patient or graft losses reported in study (FIG. 33A). Three subjects experienced biopsy proven acute rejection episodes described as possibly related to study drug, All rejection episodes were treated with steroids or Thymoglobulin and resolved clinically without graft loss. No donor specific antibody has been detected in any patient enrolled into the study.

Kidney Function.

No delayed graft function was observed in the study, Kidney function improved throughout the study, with increases in estimated GFR observed in all patients (FIG. 33B). In addition, calculated GFR, using iothalamate clearance at day 180 post transplant showed excellent creatinine clearance across all patients (FIG. 33C), including those that had suffered acute rejection events.

Example 8

TOL101 Specificity

Peripheral blood monocytes (PBMC) from 6 independent donors were used to determine the precise T cell subset that TOL101 binds. TOL101 labeled only CD3+ T cells, and bound to both CD4+ and CD8+ T cells (FIG. 34). Importantly, TOL101 did not bind to γδT cells, cells expressing CD14 (monocyte lineage/NK cells), or B cells (FIG. 34). Thus, TOL101 is specific for αβ T cells. Further, preincubation with TOL101 blocked binding of another αβ TCR antibody, IP26, further demonstrating TOL101's specificity for αβT cells, Antibodies specific for the α chain of the TCR inhibited TOL101 binding, whereas β chain antibodies exhibited much less inhibition of TOL101 binding. Thus, TOL101 appears to preferentially bind to the alpha chain of the TCR.

Example 9

TOL101 Signaling and In Vitro Treg Induction

TOL101-mediated T cell inhibition was further examined using 1 way mixed lymphocyte reaction (MLR). In this experiment, PBMCs were isolated from huffy coats of three healthy donors. Buffy coats were layered over a Ficol gradient to enrich for lymphocytes. Stimulator cells were then irradiated at 3000 rads. Stimulator and responder cells were co-cultured for 7 days at a ratio of 2:1 (4e5 stimulator cells to 2e5 responder cells). Combinations for cells were as follows: unit 1+unit 2 irr (Ab), unit 1+unit 3 irr (Ac), unit 2+unit 1 irr (Ba), unit 2+unit 3 irr (Bc), unit 3+unit irr (Ca), unit 3+unit 2 irr (Cb), TOL101 was added at time of culture at concentration of 9 ug/mL. Brefeldin A was added the last 24 hours of culture. Cells were harvested and stained for extracellular antigens, fixed and permeabilized and stained for intracellular cytokines. The graphs in FIG. 35 show the percentage of CD4 T cells expressing IFN-γ, in support of the clinical data obtained, TOL101 inhibited type 2 interferon from T cells in the one-way MLR from numerous individual patients.

As described in Example 3, TOL101 has been shown to increase the levels of phosphorylated ERK (FIG. 1)) and reduce the level of phosphorylated ZAP70 (FIG. 10). ERK phosphorylation in T cells is commonly associated with T cell co-stimulatory pathways, including the CD28 pathway. An experiment was performed to determine if TOL101 may inhibit co-stimulation induced T cell proliferation, PBMCs were isolated from buffy coats of three healthy donors, Buffy coats were layered over a Ficol gradient to enrich for lymphocytes. Lymphocytes were cultured at a density of 2e5 Cells were cultured with TOL101 (9 μg/mL), plate-bound CD28 (1 μg/mL), and plate-bound CD28 (1 μg/mL) and TOL101 (9 μg/mL). H$^3$ was added 4 days into culture and plates were harvested and counted on day 5. As can be seen in FIG. 36, TOL101 was unable to inhibit CD28-mediated proliferation.

In addition to ZAP70 and ERK, another indication of T cell activation is calcium flux. The sustained increase of calcium leads to activation of the phosphatase Calcineurin. Calcineurin regulates a number of transcription factors including NF-AT. To examine if TOL101 triggers calcium release, PBMCs were isolated from buffy coats of four healthy donors (O, P, Q & R). In FIG. 37, buffy coats were layered over a Ficol gradient to enrich for lymphocytes. 5e5 cells from each donor were stained with anti-CD4 for 1 hour at 37° C. Cells were washed and raised in Fluo-4 direct calcium assay reagent solution (Invitrogen #F10471) and incubated for 30 minutes at 37° C. and 30 minutes at RT. Cells were run on LSR for 600 seconds. At T=90 seconds, 20 μL of media alone, or 20 each of 9 μg/mL TOL101 and 9 μg/mL anti-mouse IgM, or 20 μL each of 9 μg/mL CD3 and 9 μg/mL anti-mouse IgG, or 20 μL of 1 μg/mL ionomycin added to tubes and gently pipetted up and down before continuing acquisition. Surprisingly, TOL101 induced calcium flux in only about 15% of CD4 T cells, unlike anti-CD3, which resulted in essentially all CD4 T cells fluxing calcium (FIG. 37). Without wishing to be bound by theory, it is believed that the small number of CD4 T cells fluxing calcium upon binding of TOL101 represents the T cells that will become Tregs.

In addition to calcium flux, phosphorylated heat shock protein 27 (HSP27), AKT-2 and the MAPK activated protein kinase where examined in TOL101 treated T cells (FIG. 38). In this experiment, PBMCs were isolated from the buffy coat of healthy donors. Huffy coats were layered over a Ficol gradient to enrich for lymphocytes. Cells were kept at 37 degrees for one hour under one of the following conditions: no treatment, anti-CD3 (OKT3) 9 μg/mL+anti-mouse Ig 10 μg/mL, TOL101 9 μg/mL+anti-mouse IgM 10 μg/mL. After one hour, cells were washed and lysed. 200 μg of protein/sample was processed using the RD Human Phospho-MAPK Array, Phosphorylation of proteins were detected using streptavidin-HRP and chemiluminescent detection. A picture of exposed and developed membranes and a quantification of pixel intensity using ImageJ software are shown in FIG. 38. As shown in FIG. 38, HSP27 was not different between treatment groups. While a potential trend for P38a may have been observed, it was not significant. Most striking was the observation that the level of phosphorylated AKT2 was found in significant amounts in TOL101 treated PBMC but was undetected in anti-CD3 or control PBMCs. Together these data further highlight the unique modulation pathway initiated by TOL101 when it binds to the TCR.

As described above, the induction of Tregs in clinical patients treated with the escalation doses of TOL101 was unexpected (FIG. 28). Furthermore, the signaling events induced by TOL101, including increased. ERK, have been described to inhibit the expansion of Tregs. To further explore these results, the ability for TOL101 to induce Tregs was further examined in-vitro. PBMCs were isolated from huffy coats of three healthy donors. Buffy coats were layered over a Ficol gradient to enrich for lymphocytes. Two-way MLR cultures, representative of an in vivo allograft transplant patient, were set up in a 1:1 ratio of 4e5 cells/donor. Cells were cultured with TOL101 in escalating concentrations to reflect the clinical experiment dosing. Increasing concentrations of TOL101 (9, 18, 36, 72, and 120 μg/mL), a constant concentration of TOL101 (9 μg/mL), anti-CD3 (1 μg/mL) or media alone were added to cultures. Cells were collected after 5 days in culture, washed, blocked, stained for extracellular antigens, fixed and permeabilized and stained for intracellular Foxp3. Cells were collected by flow cytometry and analyzed with Flow Jo. Dot plots are representative of 3 reactions (A+B, A+C, B+C). Tregs with a CD4$^+$CD25$^+$FOXP3$^+$CD127$^{lo}$ phenotype have been shown previously to have in vivo suppression activity, and were gated as shown in FIG. 39. Strikingly, cultures treated with escalating doses of TOL101 were enriched for a CD4$^+$CD25$^+$FOXP3$^+$CD127$^{lo}$ Tregs. Anti-CD3 treated cultures had numerically more CD4$^+$CD25$^+$FOXP3$^+$CD127$^{lo}$, but there was also a significant CD127$^{hi}$ population, which is thought to be effector T cells. These effector T cells are highly effective at causing allograft rejection and autoimmunity. Taken together, the results of the study indicate that unexpectedly and in contrast to dogma, which indicates that signal 1 (TCR stimulation) without signal 2 (co-stimulation) results in T cell anergy and death, the unique signal-1 provided by TOL101 does not result in T cell depletion or death. Without wishing to be bound h theory, it is thought that binding of TOL101 to the αβ TCR induces phosphorylation of proteins, including AKT and ERK, which are known to be important in T cell survival, and that the survival signal, combined with calcium induced signaling, results in the induction of Tregs.

Example 10

TOL101 ScFV

In this experiment, a series of 10 different small chain variable fragments (scFv) expressing modified CDRs from TOL101 were expressed in *E. coli*. One of the 10 say exhibited a high expression profile (FIG. 40). A schematic diagram and the amino acid sequence of this scFv (SEQ ID NO: 9) are also shown in FIG. 40. The scFv bound both CD4+ and CD8+ T cells in vitro (FIG. 40), indicating that a TOL101 scFv can be generated with both T cell binding capacity and a high expression level.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. An isolated antibody produced by the hybridoma TOL101 MCB deposited with the ATCC under the accession number PTA-13293.

2. The isolated antibody according to claim 1, wherein the antibody is coupled to a detectable label selected from the group consisting of a radioisotope, enzyme, fluorescent label, luminescent label, bioluminescent label, biotin or toxin.

* * * * *